United States Patent [19]
Cohen et al.

[11] Patent Number: 5,877,221
[45] Date of Patent: Mar. 2, 1999

[54] COMPOSITIONS CONTAINING AND METHODS OF USING 1-AMINOINDAN AND DERIVATIVES THEREOF AND PROCESS FOR PREPARING OPTICALLY ACTIVE 1-AMINOINDAN DERIVATIVES

[75] Inventors: Sasson Cohen, Tel Aviv; Yaacov Herzig, Raanana; Ruth Levy, Tel Aviv; Jeff Sterling, Jerusalem; Alex Veinberg, Rehovot; Moussa B. H. Youdim, Haifa; John P. M. Finberg, Tivon, all of Israel

[73] Assignees: Teva Pharmaceutical Industries, Ltd., Jerusalem; Technion Research and Development Foundation, Ltd., Haifa, both of Israel

[21] Appl. No.: 953,097

[22] Filed: Oct. 17, 1997

Related U.S. Application Data

[60] Continuation of Ser. No. 477,163, Jun. 7, 1995, abandoned, which is a division of Ser. No. 372,064, Jan. 12, 1995, abandoned, which is a continuation-in-part of Ser. No. 179,539, Jan. 10, 1994, abandoned, and Ser. No. 179,607, Jan. 10, 1994, abandoned.

[51] Int. Cl.$^6$ .................... A61K 31/16; A61K 31/165
[52] U.S. Cl. ................. 514/629; 514/617; 514/625
[58] Field of Search ................... 514/657, 617, 514/625, 629

[56] References Cited

U.S. PATENT DOCUMENTS

| | | | |
|---|---|---|---|
| 2,573,645 | 10/1951 | Kerwin et al. | 564/391 |
| 2,982,783 | 5/1961 | Schenck et al. | 514/657 |
| 3,060,091 | 10/1962 | Witkin et al. | 564/428 |
| 3,123,642 | 3/1964 | Temple et al. | 564/288 |
| 3,178,478 | 4/1965 | Huebner | 564/428 |
| 3,201,470 | 8/1965 | Huebner | 514/657 |
| 3,253,037 | 5/1966 | Huebner | 564/428 |
| 3,308,157 | 3/1967 | Robertson et al. | 564/176 |
| 3,637,740 | 1/1972 | Sarges | 564/428 |
| 3,704,323 | 11/1972 | Krapcho | 564/428 |
| 3,709,996 | 1/1973 | Gittos et al. | 564/428 |
| 3,751,420 | 8/1973 | Hauck et al. | 514/657 |
| 3,991,207 | 11/1976 | Sarges et al. | 514/657 |
| 4,096,173 | 6/1978 | Molloy | 564/428 |
| 4,128,666 | 12/1978 | Bondinell et al. | 514/657 |
| 4,132,737 | 1/1979 | Molloy | 514/657 |
| 4,134,997 | 1/1979 | Cannon et al. | 424/330 |
| 4,172,093 | 10/1979 | Goransson-Dahlander et al. | 564/428 |
| 4,632,939 | 12/1986 | Beedle et al. | 514/619 |
| 4,788,130 | 11/1988 | Oshiro et al. | 514/661 |
| 4,833,273 | 5/1989 | Goel | 564/304 |
| 4,873,241 | 10/1989 | Napier et al. | 514/237.8 |
| 5,071,875 | 12/1991 | Horn et al. | 514/613 |
| 5,118,704 | 6/1992 | Minaskanvan et al. | 514/416 |
| 5,153,225 | 10/1992 | Schohe et al. | 514/602 |
| 5,225,596 | 7/1993 | Carlsson et al. | 564/428 |
| 5,286,747 | 2/1994 | Arvidlsson et al. | 514/481 |
| 5,389,687 | 2/1995 | Schaus et al. | 514/567 |
| 5,569,669 | 10/1996 | Guillaumet et al. | 514/432 |
| 5,646,188 | 7/1997 | Gilad et al. | 514/634 |
| 5,708,018 | 1/1998 | Haadsma-Sevnssonet et al. | 514/408 |

FOREIGN PATENT DOCUMENTS

0436492A2  10/1991  European Pat. Off. .

OTHER PUBLICATIONS

Oshiro, Y., et al., "Novel Cerebroprotective Agents with Central Nervous System Stimulating Activity. 1. Synthesis and Pharmacology of 1–Amino–7–hydroxyindan Derivatives" J. Medicinal Chem. (1991) 34(7): 2004–2013.

J. Pharm. Exp. Ther., 180:523–530, 1975.

Horn et al, "Steric Requirements for Catecholamine Up–take by Rat Brain Synapsomes Studies with Rigid Analogs of Amphetamine", J. Pharm. Exp. Ther., vol. 180, pp. 523–530, 1972.

Martin et al (I), "Potential anti–Parkinson drugs designed by receptor mapping", CA78:119099 from J.Med.Chem., vol. 16,No. 2, pp. 147–150, 1973.

Martin et al (II), "Discriminant Analysis of the Relationship Between Physical Properties and Inhibition of MAO by Aminotetralins and Aminoindans", J. Mod. Chem., vol. 17, No. 4, pp. 409–413, 1974.

Merck Manual, 15th Edition, pp. 1030–1033, 1987.

*Primary Examiner*—Deborah C. Lambkin
*Attorney, Agent, or Firm*—John P. White; Cooper & Dunham LLP

[57] ABSTRACT

Novel derivatives of 1-aminoindan and their salts are described. Optically active 1-aminoindan derivatives are prepared by reacting a N-benzyl analog of the desired compound with an enantiomer of mandelic acid. Parkinson's disease, dementia, epilepsy, convulsions, or seizures are treated by administering a compound of the formula:

[structure with $R_1$, $R_2$, $R_3$, $R_4$, $R_5$, $(CH_2)_n$, N]

29 Claims, 9 Drawing Sheets

COMPOSITIONS CONTAINING AND METHODS OF USING 1-AMINOINDAN AND DERIVATIVES THEREOF AND PROCESS FOR PREPARING OPTICALLY ACTIVE 1-AMINOINDAN DERIVATIVES

This is a continuation of application Ser. No. 08/477,163, filed Jun. 7, 1995, abandoned, which is a divisional of U.S. Ser. No. 08/372,064, filed Jan. 12, 1995, now abandoned, which is a continuation-in-part of U.S. application Ser. Nos. 08/179,539 and 08/179,607, both filed Jan. 10, 1994, both now abandoned, the contents of which are hereby incorporated by reference.

Throughout this application, various references are referred to. Disclosures of these publications in their entireties are hereby incorporated by reference into this application to more fully describe the state of the art to which this invention pertains.

BACKGROUND OF THE INVENTION

Various procedures for treating Parkinson's Disease have been established and many of them are currently in widespread use. European Patent No. 436492B provides a detailed discussion of treatments available and summarizes many of their drawbacks. There remains a need for a drug therapy that provides a prolonged and sustained amelioration of the symptoms associated with Parkinson's Disease.

A variety of substituted 1-aminoindans have been proposed to have some activity in the central nervous system (CNS). This group of compounds have a wide range of activities, for example, U.S. Pat. No. 4,096,173 discloses 1-aminoindans with ring chloro substituents as having anti-allergic, anti-spasmodic and local anesthetic activities, whereas U.S. Pat. No. 3,886,168 discloses the anti-inflammatory and vasodilatory activity of certain 1-aminomethylindans. It is hypothesized therein that the activity may be based in the CNS though no evidence is provided or suggested to support the hypothesis. British Patent No. 852,735 discloses 1-aminoindans with a lower alkoxy group in the 5 position as being active in dilating coronary blood vessels. U.S. Pat. No. 3,637,740 discloses 4-alkoxy-5-chloro-1-aminoindans as anti-depressants or anti-anxiety agents, although no clear evidence is provided of either activity.

Horn et al. (J.Pharm.Exp.Ther. 1972 180(3) 523) have shown that 2-aminoindan is a far superior inhibitor of catecholamine uptake than 1-aminoindan and therefore dismissed the latter as a candidate for use in the treatment of Parkinson's Disease. Martin et al. (J.Med.Chem. 1973 16(2) 147 & J.Med.Chem 1974 17(4) 409) describe experiments wherein N-methyl-5-methoxy derivatives of 1-aminoindan are investigated as having monoamine oxidase (MAO) inhibitory activity. Oshiro et al. (J.Med.Chem. 1991 34 2004–2013) disclose a wide range of 7-hydroxy-1-aminoindan derivatives that they subjected to screening for use as a cerebroprotective agent using an antihypoxic test and as a CNS stimulatory agent using a cerebral trauma test. In the resultant structure-activity-analysis undertaken it was found that replacement of the 7-hydroxy group by a methoxy group resulted in loss of activity in the antihypoxic test but not in the cerebral trauma test. Their conclusion was that the 7-hydroxy group is essential to obtain the desired activity. This is evident from their subsequent paper wherein a broader range of 7-hydroxy derivatives are screened (J.Med.Chem 1991 34 2014–2020). These 7-hydroxy-1-aminoindans are defined in U.S. Pat. Nos. 4,788,130, 4,792, 628, 4,895,847, 5,055,474 and 5,242919 all assigned to Otsuka Pharmaceutical Co. Japan.

It has surprisingly been found that a range of substituted and unsubstituted 1-aminoindans have activity in suppressing the symptoms emanating from the dopaminergic hypofunction that is associated with Parkinson's Disease; in improving cognition in dementias such as senile dementia, Parkinson-type dementia and dementia of the Alzheimer's type; in providing protection against epilepsy, convulsions, seizures; and in improving post-head trauma motor function, and reducing trauma-induced cerebral oedema.

The present invention also relates to a process for the synthesis of optically active aminoindan derivatives that have been described as possessing utility in the treatment of Parkinson's Disease, dementia, epilepsy, convulsions or seizures.

Several methods of preparing optically active derivatives of 1-aminoindan have been described in the art which include, for example, the method of Lawson and Rao, Biochemistry, 19, 2133 (1980), methods in references cited therein, and the method of European patent No. 235,590.

Optically active compounds containing an amine group attached to a chiral carbon atom may be prepared by the resolution of a racemic mixture of the R and S enantiomers. Such a resolution can be accomplished by resolution methods well known to a person skilled in the art, such as the formation of diastereomeric salts with chiral acids, or those described in U.S. Pat. No. 4,833,273, issued May 23, 1989 (Goel) and those listed in J. Jacques, A. Collet and S.Wilen, "Enantiomers, Racemates and Resolutions" Wiley, N.Y. (1981) such as tartaric, malic, mandelic acid, or N-acetyl derivatives of amino acids, such as N-acetyl leucine, followed by re-crystallization to isolate the diastereomeric salt of the desired enantiomer.

Kipping and Hall, J. Chem. Soc.(1901) 79 430, succeeded in the formation of diastereomeric alpha-bromocamphor-sulphonic acid salts of the compound N-benzyl-1-aminoindan. Isolation of the individual enantiomers by the addition of barium hydroxide failed and the racemate was obtained.

The preparation of the S enantiomer of the benzoate salt of N-benzyl-1-aminoindan from (S)-1-aminoindan has been described by Takaneda S et al. JCS Perkin II (1978) 95–99.

It is an object of this invention to provide an economical, commercially useful method for preparing optically active enantiomers of 1-aminoindan and derivatives thereof.

It has been surprisingly observed that by using a particular resolving agent on a particular class of 1-aminoindan derivative, a resolution is effected that produces high yields of optically active enantiomer.

SUMMARY OF THE INVENTION

This invention provides a method for treating Parkinson's disease, dementia, epilepsy, convulsions, or seizures in a subject comprising administering to the subject a therapeutically effective amount of a compound of the formula:

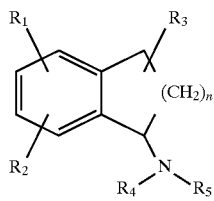
(Formula 1)

or a pharmaceutically acceptable salt thereof; wherein n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, halogen, nitro, NH—$R_3$, C(O)—$R_3$, or C(O)—$NR_9R_{10}$; $R_3$ is hydrogen, substituted or unsubstituted $C_1$–$C_4$ alkyl, hydroxy, substituted or unsubstituted $C_{1-4}$ alkoxy, or substituted or unsubstituted $C_{6-12}$ aryl; and $R_4$ and $R_5$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, —C(O)—$R_6$, —Y—C(O)—$R_7$, or Y—($SO_2$) $NR_9R_{10}$; wherein $R_6$ is hydrogen, hydroxy, substituted or unsubstituted $C_1$–$C_{12}$ alkyl, substituted or unsubstituted $C_7$–$C_{12}$ aryl, substituted or unsubstituted $C_7$–$C_{12}$ aralkyl, or A-$NR_9R_{10}$, wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or $NR_9R_{10}$, wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl. This invention provides a method for treating epilepsy, convulsions, or seizures in a subject comprising administering to the subject a therapeutically effective amount of a compound of the formula:

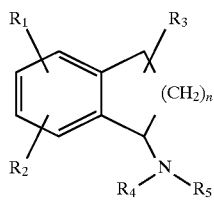
(Formula 1)

or a pharmaceutically acceptable salt thereof; wherein n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, halogen, nitro, NH—$R_3$, C(O)—$R_3$, or C(O)—$NR_9R_{10}$; $R_3$ is hydrogen, substituted or unsubstituted $C_1$–$C_4$ alkyl, hydroxy, substituted or unsubstituted $C_{1-4}$ alkoxy, or substituted or unsubstituted $C_{6-12}$ aryl; and $R_4$ and $R_5$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, alkynyl, —C (O)—$R_6$, —Y—C (O)—$R_7$, or Y—($SO_2$)$NR_9R_{10}$; wherein $R_6$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl, or A-$NR_9R_{10}$ wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or $NR_9R_{10}$, wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl.

This invention provides a compound selected from the group consisting of 7-methyl-1-aminoindan, 5-methyl-1-aminoindan, (R)-6-hydroxy-1-aminoindan, 3,5,7-trimethyl-1-aminoindan, 4,5-dimethoxy-1-aminoindan, (R)-4,5-dimethoxy-1-aminoindan, (S)-4,5-dimethoxy-1-aminoindan, 4-hydroxy-5-methoxy-1-aminoindan, 6-hydroxy-5-methoxy-1-aminoindan, N-(4-aminobutanoyl)-1-aminoindan, (R)-N-formyl-1-aminoindan, (S)-N-formyl-1-aminoindan, (R)-N-acetyl-1-aminoindan, N-acetyl-7-methyl-i-aminoindan, N-acetyl-6-fluoro-1-aminoindan, (R)-N-acetyl-6-fluoro-1-aminoindan, (S)-6-Methoxy-1-aminoindan, N-acetyl-6-methoxy-1-aminoindan, (R)-N-acetyl-4,5-dimethoxy-1-aminoindan, N-(2-acetamido)-1-aminoindan, (R)-N-(2-acetamido)-1-aminoindan, (S)-N-(2-acetamido)-1-aminoindan, N-(2-acetamido)-6-fluoro-1-aminoindan, N-(3-cyanopropyl)-1-aminoindan, N-(2-acetamido)-1-aminotetralin, N-(2-N-Boc-aminoacetyl)-1-aminoindan, N-(2-Aminoacetyl)-1-aminoindan, N-Benzoyl-1-aminoindan, N-(2-n-Propylpentanoyl)-1-aminoindan, N-methyl-N-acetyl-1-aminoindan, (R)-N-methyl-N-acetyl-1-aminoindan, N-(2-propionamido)-1-aminoindan, N-(2-phenylacetyl)-1-aminoindan, N-(m-anisoyl)-1-aminoindan, N-(4'-fluorobenzoyl)-1-aminoindan, N-(p-4-toluoyl)-1-aminoindan, (S)-(1-indanyl)-glycine, N,N-di-(2-acetamido)-1-aminoindan, N-(1-indanyl)-aminoacetonitrile 6-cyano-N-acetyl-1-aminoindan, 6-carboxamido-N-acetyl-1 -aminoindan, 6-ethoxycarbonyl-N-acetyl-1-aminoindan, 2-(1-indanamino)-N-isopropylethanesulfonamide, 2-(1-indanamino)-N-(1-indanyl)ethanesulfonamide, (R,R)-2-(1-indanamino)-N-(1-indanyl)ethanesulfonamide, N-(4-(di-n-propylsulfamoyl)benzoyl)-1-aminoindan, N,N'-bis-(1-indanyl)adipamide, N,N'-bis-(R)-(1-indanyl)adipamide, N,N'-bis(R)-(1-indanyl)succinamide, trans-2-methyl-N-acetyl-1-aminoindan, cis-2-methyl-N-acetyl-1-aminoindan, and salts thereof.

The compounds of general formula 1 possess neuroprotective activity. Accordingly, this invention provides a method for treating acute neurological traumatic disorder or neurotrauma in a subject comprising administering to the subject a therapeutically effective amount of a compound of the formula:

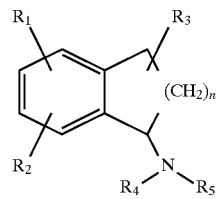
(Formula 1)

or a pharmaceutically acceptable salt thereof; wherein n is 0, 1 or 2; $R_1$ and $R_2$ are each independently hydrogen, hydroxy, substituted or unsubstituted $C_{1-C4}$ alkyl, substituted or unsubstituted $C_1$–$C_4$ alkoxy, halogen, nitro, NH—$R_3$, C(O)—$R_3$, or C(O)—$NR_9R_{10}$; $R_3$ is hydrogen, substituted or unsubstituted $C_1$–$C_4$ alkyl, hydroxy, substituted or unsubstituted $C_{1-4}$ alkoxy, or substituted or unsubstituted $C_{6-12}$ aryl; and $R_4$ and $R_5$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, —C(O)—$R_6$, —Y—C(O)—$R_7$, or Y—(SO$_2$)NR$_9$R$_{10}$; wherein $R_6$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl, or A—NR$_9$R$_{10}$, wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or NR$_9$R$_{10}$, wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl.

This invention provides a method for preparing an optically active enantiomer of a compound of the formula:

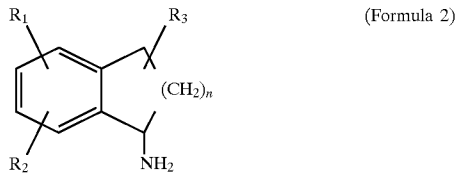

(Formula 2)

wherein the enantiomer is optically active at the $C_1$ position; n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, or halogen; and $R_3$ is hydrogen or unsubstituted $C_1$–$C_4$ alkyl;

comprising incubating in a reaction mixture a racemic N-benzyl analog of the compound with an optically active enantiomer of mandelic acid;

converting the optically active ammonium salt obtained to its corresponding optically active base;

and reducing the base to the optically active enantiomer of the compound.

This invention provides a method for preparing racemic N-benzyl-1-aminoindan comprising reacting 1-chloroindane with benzylamine in an inert solvent.

DETAILED DESCRIPTION OF THE INVENTION

Figure 1:
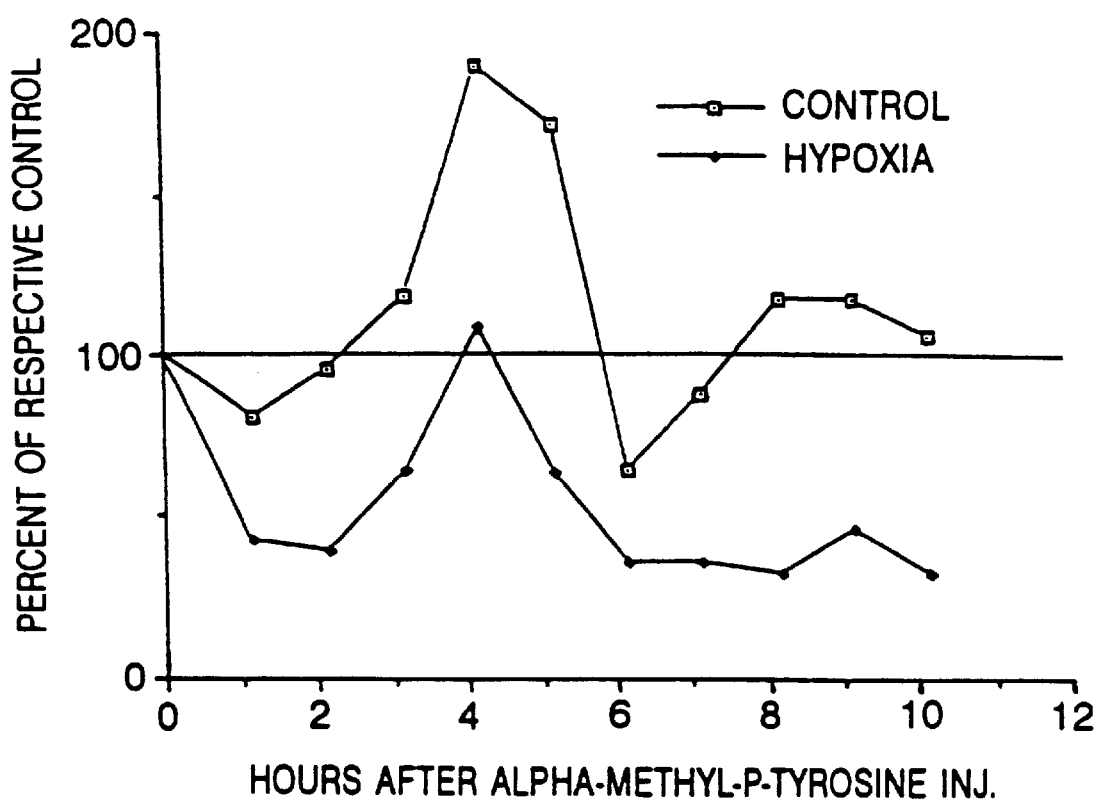
FIG. 1: Experiment 1A: α-MpT-induced hypokinesia in hypoxic rat. Effect of the hypoxia episode as compared to control animals. X-axis: hours after α-MpT injection. Y-axis: percent of respective control recorded as total movements.

This invention provides a method for treating Parkinson's disease, dementia, epilepsy, convulsions, or seizures in a subject comprising administering to the subject a therapeutically effective amount of a compound of the formula:

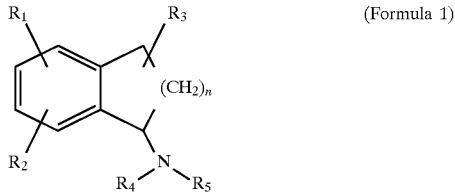

(Formula 1)

or a pharmaceutically acceptable salt thereof; wherein n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, halogen, nitro, NH—$R_3$, C(O)—$R_3$, or C(O)—NR$_9$R$_{10}$,; $R_3$ is hydrogen, substituted or unsubstituted $C_1$–$C_4$ alkyl, hydroxy, substituted or unsubstituted $C_{1-4}$ alkoxy, or substituted or unsubstituted $C_{6-12}$ aryl; and $R_4$ and $R_5$ are each independently hydrogen, substituted or unsubstituted $C_1$–$C_{12}$ alkyl, substituted or unsubstituted $C_1$–$C_{12}$ aryl, substituted or unsubstituted $C_7$–$C_{12}$ aralkyl, —C(O) —$R_6$, —Y—C(O)—$R_7$, or Y—(SO$_2$)NR$_9$R$_{10}$; wherein $R_6$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl, or A—$NR_9R_{10}$, wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or $NR_9R_{10}$ wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl.

One of skill in the art will appreciate that substituted or unsubstituted alkyl refers to both straight-chain and branched-chain alkyl groups. Halogen is used herein to refer to fluoro, chloro, bromo, and iodo groups.

The subject is any animal, preferably a mammal. In an embodiment, the subject is a human subject. In another embodiment, the subject is a mouse or a rat.

The administering can be performed according to techniques well known to those of skill in the art. In embodiments of this invention the administering comprises administering orally, rectally, transdermally, or parenterally.

In an embodiment the therapeutically effective amount is from about 1 mg to about 1000 mg, preferably from about 10 mg to about 100 mg.

Pharmaceutically acceptable salts and their preparation are well known to those of skill in the art. Examples of pharmaceutically acceptable salts are a hydrochloride salt, a mesylate salt, an ethylsulphonate salt, or a sulfate salt.

In an embodiment of this invention n is 1. In another embodiment n is 2.

This invention provides the above method wherein $R_1$ and $R_2$ are each independently hydrogen, fluoro, hydroxy, methyl or methoxy.

In an embodiment of this invention $R_3$ is hydrogen or methyl.

In an embodiment of this invention $R_4$ and $R_5$ are each independently hydrogen, or substituted or unsubstituted $C_1$–$C_{12}$ alkyl.

In an embodiment of this invention $R_4$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group. In preferred embodiments the lipophilic group is selected from the group consisting of piperazinyl, piperidinyl, morpholinyl, pyrrolidinyl, adamantyl, quinuclidinyl, and substituted derivatives thereof.

In another embodiment of this invention $R_5$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group. In preferred embodiments the lipophilic group is selected from the group consisting of piperazinyl, piperidinyl, morpholinyl, pyrrolidinyl, adamantyl, quinuclindyl, and substituted derivatives thereof.

This invention provides the above method wherein A is substituted or unsubstituted $C_1$–$C_{12}$ alkyl.

This invention provides the above method wherein Y is substituted or unsubstituted $C_1$–$C_{12}$ alkyl.

This invention provides the above method wherein $R_7$ is substituted or unsubstituted $C_1$–$C_{12}$ alkyl. In an embodiment $R_4$ is —C(O)—$R_6$, wherein $R_6$ is alkyl or $ANR_9R_{10}$, wherein A is alkyl, and $R_9$ and $R_{10}$ are each independently hydrogen, or substituted or unsubstituted $C_1$–$C_{12}$ alkyl. In another embodiment $R_5$ is —C(O)—$R_6$, wherein $R_6$ is alkyl or $ANR_9R_{10}$, wherein A is alkyl, and $R_9$ and $R_{10}$ are each independently hydrogen, or substituted or unsubstituted $C_1$–$C_{12}$ alkyl.

In an embodiment $R_4$ is —Y—C(O)—$R_7$, wherein Y is substituted or unsubstituted $C_1$–$C_{12}$ alkyl and $R_7$ is $NR_9R_{10}$. In another embodiment $R_5$ is —Y—C(O)—$R_7$, wherein Y is substituted or unsubstituted $C_1$–$C_{12}$ alkyl and $R_7$ is $NR_9R_{10}$.

In a specific embodiment of this invention $R_3$ and $NR_4R_5$ are in a cis spatial configuration. In another specific embodiment $R_3$ and $NR_4R_5$ are in a trans spatial configuration. The compound may also be a mixture of the cis and trans isomers.

In the method of this invention the compound may be a racemate of the R and S enantiomers. In a specific preferred embodiment the compound is an R enantiomer.

In a specific embodiment of this invention the compound is selected from the group consisting of 1-aminoindan, (R)-1-aminoindan, 1-aminotetralin, 1-aminobenzocyclobutane, 6-hydroxy-1-aminoindan, (R)-6-hydroxy-1-aminoindan, 7-hydroxy-1-aminoindan, 6-fluoro-1-aminoindan, (R)-6-fluoro-1-aminoindan, 5-methoxy-1-aminoindan, 7-methyl-1-aminoindan, 5-methyl-1-aminoindan, 4,5-dimethoxy-1-aminoindan, (R)-4,5-dimethoxy-1-aminoindan, (S)-4, 5-dimethoxy-1-aminoindan, 4-hydroxy-5-methoxy-1-aminoindan, 6-hydroxy-5-methoxy-1-aminoindan, trans -2-methyl-1-aminoindan, cis-2-methyl-1-aminoindan, 3,5, 7-trimethyl-1-aminoindan, N-methyl-1-aminoindan, (R)-N-methyl-1-aminoindan, N,N-dimethyl-1-aminoindan, N-formyl-1-aminoindan, (R)-N-formyl--aminoindan, N-acetyl-1-aminoindan, (R)-N-acetyl-1-aminoindan, N-acetyl-7 -methyl-1-aminoindan, N-acetyl-6-fluoro-1-aminoindan, (R)-N-acetyl-6-fluoro-1-aminoindan, 6-Methoxy-1-aminoindan, N-acetyl-6-methoxy-1-aminoindan, (R)-N-acetyl-4,5-dimethoxy-1-aminoindan, N-butyryl-1-aminoindan, N-benzyl-1-aminoindan, N-(4-aminobutanoyl)-1-aminoindan, N-(2-acetamido)-1-aminoindan, (R)-N-(2-acetamido)-1-aminoindan, N-(2-acetamido)-6-fluoro-1-aminoindan, N-(3-cyanopropyl)-1-aminoindan, N-(4-butanamido)-1-aminoindan, N-(2-acetamido)-1-aminotetralin, N,N-Di-(1-indanyl)amine, N-(2-N-Boc-aminoacetyl)-1-aminoindan, N-(2-Aminoacetyl)-1-aminoindan, N-Benzoyl-1-aminoindan, N-(2-n-Propylpentanoyl)-1-aminoindan, N-acetyl-6-nitro-1-aminiondan, 6-amino-N-acetyl-1-aminoindan, 6-acetamido-N-acetyl-1-aminoindan, cis-3-(methoxycarbonyl)-1-aminoindan, cis-1-aminoindan-3-carboxylic acid, trans-2-methyl-N-acetyl-1-aminoindan, cis-2-methyl-N-acetyl-1-aminoindan, (R)-N-trifluoroacetyl-1-aminoindan, N-(4-(di-n-propylsulfamoyl)benzoyl)-1-aminoindan, N-methyl-N-acetyl-1-aminoindan, (R)-N-methyl-N-acetyl-1-aminoindan, N-(2-proprionamido)-1-aminoindan, N-(2-phenylacetyl)-1-aminoindan, N-(m-anisoyl)-1-aminoindan, N-(4'-fluorobenzoyl)-1-aminoindan, N-(p-4-toluoyl)-1-aminoindan, N,N-di-(2-acetamido)-1-aminoindan, N-(1-indanyl)-aminoacetonitrile, 6-cyano-N-acetyl-1-aminoindan, 6-carboxamido-N-acetyl-1-aminoindan, 6-ethoxycarbonyl-N-acetyl-1-aminoindan, 2-(1-indanamino)-N-isopropylethanesulfonamide, 2-(1-indanamino)-N-(1-indanyl) ethanesulfonamide, (R,R)-2-(1-indanamino)-N-(1-indanyl)ethanesulfonamide, N,N'-bis-(1-indanyl)adipamide, N,N'-bis-(R)-(1-indanyl)adipamide, N,N'-bis-(R)-(1-indanyl) succinamide, and pharmaceutically acceptable acid addition salts thereof.

This invention provides the above method for treating Parkinson's disease in a subject. For treating Parkinson's disease in a subject the compound is preferably an R enantiomer.

The method of the present invention may involve the administration of any one of the compounds of formula 1 alone or in combination with conventional L-DOPA treatments. In combination treatments the compound of formula 1 may be administered before, after, or together with the conventional L-DOPA treatments.

This invention also provides the above method which further comprises administering to the subject a therapeutically effective amount of Levodopa. In a preferred embodiment the therapeutically effective amount of Levodopa is from about 50 mg to about 250 mg.

Another embodiment further comprises administering to the subject a therapeutically effective amount of decarboxylase inhibitor. The definition of a decarboxylase inhibitor, as well as the identity of specific decarboxylase inhibitors, is well known in the art to which this application pertains.

In a specific embodiment the decarboxylase inhibitor is L-Carbidopa. In an embodiment the therapeutically effective amount of L-Carbidopa is from about 10 mg to about 25 mg.

In a specific embodiment the decarboxylase inhibitor is benserazide. In an embodiment the therapeutically effective amount of benserazide is from about 12.5 mg to about 50 mg.

This invention provides the above method for treating dementia, epilepsy, convulsions, or seizures in a subject. In an embodiment the compound is an R enantiomer. In another embodiment the compound is an S enantiomer.

In a specific embodiment the compound is selected from the group consisting of (S)-1-aminoindan, (S)-6-fluoro-1-aminoindan, (S)-6-methoxy-1-aminoindan, (S)-4,5-dimethoxy-1-aminoindan, (S)-N-methyl-1-aminoindan, (R)-N-acetyl-1-aminoindan, (S)-N-acetyl-1-aminoindan, (S)-N-(2-acetamido)-1-aminoindan, N-formyl-1-aminoindan, (R)-N-formyl-1-aminoindan, (S)-N-formyl-1-aminoindan, (S)-(1-indanyl)-glycine, and pharmaceutically acceptable acid addition salts thereof.

This invention provides the above method for treating Parkinson's-type dementia. This invention also provides the above method for treating senile dementia in a subject. This invention also provides the above method for treating Alzheimer's-type dementia in a subject.

This invention provides a method for treating epilepsy, convulsions, or seizures in a subject comprising administering to the subject a therapeutically effective amount of a compound of the formula:

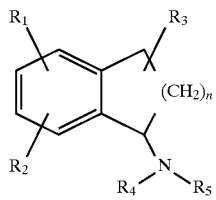

(Formula 1)

or a pharmaceutically acceptable salt thereof; wherein n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, halogen, nitro, NH—$R_3$, C(O)—$R_3$, or C(O)—$NR_9R_{10}$; $R_3$ is hydrogen, substituted or unsubstituted $C_1$–$C_4$ alkyl, hydroxy, substituted or unsubstituted $C_{1-4}$ alkoxy, or substituted or unsubstituted $C_6$–$C_{12}$ aryl; and $R_4$ and $R_5$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, alkynyl, —C(O)—$R_6$, —Y—C(O)—$R_7$, or Y—$(SO_2)NR_9R_{10}$;
wherein $R_6$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl, or A-$NR_9R_{10}$, wherein A is substituted or unsubstituted $C_1$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or $NR_9R_{10}$ wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl.

In a specific embodiment the subject is a human subject.
In an embodiment n is 1. In another embodiment wherein n is 2.

In an embodiment $R_1$ and $R_2$ are each independently hydrogen, fluoro, hydroxy, methyl or methoxy. In another embodiment $R_3$ is hydrogen or methyl.

This invention provides the above method wherein $R_4$ is propargyl. This invention also provides the above method wherein $R_5$ is propargyl.

In an embodiment $R_3$ and $NR_4R_5$ are in a cis spatial configuration. In another embodiment $R_3$ and $NR_4R_5$ are in a trans spatial configuration.

In a specific embodiment the compound is an R enantiomer.

In another embodiment the compound is an S enantiomer.
This invention provides the above method for treating epilepsy in a subject.

This invention also provides the above method for treating convulsions or seizures in a subject.

This invention provides a compound selected from the group consisting of 7-methyl-1-aminoindan, 5-methyl-1-aminoindan, (R)-6-hydroxy-1-aminoindan, 3,5,7-trimethyl-1-aminoindan, 4,5-dimethoxy-1-aminoindan, (R)-4,5-dimethoxy-1-aminoindan, (S)-4,5-dimethoxy-1-aminoindan, 4-hydroxy-5-methoxy-1-aminoindan, 6-hydroxy-5-methoxy-1-aminoindan, N-(4-aminobutanoyl)-1-aminoindan, (R)-N-formyl-1-aminoindan, (S)-N-formyl-1-aminoindan, (R)-N-acetyl-1-aminoindan, N-acetyl-7-methyl-1-aminoindan, N-acetyl-6-fluoro-1-aminoindan, (R)-N-acetyl-6-fluoro-1-aminoindan, (S)-6-Methoxy-1-aminoindan, N-acetyl-6-methoxy-1-aminoindan, (R)-N-acetyl-4,5-dimethoxy-1-aminoindan, N-(2-acetamido)-1-aminoindan, (R)-N-(2-acetamido)-1-aminoindan, (S)-N-(2-acetamido)-1-aminoindan, N-(2-acetamido)-6-fluoro-1-aminoindan, N-(3-cyanopropyl)-1-aminoindan, N-(2-acetamido)-1-aminotetralin, N-(2-N-Boc-aminoacetyl)-1-aminoindan, N-(2-Aminoacetyl)-1-aminoindan, N-Benzoyl-1-aminoindan, N-(2-n-Propylpentanoyl)-1-aminoindan, N-methyl-N-acetyl-1-aminoindan, (R)-N-methyl-N-acetyl-1-aminoindan, N-(2-propionamido)-1-aminoindan, N-(2-phenylacetyl)-1-aminoindan, N-(m-anisoyl)-1-aminoindan, N-(4'-fluorobenzoyl)-1-aminoindan, N-(p-4-toluoyl)-1-aminoindan, (S)-(1-indanyl)-glycine, N,N-di-(2-acetamido)-1-aminoindan, N-(1-indanyl)-aminoacetonitrile 6-cyano-N-acetyl-1-aminoindan, 6-carboxamido-N-acetyl-1-aminoindan, 6-ethoxycarbonyl-N-acetyl-1-aminoindan, 2-(1-indanamino)-N-isopropylethanesulfonamide, 2-(1-indanamino)-N-(1-indanyl)ethanesulfonamide, (R,R)-2-(1-indanamino)-N-(1-indanyl)ethanesulfonamide, N-(4-(di-n-propylsulfamoyl)benzoyl)-1-aminoindan, N,N'-bis-(1-indanyl)adipamide, N,N'-bis-(R)-(1-indanyl)adipamide, N,N'-bis(R)-(1-indanyl)succinamide, trans-2-methyl-N-acetyl-1-aminoindan, cis-2-methyl-N-acetyl-1-aminoindan, and salts thereof.

For those above-listed compounds where no indication as to the nature of the isomerism is given, this invention provides for the racemic mixture, the R enantiomer, and the S enantiomer.

In an embodiment the salt is a hydrochloride salt, a mesylate salt, an ethylsulfonate salt, or a sulfate salt.

This invention also provides a pharmaceutical composition comprising a therapeutically effective amount of the above-listed compounds and a pharmaceutically acceptable carrier.

This invention provides for the pharmaceutical composition the pharmaceutically acceptable carrier is a solid and the pharmaceutical composition is a tablet. In an embodiment the therapeutically effective amount is from about 1 mg to about 1000 mg. In a more specific embodiment the therapeutically effective amount is from about 10 mg to about 100 mg.

In another embodiment of the pharmaceutical composition the pharmaceutically acceptable carrier is a liquid and the pharmaceutical composition is an injectable solution. In a specific embodiment the therapeutically effective amount is from about 1 mg/ml to about 1000 mg/ml. In a more specific embodiment the therapeutically effective amount is from about 10 mg/ml to about 100 mg/ml. In an embodiment of the pharmaceutical composition the carrier is a gel and the pharmaceutical composition is a suppository.

This invention further provides for the above pharmaceutical composition, further comprising a therapeutically effective amount of Levodopa.

This invention also provides for an embodiment of the pharmaceutical composition further comprising a therapeutically effective amount of a decarboxylase inhibitor.

In a specific embodiment the decarboxylase inhibitor is L-Carbidopa. In a specific embodiment of the pharmaceutical composition the effective amount of the compound is from about 1 mg to about 1000 mg, the therapeutically effective amount of Levodopa is from about 50 mg to about 250 mg, and the therapeutically effective amount of L-Carbidopa is from about 10 mg to about 25 mg.

In an embodiment of the pharmaceutical composition the decarboxylase inhibitor is benserazide. In a specific embodiment the therapeutically effective amount of the compound is from about 1 mg to about 1000 mg, the therapeutically effective amount of. Levodopa is from about 50 mg to about 200 mg, and the therapeutically effective amount of benserazide is from about 12.5 mg to about 50 mg.

The compounds of general formula 1 possess neuroprotective activity. Accordingly, this invention provides a method for treating acute neurological traumatic disorder or neurotrauma in a subject comprising administering to the subject a therapeutically effective amount of a compound of the formula:

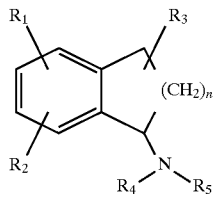

(Formula 1)

or a pharmaceutically acceptable salt thereof; wherein n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, halogen, nitro, amino, NH—$R_3$ or C(O)—$R_3$, or C(O)—$NR_9R_{10}$; $R_3$ is hydrogen, substituted or unsubstituted $C_1$–$C_4$ alkyl, hydroxy, substituted or unsubstituted $C_{1-4}$ alkoxy, or substituted or unsubstituted $C_{6-12}$ aryl; and $R_4$ and $R_5$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, —C(O)—$R_6$, —Y— C(O) —$R_7$, or Y—(SO$_2$)$NR_9R_{10}$; wherein $R_6$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl, or A—$NR_9R_{10}$, wherein A is substituted or unsubstituted $C_7$–$C_{12}$ alkyl, substituted or unsubstituted $C_6$–$C_{12}$ aryl, substituted or unsubstituted $C_7$–$C_{12}$ aralkyl, and $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl; Y is substituted or unsubstituted $C_1$–$C_{12}$ alkyl, substituted or unsubstituted $C_6$–$C_{12}$ aryl or substituted or unsubstituted $C_7$–$C_{12}$ aralkyl, and $R_7$ is hydrogen, hydroxy, substituted or unsubstituted $C_1$–$C_{12}$ alkyl, substituted or unsubstituted $C_6$–$C_{12}$ aryl, substituted or unsubstituted $C_7$–$C_{12}$ aralkyl or $NR_9R_{10}$, wherein $R_9$ and $R_{10}$ are each independently hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or indanyl.

The subject is any animal, preferably a mammal. In an embodiment, the subject is a human subject. In another embodiment, the subject is a mouse or a rat.

The administering can be performed according to techniques well known to those of skill in the art. In embodiments of this invention the administering comprises administering orally, rectally, transdermally, or parenterally.

In an embodiment the therapeutically effective amount is from about 1 mg to about 1000 mg, preferably from about 10 mg to about 100 mg.

Pharmaceutically acceptable salts and their preparation are well known to those of skill in the art. Examples of pharmaceutically acceptable salts are a hydrochloride salt, a mesylate salt, an esylate salt, or a sulfate salt.

In an embodiment of this invention n is 1. In another embodiment n is 2.

This invention provides the above method wherein $R_1$ and $R_2$ are each independently hydrogen, fluoro, hydroxy, methyl or methoxy. In a specific embodiment $R_1$ is 4-fluoro, 6-fluoro, 4-hydroxy, 6-hydroxy, 4-methyl, 6-methyl, 4-methoxy, or 6-methoxy. In another embodiment $R_2$ is 4-fluoro, 6-fluoro, 4-hydroxy, 6-hydroxy, 4-methyl, 6-methyl, 4-methoxy, or 6-methoxy.

In an embodiment of this invention $R_3$ is hydrogen or methyl.

In an embodiment of this invention $R_4$ and $R_5$ are each independently hydrogen, or substituted or unsubstituted $C_1$–$C_{12}$ alkyl.

In an embodiment of this invention $R_4$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group. In preferred embodiments the lipophilic group is selected from the group consisting of piperazinyl, piperidinyl, morpholinyl, pyrrolidinyl, adamantyl, quinuclindyl, and substituted derivatives thereof.

In another embodiment of this invention $R_5$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group. In a preferred embodiments the lipophilic group is selected from the group consisting of piperazinyl, piperidinyl, morpholinyl, pyrrolidinyl, adamantyl, quinuclindyl, and substituted derivatives thereof.

This invention provides the above method wherein A is substituted or unsubstituted $C_1-C_{12}$ alkyl.

This invention provides the above method wherein Y is substituted or unsubstituted $C_1-C_{12}$ alkyl.

This invention provides the above method wherein $R_7$ is substituted or unsubstituted $C_1-C_{12}$ alkyl.

In an embodiment $R_4$ is —C(O)—$R_6$, wherein $R_6$ is alkyl or $ANR_9R_{10}$, wherein A is alkyl, and $R_9$ and $R_{10}$ are each independently hydrogen, or substituted or unsubstituted $C_1-C_{12}$ alkyl. In another embodiment $R_5$ is —C(O)—$R_6$, wherein $R_6$ is alkyl or $ANR_9R_{10}$, wherein A is alkyl, and $R_9$ and $R_{10}$ are each independently hydrogen, or substituted or unsubstituted $C_1-C_{12}$ alkyl.

In an embodiment $R_4$ is —Y—C(O)—$R_7$, wherein Y is substituted or unsubstituted $C_1-C_{12}$ alkyl and $R_7$ is $NR_9R_{10}$.

In another embodiment $R_5$ is —Y—C(O)—$R_7$, wherein Y is substituted or unsubstituted $C_1-C_{12}$ alkyl and $R_7$ is $NR_9R_{10}$.

In a specific embodiment of this invention $R_3$ and $NR_4R_5$ are in a cis spatial configuration. In another specific embodiment $R_3$ and $NR_4R_5$ are in a trans spatial configuration. The compound may also be a mixture of the cis and trans isomers.

In a specific embodiment the compound is an R enantiomer. In another embodiment the compound is an S enantiomer.

In an embodiment of the above method the compound is selected from the group consisting of 1-aminoindan, (R)-1-aminoindan, (S)-1-aminoindan, 1-aminotetralin, 1-aminobenzocyclobutane, 6-hydroxy-1-aminoindan, (R)-6-hydroxy-1-aminoindan, 6-fluoro-1-aminoindan, (R)-6-fluoro-1-aminoindan, (S)-6-fluoro-1-aminoindan, 5-methoxy-1-aminoindan, (S)-6-methoxy-1-aminoindan, 7-methyl-1-aminoindan, 5-methyl-1-aminoindan, 4,5-dimethoxy-1-aminoindan, (R)-4,5-dimethoxy-1-aminoindan, (S)-4,5-dimethoxy-1-aminoindan, 4-hydroxy-5-methoxy-1-aminoindan, 6-hydroxy-5-methoxy-1-aminoindan, trans-2-methyl-1-aminoindan, cis-2-methyl-1-aminoindan, 3,5,7-trimethyl-1-aminoindan, N-methyl-1-aminoindan, (R)-N-methyl-1-aminoindan, (S)-N-methyl-1-aminoindan, N,N-dimethyl-1-aminoindan, N-formyl-1-aminoindan, (R)-N-formyl-1-aminoindan, (S)-N-formyl-1-aminoindan, N-acetyl-1-aminoindan, (R)-N-acetyl-1-aminoindan, (S)-N-acetyl-1-aminoindan, N-acetyl-7-methyl-1-aminoindan, N-acetyl-6-fluoro-1-aminoindan, (R)-N-acetyl-6-fluoro-1-aminoindan, 6-Methoxy-1-aminoindan, (S)-6-Methoxy-1-aminoindan, N-acetyl-6-methoxy-1-aminoindan, (R)-N-acetyl-4,5-dimethoxy-1-aminoindan, N-butyryl-1-aminoindan, N-benzyl-1-aminoindan, N-(4-aminobutanoyl)-1-aminoindan, N-(2-acetamido)-1-aminoindan, (R)-N-(2-acetamido)-1-aminoindan, N-(2-acetamido)-6-fluoro-1-aminoindan, N-(3-cyanopropyl)-1-aminoindan, N-(4-butanamido)-1-aminoindan, (S)-N-(2-acetamido)-1-aminoindan, N-(2-acetamido)-1-aminotetralin, N,N-Di-(l-indanyl)amine, N-(2-N-Boc-aminoacetyl)-1-aminoindan, N-(2-Aminoacetyl)-1-aminoindan, N-Benzoyl-1-aminoindan, N-(2-n-Propylpentanoyl)-1-aminoindan, N-acetyl-6-nitro-1-aminiondan, 6-amino-N-acetyl-1-aminoindan, 6-acetamido-N-acetyl-1-aminoindan, cis-3-(methoxycarbonyl)-1-aminoindan, cis-1-aminoindan-3-carboxylic acid, trans-2-methyl-N-acetyl-1-aminoindan, cis-2-methyl-N-acetyl-1-aminoindan, (R)-N-trifluoroacetyl-1-aminoindan, N-(4-(di-n-propylsulfamoyl)benzoyl)-1-aminoindan, N-methyl-N-acetyl-1-aminoindan, (R)-N-methyl-N-acetyl-1-aminoindan, N-(2-proprionamido)-1-aminoindan, N-(2-phenylacetyl)-1-aminoindan, N-(m-anisoyl)-1-aminoindan, N-(4'-fluorobenzoyl)-1-aminoindan, N-(p-4-toluoyl)-1-aminoindan, (S)-(1-indanyl)-glycine, N,N-di-(2-acetamido)-1-aminoindan, N-(1-indanyl)-aminoacetonitrile, 6-cyano-N-acetyl-1-aminoindan, 6-carboxamido-N-acetyl-1-aminoindan, 6-ethoxycarbonyl-N-acetyl-1-aminoindan, 2-(1-indanamino)-N-isopropylethanesulfonamide, 2-(1-indanamino)-N-(1-indanyl) ethanesulfonamide, (R,R)-2-(1-indanamino)-N-(l-indanyl)ethanesulfonamide, N,N'-bis-(1-indanyl)adipamide, N,N'-bis-(R)-(1-indanyl)adipamide, N,N'-bis-(R)-(1-indanyl)succinamide, and pharmaceutically acceptable acid addition salts thereof.

This invention provides the above method for treating acute neurological traumatic disorder in a subject.

This invention provides the above method for treating neurotrauma in a subject. In a still more specific embodiment the neurotrauma is caused by a closed head injury.

The subject invention further provides a method of treating a subject afflicted with a memory disorder which comprises administering to the subject an amount of a compound of general formula 1 or the pharmaceutically acceptable salt thereof of the subject invention effective to treat the memory disorder in the subject.

The subject invention further provides a method of treating a subject afflicted with dementia which comprises administering to the subject an amount of a compound of general formula 1 or the pharmaceutically acceptable salt thereof of the subject invention effective to treat dementia in the subject. In one embodiment, the dementia is of the Alzheimer type (DAT).

The subject invention further provides a method of treating a subject afflicted with depression which comprises administering to the subject an amount of a compound of general formula 1 or the pharmaceutically acceptable salt thereof of the subject invention effective to treat depression in the subject.

The subject invention further provides a method of treating a subject afflicted with hyperactive syndrome which comprises administering to the subject an amount of a compound of general formula 1 or the pharmaceutically acceptable salt thereof of the subject invention effective to treat hyperactive syndrome in the subject.

The administering may comprise orally administering, rectally administering, or parenterally administering.

The subject invention further provides a method of treating a subject afflicted with an affective illness which comprises administering to the subject an amount of a compound of general formula 1 or the pharmaceutically acceptable salt thereof of the subject invention effective to treat the affective illness in the subject.

The subject invention further provides a method of treating a subject afflicted with a neurodegenerative disease which comprises administering to the subject an amount of a compound of general formula 1 or the pharmaceutically acceptable salt thereof of the subject invention effective to treat the neurodegenerative disease in the subject.

The subject invention further provides a method of treating a subject afflicted with a neurotoxic injury which comprises administering to the subject an amount of a compound of general formula 1 or the pharmaceutically acceptable salt thereof of the subject invention effective to treat the neurotoxic injury in the subject.

The subject invention further provides a method of treating a subject afflicted with brain ischemia which comprises administering to the subject an amount of a compound of general formula 1 or the pharmaceutically acceptable salt thereof of the subject invention effective to treat brain ischemia in the subject.

The subject invention further provides a method of treating a subject afflicted with a head trauma injury which comprises administering to the subject an amount of a compound of general formula 1 or the pharmaceutically acceptable salt thereof of the subject invention effective to treat the head trauma injury in the subject.

The subject invention further provides a method of treating a subject afflicted with a spinal trauma injury which comprises administering to the subject an amount of a compound of general formula 1 or the pharmaceutically acceptable salt thereof of the subject invention effective to treat the spinal trauma injury in the subject.

The subject invention further provides a method of treating a subject afflicted with schizophrenia which comprises administering to the subject an amount of a compound of general formula 1 or the pharmaceutically acceptable salt thereof of the subject invention effective to treat schizophrenia in the subject.

The subject invention further provides a method of treating a subject afflicted with an attention deficit disorder which comprises administering to the subject an amount of a compound of general formula 1 or the pharmaceutically acceptable salt thereof of the subject invention effective to treat the attention deficit disorder in the subject.

The subject invention further provides a method of treating a subject afflicted with multiple sclerosis which comprises administering to the subject an amount of a compound of general formula 1 or the pharmaceutically acceptable salt thereof of the subject invention effective to treat multiple sclerosis in the subject.

The subject invention further provides a method of preventing nerve damage in a subject which comprises administering to the subject an amount of general formula 1 or the pharmaceutically acceptable salt thereof of the subject invention effective to prevent nerve damage in the subject.

In one embodiment, the nerve damage is structural nerve damage. In another embodiment, the structural nerve damage is optic nerve damage.

The subject invention further provides a method of treating a subject suffering from symptoms of withdrawal from an addictive substance which comprises administering to the subject an amount of a compound of general formula 1 or the pharmaceutically acceptable salt thereof of the subject invention effective to treat the symptoms of withdrawal in the subject.

As used herein, the term "symptoms of withdrawal" refers to physical and/or psychological symptoms, including drug craving, depression, irritability, anergia, amotivation, appetite change, nausea, shaking and sleep irregularity.

As used herein, the term "addictive substance" includes, by way of example, (a) addictive opiates such as opium, heroin and morphine, (b) psychostimulants such as cocaine, amphetamines and methamphetamines, (c) alcohol, (d) nicotine, (e) barbiturates and (f) narcotics such as fentanyl, codeine, diphenoxylate and thebaine.

In one embodiment, the addictive substance is cocaine. In another embodiment, the addictive substance is alcohol.

This invention provides a method for preparing an optically active enantiomer of a compound of the formula:

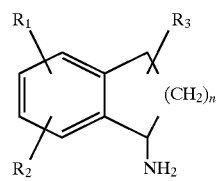

(Formula 2)

wherein the enantiomer is optically active at the $C_1$ position; n is 0, 1 or 2; $R_1$ and $R_2$ are each independently hydrogen, hydroxy, substituted or unsubstituted $C_1$–$C_4$ alkyl, substituted or unsubstituted $C_1$–$C_4$ alkoxy, or halogen; and $R_3$ is hydrogen or unsubstituted $C_1$–$C_4$ alkyl;

comprising incubating in a reaction mixture a racemic N-benzyl analog of the compound with an optically active enantiomer of mandelic acid;

converting the optically active ammonium salt obtained to its corresponding optically active base;

and reducing the base to the optically active enantiomer of the compound.

It is preferred that the racemic N-benzyl analog is reacted with the optically active enantiomer of mandelic acid in a solvent. Suitable solvents include ethanol; ethanol and acetone; and ethanol and acetylacetate, as well as other solvents that can be identified by one of ordinary skill in the art. Most preferably, the solvent is ethanol.

In a preferred embodiment, the optically active salt is isolated prior to its conversion to its corresponding optically active base.

In an embodiment, the reaction mixture of the mandelic acid and the racemic N-benzyl analog is heated prior to the isolation of the salt until complete dissolution of the reactants is observed, and then cooled. Preferably, the reaction mixture is heated to a temperature from about 68° C. to about 78° C., preferably about 75° C., and then cooled over a period of several hours to a temperature from about 5° C. to about 20° C., preferably about 10° C.

It is also preferable that the isolated optically active salt is recrystallized prior to its conversion to its corresponding base.

Preferably, the optically active salt is converted to its corresponding base by the addition of a basic reagent. In a more specific embodiment, the basic reagent is an organic or inorganic base. Suitable bases include sodium hydroxide, sodium carbonate, potassium hydroxide, potassium carbonate and triethylamine, as well as other suitable bases that can be identified by one of skill in the art. Preferably the base is sodium hydroxide.

Preferably, the optically active salt is suspended in a mixture of water and a water immiscible solvent, such as toluene, prior to the addition of the basic reagent. Preferably, the toluene:water ratio is about 75:70.

Preferably, the optically active base is isolated prior to its reduction to the optically active enantiomer of the compound. Any known system for performing reduction may be used. In an embodiment, the optically active base is reduced by reaction with hydrogen gas in the presence of a palladium/carbon catalyst, preferably under increased pressure.

It is preferred that n is 1, and $R_1$, $R_2$ and $R_3$ are hydrogen. In such an instant the optically active salt is R(+) or S(−)-N-benzyl-1-aminoindan-mandelate ethanolate and the optically active base is R-(+) or S-(−)-N-benzyl-1-aminoindan.

In one embodiment, the optically active enantiomer of mandelic acid is L-(+)-mandelic acid, the optically active salt is R-(+)-N-benzyl-1-aminoindan-mandelate ethanolate, and the optically active base is R-(+)-N-benzyl-1-aminoindan.

In another embodiment, the optically active enantiomer of mandelic acid is D-(-)mandelic acid, the optically active salt is S-(-)-N-benzyl-1-aminoindan-mandelate ethanolate, and the optically active base is S-(-)-N-benzyl-1-aminoindan.

This invention provides method for preparing an optically active mandalate salt of a compound of the formula:

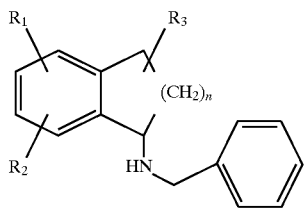

(Formula 3)

wherein the salt is optically active at the $C_1$ position; n is 0, 1, or 2; $R_1$, $R_2$, and $R_3$ are each independently hydrogen, hydroxy, substituted or unsubstituted $C_1$–$C_4$ alkyl, substituted or unsubstituted $C_1$–$C_4$ alkoxy, or halogen; and $R_3$ is hydrogen, or unsubstituted $C_1$–$C_4$ alkyl; comprising reacting a racemic mixture of the compound with an optically active enantiomer of mandelic acid, and recovering the optically active mandelate salt. In an embodiment, n is 1; and $R_1$, $R_2$ and $R_3$ are hydrogen.

This invention further provides a method for preparing an optically active free base of the formula:

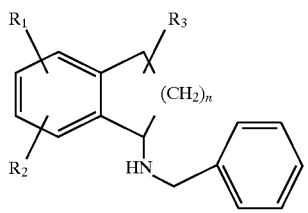

(Formula 3)

comprising converting the optically active mandalate salt from the above-described method to its corresponding optically active base. This invention also provides R-(+)-N benzyl-1-aminoindan and S-(-)-N-benzyl-1-aminoindan, when prepared in accordance with this method.

This invention provides R-(+)-N-benzyl-1-aminoindan, R-(+)-N-benzyl-1-aminoindan-L-mandelate ethanolate, and S-(-)-N-benzyl-1-aminoindan-D-mandelate ethanolate.

This invention provides a method for preparing racemic N-benzyl-1-aminoindan comprising reacting 1-chloroindane with benzylamine in an inert solvent. Preferably, the 1-chloroindane and benzylamine are combined at a temperature of about 90° C. It is also preferable that the temperature is raised to about 115° C. for a period of about ten hours following the combining of the 1-chlorindane with the benzylamine. This invention provides N-benzyl-1-aminoindan when prepared in accordance with the above-described method.

This invention will be better understood from the Experimental Details which follow. However, one skilled in the art will readily appreciate that the specific methods and results discussed are merely illustrative of the invention as described more fully in the claims which follow thereafter.

Experimental Details

A. Synthesis of Compounds
Preparation of 1-Aminoindans

The R-1-aminoindan starting material can be prepared by methods known in the art which include, by way of example, the method of Lawson and Rao, Biochemistry, 19, 2133 (1980), methods in references cited therein, and the method of European Patent No. 235,590.

R-1-aminoindan can also be prepared by resolution of a racemic mixture of the R and S enantiomers, which involves, for example, the formation of diastereomeric salts with chiral acids, or any other known method such as those reported in J. Jacques, et al., ibid. Alternatively, R-1-aminoindan may be prepared by reacting 1-indanone with an optically active amine, followed by reduction of the carbon nitrogen double bond of the resulting imine by hydrogenation over a suitable catalyst, such as palladium on carbon, platinum oxide or Raney nickel. Suitable optically active amines include, for example, one of the antipodes of phenethylamine or an ester of an amino acid, such as valine or phenylalanine. The benzylic N—C bond may be cleaved subsequently by hydrogenation under non-vigorous conditions.

An additional method for preparing R-1-aminoindan is the hydrogenation of indan-1-one oxime ethers as described above, wherein the alkyl portion of the ether contains an optically pure chiral center. Alternatively, a non-chiral derivative of indan-1-one containing a carbon-nitrogen double bond, such as an imine or oxime, can be reduced with a chiral reducing agent, e.g., a complex of lithium aluminum-hydride and ephedrine.

Resolution of Enantiomers

The R- and S- enantiomers of each compound may be obtained by optical resolution of the corresponding racemic mixtures. Such a resolution can be accomplished by any conventional resolution method well known to a person skilled in the art, such as those described in U.S. Pat. No. 4,833,273, issued May 23, 1989 (Goel) and in J. Jacques, A. Collet and S. Wilen, "Enantiomers, Racemates and Resolutions," Wiley, N.Y. (1981). For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired R enantiomer.

The racemic mixture of R and S enantiomers of N-propargyl-1-aminoindan (PAI) may be prepared, for example, as described in GB 1,003,676 and GB 1,037,014. The racemic mixture of PAI can also be prepared by reacting 1-chloroindan with propargylamine. Alternatively, this racemate may be prepared by reacting propargylamine with 1-indanone to form the corresponding imine, followed by reduction of the carbon-nitrogen double bond of the imine with a suitable agent, such as sodium borohydride.

The 1-aminoindans of general formula 1 where $R_1$ and $R_2$ are as indicated and $R_4$ and $R_5$ are hydrogen may be prepared by the chemical reduction of the relevant oximes, by means of zinc/acetic acid or by catalytic hydrogenation. The oximes may be prepared by reaction of the corresponding indan-1-ones with hydroxylamine hydrochloride. The indan-1-ones may be prepared by Friedal-Crafts cyclization of substituted dihydrocinnamic acids or the corresponding chlorides using aluminum trichloride or other Lewis acids, such as polyphosphoric acid or methanesulphonic acid as condensing agents, for example according to procedures described in J. Org. Chem. 46, 2974 (1981) and in J. Chem. Soc. Perkin Trans, 1, 151 (1972).

N-methyl-1-aminoindan may be prepared from 1-aminoindan according to the procedure described in J.Med.Chem.9, 830 (1966).

N,N-dimethyl-1-aminoindan may be prepared from 1-aminoindan according to the procedure described in Yakugaku Zasshi, 82 1597 (1962)—Chem. Abs. 59 611f.

N-formyl and N-acyl derivatives of 1-aminoindan and 1-aminotetralin may be prepared from the corresponding 1-aminoindan or 1-aminotetralin using the methods described in J.Med.Chem. 9, 830 (1966), J.Chromatog. 502, 154 (1990) or Boll.Chim.Farm. 115, 489 (1976).

The compounds of general formula 1, where $R_4$ is hydrogen or lower alkyl and $R_5$ is C(O)—$R_6$, and $R_6$ is A-NR$_9$R$_{10}$ are indanylamides of amino acids, and may be prepared by procedures known to those skilled in the art, for example, by reacting the aminoindan with an activated form of the amino acid in the presence or absence (as necessary) of acylation catalysts such as 4-N,N-dimethylaminopyridine.

Thus the aminoindan is reacted with an amino acid anhydride having the amino terminus protected by a suitable radical such as t-butoxycarbonyl (Boc), in the presence of for example DMAP, in an aprotic organic solvent such as THF, at a temperature within the range of 0°–50° C., preferably from 25°–40 C., for a period of from 1-24 hours, preferably from 5–10 hours.

Alternatively, the 1-aminoindan may be reacted with an N-hydroxy succinimide ester of an amino acid having the terminal amino group protected as above, in an aprotic solvent such as 1,2-dimethoxyethane (DME), at a temperature within the range of 0°–70° C., preferably from 25°–50° C., for a period of from 12–48 hours, preferably 24–36 hours.

The product may be purified by column chromatography and/or by crystallization. Removal of the protecting group may be accomplished by subjecting said group to acidic conditions for example to hydrochloric acid or trifluoroacetic acid in a suitable organic solvent such as isopropanol or dioxane. The desired products are then obtained as their acid addition salts.

The compounds of general formula 1 wherein $R_1$ or $R_2$ are hydrogen or lower alkyl, $R_4$ is hydrogen and $R_5$ is Y—C(O)—$R_7$ and $R_7$ is NR$_9$R$_{10}$, are N-indanyl derivatives of amino acid amides, and may be prepared by reacting the relevant amino acid amide with a 1-halogeno-indan or with a 1-indanone. In the latter case, the resulting Schiff base is further reduced, by a suitable reducing agent such as sodium borohydride, to afford the desired amine.

Alternatively these compounds may be prepared by reacting the 1-aminoindan with an omega-halogeno derivative of the relevant amino acid amide, in an alcoholic solvent such as ethanol in the presence of a base such as potassium carbonate, at a temperature within the range of 50°–100° C., preferably at the reflux temperature of the solvent, for a period of from 12–36 hours, preferably 24 hours. The product may then be converted into its acid addition salt. The R and S enantiomers of each of these compounds may be resolved using procedures known to those skilled in the art.

The following list provides an Example number, a European Patent Application number or a Chemical Abstracts Registry Number for some of the compounds of general formula 1 that are of interest in the present invention. A Chem. Abs. number with an asterisk indicates the number of a closely related compound.

1-aminoindan, EP 436492 34698-41-4*
    (R)-1-aminoindan, 10305-73-4
    (S)-1-aminoindan, 32457-23-1
    1-aminotetralin, 49800-23-9
    1-aminobenzocyclobutene, EXAMPLE 27
    6-hydroxy-1-aminoindan, EXAMPLE 34
    (R)-6-hydroxy-1-aminoindan, EXAMPLE 35
    7-hydroxy-1-aminoindan, EXAMPLE 42 EP 173 331
    6-fluoro-1-aminoindan, EP 538 134
    (R)-6-fluoro-1-aminoindan, EP 538 134
    (S)-6-fluoro-1-aminoindan, EP 538 134

5-methyl-1-aminoindan, EXAMPLE 38
5-methoxy-1-aminoindan, EXAMPLE 36 41566-77-6
6-methoxy-1-aminoindan, EXAMPLE 25 103028-80-4
(S)-6-methoxy-1-aminoindan, EXAMPLE 24
7-methyl-1-aminoindan, EXAMPLE 28
3,5,7-trimethyl-1-aminoindan, EXAMPLE 41
4,5-dimethoxy-1-aminoindan, EXAMPLE 31
(R)-4,5-dimethoxy-1-aminoindan, EXAMPLE 29
(S)-4,5-dimethoxy-1-aminoindan, EXAMPLE 30
4-hydroxy-5-methoxy-1-aminoindan, EXAMPLE 33
6-hydroxy-5-methoxy-1-aminoindan, EXAMPLE 32
trans-2-methyl-1-aminoindan EXAMPLE 39 13943-76-6 *
cis-2-methyl-1-aminoindan, EXAMPLE 40 13943-41-4 *
N-methyl-1-aminoindan, EXAMPLE 12 90874-50-3
(R)-N-methyl-1-aminoindan, EXAMPLE 13 10277-78-7 *
(S)-N-methyl-1-aminoindan, EXAMPLE 14 68533-22-2
N,N-dimethyl-1-aminoindan, EXAMPLE 15 10277-80-2 *
N-formyl-1-aminoindan, EXAMPLE 8 10277-75-5
(R)-N-formyl-1-aminoindan, EXAMPLE 9
(S)-N-formyl-1-aminoindan, EXAMPLE 10
N-acetyl-1-aminoindan, EXAMPLE 17 127761-17-5
(R)-N-acetyl-1-aminoindan, EXAMPLE 18 71744-38-2 *
(S)-N-acetyl-1-aminoindan, EXAMPLE 19 61899-41-0
N-acetyl-7-methyl-1-aminoindan, EXAMPLE 20
N-acetyl-6-methoxy-1-aminoindan, EXAMPLE 26
N-acetyl-6-fluoro-1-aminoindan, EXAMPLE 22
(R)-N-acetyl-6-fluoro-1-aminoindan, EXAMPLE 23
(R)-N-acetyl-4,5-dimethoxy-1-aminoindan, EXAMPLE 21
N-butyryl-1-aminoindan, EXAMPLE 11 144602-65-3
N-benzyl-1-aminoindan, EXAMPLE 16 66399-68-6 *
N-benzoyl-1-aminoindan, EXAMPLE 46
N-(4-aminobutyryl)-1-aminoindan, EXAMPLE 7
N-(2-acetamido)-1-aminoindan, EXAMPLE 3
(R)-N-(2-acetamido)-1-aminoindan, EXAMPLE 1
(S)-N-(2)acetamido)-1-aminoindan, EXAMPLE 2
N-(2-acetamido)-6-fluoro-1-aminoindan, EXAMPLE 5
N-(2-acetamido)-1-aminotetralin, EXAMPLE 4
N-(2-aminoacetyl)-1-aminoindan, EXAMPLE 45
N-(3-cyanopropyl)-1-aminoindan, EXAMPLE 37
N,N-di-(1-indanyl)amine EXAMPLE 43 113535-01-6 *
N-(2-n-Propylpentanoyl)-1-aminoindan EXAMPLE 47
N-methyl-N-acetyl-1-aminoindan, EXAMPLE 48
(R)-N-methyl-N-acetyl-1-aminoindan, EXAMPLE 49
N-(2-propionamido)-1-aminoindan, EXAMPLE 50
N-(2-phenylacetyl)-1-aminoindan, EXAMPLE 51 EP488, 616
N-(m-anisoyl)-1-aminoindan, EXAMPLE 52
N-(4'-fluorobenzoyl)-1-aminoindan, EXAMPLE 53
N-(p-4-toluoyl)-1-aminoindan, EXAMPLE 54
(S)-(1-indanyl)-glycine, EXAMPLE 55
N,N-di-(2-acetamido)-1-aminoindan, EXAMPLE 56
N-(1-indanyl)-aminoacetonitrile EXAMPLE 57
N-acetyl-6-nitro-1-aminoindan, EXAMPLE 58

6-amino-N-acetyl-1-aminoindan, EXAMPLE 59
6-acetamido-N-acetyl-1-aminoindan, EXAMPLE 60
6-cyano-N-acetyl-1-aminoindan, EXAMPLE 61
6-carboxamido-N-acetyl-1-aminoindan, EXAMPLE 62
6-ethoxycarbonyl-N-acetyl-1-aminoindan, EXAMPLE 63
cis-3-(methoxycarbonyl)-1-aminoindan, EXAMPLE 64
cis-1-aminoindan-3-carboxylic acid, EXAMPLE 65
trans-2-methyl-N-acetyl-1-aminoindan, EXAMPLE 66
cis-2-methyl-N-acetyl-1-aminoindan, EXAMPLE 67
(R)-N-trifluoroacetyl-1-aminoindan, EXAMPLE 68
N-(4-(di-n-propylsulfamoyl)benzoyl)-1-aminoindan, EXAMPLE 69
2-(1-indanamino)-N-isopropylethanesulfonamide, EXAMPLE 70
2-(1-indanamino)-N-(1-indanyl)ethanesulfonamide, EXAMPLE 71
(R,R)-2-(1-indanamino)-N-(1-indanyl)ethanesulfonamide, EXAMPLE 72
N,N'-bis-(1-indanyl)adipamide, EXAMPLE 73
N,N'-bis-(R)-(1-indanyl)adipamide, EXAMPLE 74
N,N'-bis-(R)-(1-indanyl)succinamide, EXAMPLE 75

The following examples provide additional data relating to specific compounds of this invention.

EXAMPLE 1

(R)-N-(2-Acetamido)-1-aminoindan.HCl

A mixture of (R)-1-aminoindan (5.5 g, 40.7 mmole), 2-chloro-acetamide (3.7 g, 39.6 mmole), sodium bicarbonate (3.7 g, 44 mmole) and absolute ethanol (80 ml) was stirred under reflux for 24 hr. The reaction mixture was then filtered hot, the filtrate ice-cooled for 1 hr, and filtered. The solid was collected and. washed with ether. The crude product was dissolved in isopropanol (135 ml), and 25% w/v isopropanolic HCl (6.5 ml, 44 mmole) was added; the mixture was stirred for 3 hr under ice cooling and filtered. The solid was washed with ether/hexane (5:1, 50 ml) and dried to afford 3.4 g (37%), m.p.: 224°–5° C.

$^1$H NMR δ (DMSO): 9.60 (br s, 2H, NH$_2^+$), 8.04, 7.58 (s, 2H, CONH$_2$), 7.70 (d, 1H, Ph), 7.34 (m, 3H, Ph), 4.80 (br s, 1H, C1-H), 3.62 (m, 1H, CH$_2$), 3.14 (m, 1H, C3-H), 2.84 (m, 1H, C3-H'), 2.38 (m, 1H, C2-H), 2.23 (m, 1H, C2-H') ppm.

MS: 191 (MH$^+$, 58), 117 (100).

IR (KBr): 3391, 3252, 3193, 2947, 2807, 1692, 1616, 1559, 1443, 1381, 1339 cm$^{-1}$.

EXAMPLE 2

(S)-N-(2-Acetamido)-1-aminoindan.HCl

The title compound was obtained from (S)-1-aminoindan in a manner analogous to that described in Ex. 1, m.p.: 222°–3°. The NMR, MS and IR spectral data are identical to those given in Example 1.

Anal. calc. for C$_{11}$H$_{15}$ClN$_2$O:C,58.29; H,6.66; N,12.35.
Found: C,58.51; H,6.71; N,12.31.

EXAMPLE 3

(rac)-N-(2-Acetamido)-1-aminoindan.HCl

The title compound was prepared from (rac)-1-aminoindan in a manner analogous to that described in Example 1, m.p.: 201°–2° C. The free base melted at 131°–3° C.

Found: C,58.58; H,6.77; N,12.35.
The NMR, MS and IR spectral data are identical to those given in Example 1.

EXAMPLE 4

(rac)-N-(2-Acetamido)-1-aminotetralin

The title compound was prepared in 25% yield from 1-aminotetralin and 2-chloroacetamide according to the procedure described in Example 1. The base was purified by filtration through silica with acetone as eluent, to give a white solid, m.p.: 13920 –41° C.

Anal. calcd. for C$_{12}$H$_{16}$N$_2$O:C,70.59; H,7.84; N,13.72.
Found: C,70.58; H,7.83; N,13.80.

$^1$H NMR δ (CDCl$_3$): 7.36 (m, 1H, Ph), 7.20 (m, 3H, Ph, CONH$_2$), 7.10 (m, 1H, Ph), 5.52 (br s, 1H, CONH$_2$), 3.78 (br t, 1H, C1-H), 3.39 (s, 2H, CH$_2$), 2.78 (m, 2H, C4-H), 1.96–1.70 (m, 4H, C2-H, C3-H) ppm.

MS: 205 (MH$^+$, 100), 146 (10), 131 (13), 93 (47).

IR (KBr): 3382, 3183, 2936, 1632, 1487, 1445, 1395, 1333 cm$^{-1}$.

EXAMPLE 5

(rac)-6-Fluoro-N-(2-acetamido)-1-aminoindan.HCl

A mixture of 6-fluoro-1-aminoindan (10.6 g, 70.2 mmole), 2-chloroacetamide (6.4 g, 68 mmole), sodium bicarbonate (6.4 g, 76 mmole) and absolute ethanol (130 ml) was refluxed for 22 hr. The reaction mixture was then filtered, ice-cooled and gaseous HCl was bubbled through for 40 min. The solid was collected, washed with ether/hexane and dried. Crystallization from 2:1 MeOH:EtOH afforded the title compound (3.4 g, 21%). M.p. of the free base: 100°–102° C.

Anal. calcd. for C$_{11}$H$_{14}$ClFN$_2$O:C,53.99; H,5.77; N,11.45; F,7.77.
Found: C,53.91; H,5.63; N,11.24; F,8.12.

$^1$H NMR δ (D$_2$O): 7.38 (m, 1H, Ph), 7.28 (m, 1H, Ph), 7.15 (m, 1H, Ph), 4.91 (m, 1H, C1-H), 3.92 (m, 2H, CH$_2$), 3.08 (m, 1H, C3-H), 2.96 (m, 1H, C3-H'), 2.63 (m, 1H, C2-H), 2.28 (m, 1H, C2-H') ppm.

MS: 209 (MH$^+$,100), 150 (10), 135 (6).

IR (KBr): 3360, 3190, 3020, 2910, 2410, 1690, 1600, 1500, 1405 cm$^{-1}$.

EXAMPLE 6

(rac)-N-(N-Boc-4-aminobutyryl)-1-aminoindan

A solution of Boc-GABA anhydride (4.46 g, 11.5 mmole, prepared from Boc GABA and DCC in CH$_2$Cl$_2$) in dry THF (15 ml) was added to a solution of 1-aminoindan (1.5 g, 11.2 mmole) in dry THF (15 ml), and DMAP (1.5 g, 12.3 mmole) was then added in one portion. The reaction mixture was stirred at RT for 6 hr, filtered and the filtrate was evaporated to dryness. The residue was dissolved in CH$_2$Cl$_2$ (25 ml), the solution was then washed with 10% NaHCO$_3$ (25 ml) and H$_2$O (15 ml), dried over MgSO$_4$ and evaporated to dryness. The residue was treated with hexane/ether (1:1, 100 ml), and the resultant crude product was filtered, dried and purified by filtering-column chromatography (Silica, 1:1 hexane/EtOAc as eluent), and crystallized from hexane:EtOAc, to give 2.5 g (7.84 mmole, 71%) of a white crystalline solid, m.p.: 11820 –20° C.

$^1$H NMR δ (DMSO): 8.15 (d, 1H, NHCO), 7.20 (m, 4H, Ph), 6.80 (br t, 1H, NHCOO), 5.26 (q, 1H, C1-H), 2.92 (m,

3H, CH$_2$NHBoc, C3-H), 2.78 (m, 1H, C3-H'), 2.36 (m, 1H, C2-H), 2.11 (m, 2H, CH$_2$CONH), 1.76 (m, 1H, C2-H'), 1.64 (m, 2H, CH$_2$CH$_2$,CH$_2$NHBoc), 1.38 (s, 9H, Boc) ppm.

MS: 319 (MH$^+$, 100), 263 (MH$^+$—CH$_2$=CMe$_2$, 68), 219 (263-CO$_2$, 30).

EXAMPLE 7

(rac)-N-(4-Aminobutyryl)-1-aminoindan.HCl

Also called N-(4-aminobutanoyl)-1-aminoindan.HCl. N-(N-Boc-4-aminobutyryl)-1-aminoindan (2.50 g, 7.8 mmole) was dissolved in dry dioxane (20 ml), and 1.7N HCl in dioxane (20 ml) was added. The solution was stirred at ambient temperature for 4 hr, evaporated to dryness, and the residue taken up in CH$_2$Cl$_2$:H$_2$O mixture (1:1, 160 ml). The aqueous phase was separated, filtered through millipore and evaporated to dryness in vacuo. The crude product was crystallized from 40:60 EtOAc:ethanol to give 1.55 g (78%) white crystalline solid, m.p.: 168° C.

Anal. calcd. for C$_{13}$H$_{19}$ClN$_2$O: C,61.28; H,7.51; N,10.99;
Found: C,61.37; H,7.66; N,11.11.

$^1$H NMR δ (DMSO): 8.37 (d, 1H, NHCO), 8.00 (br s, 3H, NH$_3^+$), 7.20 (m, 4H, Ph), 5.28 (q, 1H, C1-H), 2.92 (m, 1H, C3-H), 2.80 (m, 3H, C3-H', CH$_2$NH$_3$+), 2.37 (m, 1H, C2-H), 2.26 (t, 2H, CH$_2$CONH), 1.85 (m, 2H, CH$_2$CH$_2$CONH), 1.77 (m, 1H, C2-H') ppm.

MS: 219 (MH$^+$, 100), 202 (14), 117 (31).

IR (KBr): 3272, 3235, 3032, 1644, 1628, 1553, 1462, 1454 cm$^{-1}$.

EXAMPLE 8

(rac)-N-Formyl-1-aminoindan

The title compound was prepared from 1-aminoindan according to the procedure described in J.Med.Chem., 9,830 (1966), and crystallized from EtOAc (40% overall yield), m.p.: 105° C.

Anal. calcd. for C$_{10}$H$_{11}$NO: C,74.50; H,6.88; N,8.69.

Found: C,74.59; H,6.88; N,8.67. $^1$NMR δ (CDCl$_3$): 826 (m, 1H, HCO), 725 (m, 4H, Ph), 5.80 (br s, 1H, NH), 5.56, 5.00 (q, 1H, C1H,2 rotamers), 3.01 (m, 1H, C3-H), 2.88 (m, 1H, C3-H'), 2.62 (m, 1H, C2-H), 1.85 (m, 1H, C2-H') ppm.

MS: 162 (MH$^+$, 30), 117 (MH$^+$-HCONH$_2$, 100).

IR (KBr): 3270, 3040, 2960, 1635, 1545, 1400, 1245 cm$^{-1}$.

EXAMPLE 9

(R)-N-Formyl-1-aminoindan -aminoindan in

The title compound was obtained from (R)-1-aminoindan in a manner analogous to that described in Ex. 8, m.p.: 123°–50° C.

Anal. found: C, 74.61; H, 6.97; N, 8.76.

The NMR, MS and IR spectral data are identical to those given in Ex. 8.

EXAMPLE 10

(S)-N-Formyl-1-aminoindan

The title compound was obtained from (S)-1-aminoindan in a manner analogous to that described in Ex. 8, m.p.: 124°–125° C.

Anal. found: C, 74.70; H, 7.13; N, 8.94.

The NMR, MS and IR spectral data are identical to those given in Ex. 8.

EXAMPLE 11

(rac)-N-Butyryl-1-aminoindan

A solution of butyryl chloride (5.33 g, 50 mmole) in anh. DME (60 ml) was added slowly to a stirred and ice-cooled solution of 1-aminoindan (6.66 g, 50 mmole) and Et$_3$N (10.0 g, 100 mmole) in anh. DME (75 ml), and the mixture stirred at ambient temperature for 24 hr. After removal of volatiles under reduced pressure, the residue was taken up in 1:1 water/EtOAc mixture (300 ml). The organic layer was separated, dried on Na$_2$SO$_4$ and evaporated to dryness. The crude product was crystallized from EtOAc, to give 5.9 g (58%) of the title compound as a white solid, m.p.: 8420 –5° C.

Anal. calcd. for C$_{13}$H$_{17}$NO: C,76.81; H,8.43; N,6.89.
Found: C,77.18; H,8.48; N,7.08.

$^1$H NMR δ (CDCl$_3$): 7.24 (m, 4H, Ph), 5.73 (br d, 1H, NH) 5.48 (q, 1H, C1-H), 2.97 (m, 1H, C3-H), 2.85 (m, 1H, C3-H'), 2.59 (m, 1H, C2-H), 2.19 (t, 2H, CHCO), 1.78 (m, 1H, C2-H'), 1.70 (m, 2H, CH$_3$CH$_2$), 0.97 (t, 3H, CH$_3$) ppm.

MS: 204 (MH$^{30}$, 100), 179 (12), 160 (18).

IR (KBr): 3279, 2961, 1640, 1545, 1481, 1458 cm$^{-1}$.

EXAMPLE 12

(rac)-N-Methyl-1-aminoindan.HCl

The title compound was prepared from (rac)-1-aminoindan, according to J.Med.Chem., 9, 830 (1963), and crystallized from iPrOH/Et$_2$O (overall yield 25%), m.p.: 147°–9° C.

$^1$H NMR δ (CDCl$_3$): 9.81 (br s, 2H, NH$_2^+$), 7.80 (d, 1H, Ph) 7.28 (m, 3H, Ph), 4.65 (m, 1H, C1-H), 3.28 (m, 1H, C3-H), 2.93 (m, 1H, C3-H'), 2.47 (t, 4H, CH$_3$, C2-H), 2.36 (m, 1H, C2-H') ppm.

MS: 148 (MH$^+$, 100), 117 (18).

IR (KBr): 2934, 2751, 2694, 1462, 1431, 1414, 1339 cm$^{-1}$.

EXAMPLE 13

(R)-N-Methyl-1-aminoindan.HCl

The title compound was prepared from (R)-1-aminoindan in a manner analogous to that described in Example 12, m.p.: 153° C.

Anal. calcd. for C$_{10}$H$_{14}$ClN: C,65.39; H,7.68; N,7.63; Cl,19.30.

Found: C,65.66; H,7.89; N,7.57; Cl,19.80.

The NMR, MS and IR spectral data are identical to those given in Example 12.

EXAMPLE 14

(S)-N-Methyl-1-aminoindan.HCl

The title compound was prepared from (S)-1-aminoindan in a manner analogous to that described in Example 12, m.p.: 154° C.

Found: C,65.30; H,7.83; N,7.77; Cl,19.48.

The NMR, MS and IR spectral data are identical to those given in Example 12.

EXAMPLE 15

(rac)-N,N-Dimethyl-1-aminoindan.HCl

The title compound was prepared from 1-aminoindan, according to Yakugaku Zasshi, 82, 1597 (1962), Chem.Abs., 59, 611f (1963) and crystallized from iPrOH/Et$_2$O (40% overall yield), m.p.: 1950°–70° C.

Anal. calcd. for C$_{11}$H$_{16}$ClN: C,66.82; H,8.16; N,7.09; Cl,17.93.

Found: C,66.86; H,8.33; N,6.85; Cl,18.30. $^1$H NMR δ (CDCl$_3$): 7.93 (d, 1H, Ph), 7.35 (m, 3H, Ph), 4.95 (dd, 1H, C1-H), 3.15 (m, 1H, C3-H), 3.02 (m, 1H, C3-H'), 2.71 (s, 6H, CH$_3$), 2.55 (m, 1H, C2-H), 2.46 (m, 1H, C2-H'ppm.

MS: 162 (MH$^+$, 100), 117 (MH$^{30}$ -Me$_2$NH,19).

IR (KBr): 2932, 2561, 2525, 2467, 1478, 1422, 1362, 1192 cm$^{-1}$.

EXAMPLE 16

(rac)-N-Benzyl-1-aminoindan.HCl

A solution of 1-chloroindan (7.6 g, 49.7 mmole) and benzylamine (21.3 g, 199 mmole) in toluene (55 ml) was refluxed for 10 hr. The reaction mixture was filtered, water (50 ml) was added to the filtrate and acidified to pH=2.5 by means of 33% H$_2$SO$_4$. The aqueous phase was separated, its pH was adjusted to 6–6.5 by means of 25% NH$_4$OH, and extracted with toluene. The organic phase was dried and evaporated to dryness (8.2 g, 74%). 1.7 g of the crude free base was converted to the HCl salt by means of isopropanolic HCl, affording 1.3 g (66%) of a white crystalline solid, m.p.: 180° C.

Anal. calcd. for C$_{16}$H$_{18}$ClN: C,73.96; H,6.98; N,5.39; Cl,13.65.

Found: C,73.93; H,7.04; N,5.63; Cl,13.62.

$^1$H NMR δ (DMSO): 10.0 (br d, 2H, NH$_2^+$), 7.90–7.25 (m, 9H, Ph), 4.74 (br s, 1H, C1-H), 4.15 (br s, 2H, Ph CH$_2$), 3.16 (m, 1H, C3-H), 2.86 (m, 1H, C3-H'), 2.40 (m, 2H, C2-H) ppm.

MS: 224 (MH$^+$, 100), 117 (MH$^+$-PhCH$_2$NH$_2$, 68).

IR (KBr): 2886, 2776, 2759, 2730, 2629, 2552, 1582, 1484, 1458, 1433, 1424, 1383, 1210 cm$^{-1}$.

EXAMPLE 17

(rac)-N-Acetyl-1-aminoindan

The title compound was obtained in 52% yield by acetylation of 1-aminoindan, according to J.Med.Chem., 9, 830 (1966), m.p.: 124°–50C.

$^1$H NMR δ (CDCl$_3$): 7.25 (m, 4H, Ph), 5.78 (br s, 1H, NH), 5.46 (q, 1H, C1-H), 2.98 (m, 1H, C3-H), 2.86 (m, 1H, C3-H'), 2.58 (m, 1H, C2-H), 2.01 (s, 3H, CH$_3$), 1.80 (m, 1H, C2-H') ppm.

MS: 176 (MH$^+$, 100), 117 (MH$^+$-CH$_3$CONH$_2$, 100).

IR (KBr): 1632, 1551, 1481, 1458, 1437, 1372, 1290 cm$^{-1}$.

EXAMPLE 18

(R)-N-Acetyl-1-aminoindan

The title compound was obtained from (R)-1-aminoindan in a manner analogous to that described in Example 17, m.p.: 152°–30C.

Anal. calcd. for C$_{11}$H$_{13}$NO: C,75.40; H,7.48; N,8.00.

Found: C,75.42; H,7.43; N,7.80.

The NMR, MS and IR spectral data are identical to those given in Example 17.

EXAMPLE 19

(S)-N-Acetyl-1-aminoindan

The title compound was obtained from (S)-1-aminoindan in a manner analogous to that described in Example 17, m.p.: 154° C.

Anal. calcd. for C$_{11}$H$_{13}$NO: C,75.40; H,7.48; N,8.00.

Found: C,75.68; H,7.66; N,7.99.

The NMR, MS and IR data are identical to those given in Example 17.

EXAMPLE 20

(rac)-7-Methyl-N-acetyl-1-aminoindan

The title compound was prepared in 55% yield according to the procedure described in Example 17, m.p.: 166°–7° C.

Anal. calcd. for C$_{12}$H$_{15}$NO: C,75.87; H,7.77; N,7.54.

Found: C,76.16; H,7.98; N,7.40.

$^1$H NMR δ (CDCl$_3$): 7.10 (m,3H, Ph), 5.60 (br d, 1H, NH), 5.48 (m, 1H, C1-H), 3.03 (m, 1H, C3-H), 2.86 (m, 1H, C3-H'), 2.43 (m, 1H, C2-H), 2.29 (s, 3H, PhMe), 2.01 (m, 1H, C2-H'), 1.96 (s, 3H, CH$_3$) ppm.

MS: 190 (MH$^+$, 100), 182 (35), 165 (11).

IR: 3281, 2919, 1636, 1547, 1375, 1291 cm$^{-1}$.

EXAMPLE 21

(R)-4,5-Dimethoxy-N-acetyl-1-aminoindan

The title compound was prepared in 66% yield according to the procedure described in Example 17, m.p.: 175° C.

Anal. calcd. for C$_{13}$H$_{17}$NO$_3$: C,66.6; H,7.43; N,6.06.

Found: C,66.37; H,7.43; N,5.95.

$^1$H NMR δ (CDCl$_3$): 6.95 (d, 1H, Ph), 6.77 (d, 1H, Ph), 5.82 (br d, 1H, NH), 5.38 (m, 1H, C1-H), 3.84 (s, 6H, OMe), 3.0 (m, 1H, C3-H), 2.84 (m, 1H, C3-H'), 2.56 (m, 1H, C2-H), 2.01 (s, 3H, Me), 1.80 (m, 1H, C2-H') ppm.

MS: 236 (MH$^+$,11), 177 (MH+-CH$_3$CONH$_2$, 100).

IR: 3281, 2959, 2835, 1638, 1551, 1495, 1296, 1260, 1217 cm$^{-1}$.

EXAMPLE 22

(rac)-6-Fluoro-N-acetyl-1-aminoindan

The title compound was prepared in 51% yield according to the procedure described in Example 17, m.p.: 139°–141° C.

Anal. calcd. for C$_{11}$H$_{12}$FNO: C,68.37; H,6.26; F,9.84; N,7.25.

Found: C,68.50; H,6.48; F,10.25; N,7.44.

$^1$H NMR δ (CDCl$_3$): 7.15 (dd, 1H, Ph), 6.93 (m, 2H, Ph) 5.78 (br s, 1H, NH), 2.92 (m, 1H, C3-H), 2.82 (m, 1H, C3-H'), 2.03 (s, 3H, Me), 2.60 (m, 1H, C2-H), 1.82 (m, 1H, C2-H') ppm.

MS: 194 (MH$^+$, 100), 135 (MH$^+$-AcNH$_2$, 31).

IR (KBr): 3279, 2963, 1634, 1551, 1489, 1373, 1296 cm$^{-1}$.

EXAMPLE 23

(R)-6-Fluoro-N-acetyl-1-aminoindan

The title compound was obtained in 47% yield from (R)-6-fluoro-1-aminoindan in a manner analogous to that described in Example 17, m.p.: 181°–3° C.

The NMR, MS and IR spectral data are identical to those given in Example 22.

Anal. found for C$_{11}$H$_{12}$FNO: C,68.31; H,6.22; N,7.31, F,10.23.

EXAMPLE 24

(S)-6-Methoxy-1-aminoindan.HCl

The title compound was prepared in 53% yield from 6-methoxy-1-indanone (prepared via the methods described in J.Org.Chem., 46,2974 (1981) and in J.Chem.Soc. Peskin Trans I, 151 (1972)) in a manner analogous to that described in Eur.Pat.Appl. 436492, m.p.: 239°–242° C. (dec.).

Anal. calcd. for $C_{11}H_{14}ClNO$: C, 60.15; H, 7.02; N, 7.02; Cl, 17.79.

Found: C, 60.46; H, 7.15; N, 7.11; Cl, 17.53.

$^1$H NMR δ ($D_2O$): 7.35 (1H, Ph), 7.12 (1H, Ph), 7.06 (1H, Ph), 4.85 (m, 1H, C1-H), 3.85 (s, 3H, OMe), 3.08 (m, 1H, C3-H), 2.95 (m, 1H, C3-H'), 2.62 (m, 1H, C2-H), 2.17 (m, 1H, C2-H') ppm.

MS: 162 (M-H, 63), 147 (100).

IR (KBr): 2940, 1609, 1500, 1250 cm$^{-1}$.

EXAMPLE 25

(rac)-6-Methoxy-1-aminoindan.HCl

The title compound was prepared in 72% from 6-methoxy-1-indanone in a manner analogous to that described in Ex. 24, except that 6-methoxy-1-oximinoindan was reduced by hydrogen over Pd on charcoal; m.p.: 244°–5° C.

The NMR, MS and IR data are identical to those described in Ex. 24.

Found for $C_{10}H_{14}ClNO$: C, 60.22; H, 6.97; N, 6.83; Cl, 17.59.

EXAMPLE 26

(rac) 6-methoxy-N-acetyl-1-aminoindan

The title compound was prepared in 27% yield from (rac)-6-methoxy aminoindan according to the procedure described in Example 17, m.p.: 131°–2° C.

Anal. calcd. for $C_{12}H_{15}NO_2$: C, 70.22; H, 7.37; N, 6.82.

Found: C, 70.22; H, 7.41; N, 6.84.

$^1$H NMR δ (CDCl$_3$): 7.12 (d, 1H, Ph), 6.80 (m, 2H, Ph), 5.77 (br d, 1H, NH), 5.43 (m, 1H, C1-H), 3.78 (s, 3H, OMe), 2.90 (m, 1H, C3-H), 2.78 (m, 1H, C3-H'), 2.58 (m, 1H, C2-H), 2.02 (s, 3H, Me), 1.80 (m, 1H, C2-H') ppm.

IR: 3283, 3075, 3002, 2963, 2940, 2836, 1638, 1551, 1489, 1372, 1327, 1294, 1240, 1146 cm$^{-1}$.

EXAMPLE 27

1-Aminobenzocyclobutene.HCl

The title compound was prepared from benzocyclobutene-1-carboxylic acid in 44% yield, according to the procedure described in J.Med.Chem., 8,255 (1965); m.p.: 184° C.

Anal. calcd. for $C_8H_{10}ClN$: C,61.74; H,6.48; N,9.0.

Found: C, 61.04; H,6.59; N,9.30.

$^1$H NMR δ (DMSO): 8.96 (br s, 3H, NH$_3$ +), 7.40–7.20 (m, 4H, Ph), 4.71 (m, 1H, C1-H), 3.55 (dd, 1H, C2-H), 3.24 (dd, 1H, C2-H') ppm.

MS: 120 (MH$^+$,79), 103 (M-NH$_3$, 100).

IR (KBr): 2963, 2942, 1601, 1584, 1495, 1458, 1368 cm$^{-1}$.

EXAMPLE 28

(rac)-7-Methyl-1-aminoindan.HCl

3-Methyl benzaldehyde was converted to a mixture of 5-methyl-1-indanone and 7-methyl-1-indanone according to the procedure described in Ex. 24. The two isomers were separated by column chromatography (hexane:CH$_2$Cl$_2$) and the latter was converted to the title compound as in Ex. 24. Overall yield 18%, m.p.: >280° C. (dec.).

Anal. calcd. for $C_{10}H_{14}ClN$: C, 65.4; H, 7.63; N, 7.63; Cl, 19.35.

Found: C, 65.62; H, 7.66; N, 7.66; Cl, 18.99.

EXAMPLE 29

(R)-4,5-Dimethoxy-1-aminoindan.HCl

The title compound was prepared in 24% yield from (rac) -4,5-dimethoxy-1-aminoindan (Ex. 31), m.p.: 213°–4° C. (dec.).

Anal. calcd. for $C_{11}H_{16}ClNO_2$: C, 57.52; H, 7.02; N, 6.10.

Found: C, 57.18; H, 7.08; N, 6.38.

$^1$H NMR δ (D$_2$O): 7.29 (d, 1H, Ph), 7.10 (d, 1H, Ph), 4.85 (m, 1H, C1-H), 3.95 (s, 3H, OMe), 3.88 (s, 3H, OMe), 3.20 (m, 1H, C3-H), 3.07 (m, 1H, C3-H'), 2.65 (m, 1H, C2-H) 2.20 (m, 1H, C2-H') ppm.

MS: 192 (M-H+, 100), 177 (61).

IR (KBr): 3262, 2928, 1620, 1605, 1532, 1489, 1443, 1432, 1375 cm$^{-1}$.

EXAMPLE 30

(S)-4,5-Dimethoxy-1-aminoindan.HCl

The title compound was prepared in a manner analogous to that described in Example 29, m.p.: 209°–10° C. (dec.).

The NMR, MS and IR spectral data are identical to those described in Example 29.

Found for $C_{11}H_{16}ClNO_2$: C, 56.36; H, 7.00; N, 6.22.

EXAMPLE 31

(rac)-4,5-Dimethoxy-1-aminoindan.HCl

The title compound was prepared in 70% yield from 2,3-dimethoxy benzaldehyde in a manner analogous to that described in Ex. 24, m.p.: 202°–4° C. (dec.).

Anal. calcd. for $C_{11}H_{16}ClNO_2$: C, 57.51; H, 7.02; N, 6.10.

Found: C, 57.58; H, 6.99; N, 5.69.

The NMR, MS and IR spectral data are identical to those described in Ex. 29.

EXAMPLE 32

(rac)-6-Hydroxy-5-methoxy-1-aminoindan.HCl

The title compound was prepared in 5% yield from 3-methoxy-4-hydroxy-benzaldehyde in a manner analogous to that described in Ex. 24.

Anal. calcd. for: $C_{10}H_{13}NO_2$ (free base): C, 67.02; H, 7.31; N, 7.81.

Found: C, 66.97; H, 7.39; N, 7.88.

$^1$H NMR δ (D$_2$O): 7.08, 7.01 (s, 2H, Ph), 4.80 (m, 1H, C1-H) 3.91 (s, 3H, OMe), 3.12 (m, 1H, C3-H), 2.95 (m, 1H, C3-H'), 2.60 (m, 1H, C2-H), 2.15 (m, 1H, C2-H') ppm.

IR (KBr): 3485, 3413, 3009, 2943, 1611, 1509, 1456, 1442, 1379, 1325, 1269, 1233 cm$^{-1}$.

EXAMPLE 33

(rac)-4-Hydroxy-5-methoxy-1-aminoindan.HCl

The title compound was prepared in 45% yield from 4-benzyloxy-5-methoxy-1-indanone oxime, m.p.: 188°–90°

C. (dec.). $^1$H NMR 6 (D$_2$O): 7.05 (m, 2H, Ph), 4.80 (m, 1H, C1-H), 3.88 (s, 3H, OMe), 3.05 (m, 1H, C3-H), 2.92 (m, 1H, C3-H'), 2.63 (m, 1H, C2-H), 2.18 (m, 1H, C2-H') ppm.

MS: 178 (M-H+, 100), 148 (12).

IR (KBr): 3401, 2932, 1615, 1526, 1487, 1425, 1279 cm$^{-1}$.

EXAMPLE 34

(rac)-6-Hydroxy-1-aminoindan.HCl

The title compound was prepared in 45% yield from (rac)-6-methoxy-1-aminoindan, m.p.: 202°–3° C. (dec.).

Anal. calcd. for C$_9$H$_{12}$ClNO: C, 58.22; H, 6.52; N, 7.55. Found: C, 58.08; H, 6.41; N, 7.39.

$^1$H NMR 6 (D$_2$O): 7.15 (d, 1H, Ph), 6.90 (s, 1H, Ph), 6.80 (d, 1H, Ph), 4.67 (m, 1H, C1-H), 3.05 (m, 1H, C3-H), 2.86 (m, 1H, C3-H'), 2.55 (m, 1H, C2-H), 2.06 (m, 1H, C2-H') ppm.

MS: 148 (M-H$^+$, 65), 132 (100).

IR (KBr): 3297, 3044, 1615, 1499, 1460, 1451, 1375, 1281, 1213 cm$^{-1}$.

EXAMPLE 35

(R)-6-Hydroxy-1-aminoindan.HCl

The title compound was prepared in 43% yield from (R)-6-methoxy-1-aminoindan, m.p.: 199°–200° C.

Found for: C$_9$H$_{12}$ClNO: C, 57.98; H, 6.30; Cl, 18.88; N, 7.55.

The NMR and MS spectral data are identical to those described in Ex. 34.

EXAMPLE 36

(rac)-5-Methoxy-1-aminoindan.HCl

The title compound was prepared in 25% yield from 5-methoxy-1-indanone in a manner analogous to that described in Ex. 24, m.p.: 225°–7° C. (dec.).

Anal. calcd. for C$_{10}$H$_{14}$ClNO: C, 60.15; H, 7.02; N, 7.02, Cl, 17.79.

Found: C, 59.77; H, 6.94; N, 7.08; Cl, 17.53

$^1$H NMR δ (D$_2$O): 7,43 (d, 1H, Ph), 7.00 (d, 1H, Ph), 6.93 (m, 1H, Ph), 4.85 (m, 1H, C1-H), 3.85 (s, 3H, OMe), 3.15 (m,1H, C3-H), 2.9 8 (m, 1H, C3-H') 2.63 (m, 1H, C2-H) 2.17 (m, 1H, C2-H') ppm.

MS: 162 (M-H$^+$, 100), 147 (100)

IR (KBr): 2900, 1602, 1509, 1500, 1 300, 1252 cm$^{-1}$.

EXAMPLE 37

(rac)-N-(3-Cyanopropyl)-1-aminoindan

Potassium carbonate (15.5 g, 112 mmole) and 4-chlorobutyronitrile (11.58 g, 112 mmole) was added to a solution of 1-aminoindan (5.0 g, 37.6 mmole) in acetonitrile (50 ml), and the mixture refluxed for 2 hr. A second portion of 4-chlorobutyronitrile (5.0 g) was then added, the mixture further heated for 24 hr, filtered and the filtrate evaporated to dryness. Unreacted 4-chlorobutyronitrile was removed by treating the residue (20 g) with isopropanolic HCl (16.7 ml, 24%) followed by successive extractions with ether (3×150 ml). The crude product thus obtained was further purified by column chromatography (Silica, CH$_2$C$_2$:MeOH 98:2) to afford 3.7 g (49%) of tan-colored crystalline mass.

$^1$H NMR δ (CDCl$_3$): 7.32 (m, 1H, Ph), 7.20 (m, 3H, Ph), 4.22 (t, 1H, C1-H), 2.98 (m, 1H, C3-H), 2.85 (m, 2H, CH$_2$NH) 2. 81 (m, 1H, C3-H'), 2.49 (t, 2H, CH$_2$CN), 2.42 (m, 1H, C2-H), 1.83 (m, 2H, CH$_2$CH$_2$CH$_2$), 1.77 (m, 1H, C2-H') ppm.

MS: 201 (MH$^+$, 63), 117 (63), 85 (100).

EXAMPLE 38

(rac)-5-Methyl-1-aminoindan.HCl

5-Methyl-1-indanone, obtained from 3-methyl benzaldehyde a s described in Ex. 28, was converted to the title compound according to the procedure described in Ex. 24 (overall yield 6%), m.p.: 247°–90° C. (dec.).

Anal. calcd. for C$_{10}$H$_{14}$ClN: C, 65.40; H, 7.63; N, 7.63; Cl, 19.35

Found: C, 65.12; H, 7.36; N, 7.58; Cl 19.18.

$^1$H NMR δ (D$_2$O): 7.45 (d, 1H, Ph), 7.2 (s, 1H, Ph), 7.20 (d, 1H, Ph), 4.81 (m, 1H, C1-H), 3.22 (m, 1H, C3-H), 2.90 (m, 1H, C3-H'), 2.56 (m, 1H, 2-H), 2.35 (s, 3H, CH$_3$) 2.12 (m, 1H, C2-H') ppm.

EXAMPLE 39

(rac)-trans-2-Methyl-1-aminoindan.HCl

2-Methyl-1-indanone was prepared from benzene and α-bromoisobutyryl bromide, as in Polish J. Chem. 52, 2059 (1978), and converted to the oximino derivative, from which the title compound was obtained by reduction with Zn/HOAc. The overall yield was 14%, m.p.: >275° C. (dec.).

Anal. calcd. for C$_{10}$H$_{14}$NCl: C, 65.40; H, 7.63; N, 7.63; Cl, 19.35.

Found: C, 65.49; H, 7.90; N, 7.68; Cl, 19.14. $^1$H NMR 6 (D$_2$O): 7.60–7.25 (m, 4H, Ph); 4.70 (d, 1H, C1-H), 3.17 (dd, 1H, C3-H), 2.87 (m, 1H, C2-H), 2.79 (dd, 1H, C3-H'), 1.19 (d, 3H, CH$_3$) ppm.

EXAMPLE 40

(rac)-cis-2-Methyl-1-aminoindan.HCl

The title compound was prepared according to procedure described in Ex. 39, except that 2-methyl-1-oximinoindan was reduced by hydrogenation over Pd on charcoal, m.p.: 235°–7° C. (dec.).

Found for C$_{10}$H$_{14}$Cl N: C, 65.78; H, 7.93; N, 7.72; Cl, 19.39.

$^1$H NMR δ (D$_2$O): 7.60–7.25 (m, 4H, Ph), 4.45 (d, 1H, C1-H) 3.33 (dd, 1H, C3-H), 2.68 (dd, 1H, C3-H'), 2.58 (m, 1H, C2-H), 1.25 (d, 3H, CH$_3$) ppm.

EXAMPLE 41

(rac)-3,5,7-Trimethyl-1-aminoindan.HCl

The title compound was prepared in 9% yield from m-xylene and crotonic acid, according to the procedures described in Ex. 24, m.p.: >275° C. (dec.).

Anal. calcd. for C$_{12}$H$_{18}$NCl: C, 68.08; H, 8.51; N, 6.62; Cl, 16.78.

Found: C, 68.11; H, 8.46; N, 6.73; Cl, 17.08.

$^1$H NMR δ (D$_2$O): 7.10 (s, H, Ph), 7.05 (s, H, Ph), 4.89 (m, 1H, C1-H), 3.25 (m, 1H, C3-H), 2.90 (m, 1H, C2-H), 2.37 (s, 3H, CH$_3$), 2.33 (s, 3H, CH$_3$), 1.70 (m, 1H, C2-H'), 1.34 (d, 3H, CH$_3$) ppm.

EXAMPLE 42

(rac)-7-Hydroxy-1-aminoindan.HCl

The title compound was prepared in 6% yield from phenol and 3-chloro-propionylchloride according to the procedures described in Ex. 24, m.p.: 179°–81° C.

Anal. calcd. for $C_9H_{12}ClNO$: C, 58.22; H, 6.52; N, 7.55; Cl, 19.10.

Found: C, 58.15; H, 6.47; N, 7.42; Cl, 19.39.

$^1$H NMR δ ($D_2O$): 7.29 (t, 1H, Ph), 6.93 (d, 1H, Ph), 6.78 (d, 1H, Ph), 4.94 (m, 1H, C1-H), 3.12 (m, 1H, C3-H), 2.97 (m, 1H, C3-H'), 2.61 (m, 1H, C2-H), 2.12 (m, 1H, C2-H') ppm.

EXAMPLE 43

(rac)-N,N-Di-(1-indanyl)amine.HCl

A solution of (rac)-1-chloroindan (9.2 g, 60 mmole) in acetonitrile (25 ml) was added dropwise (10 min.) to a stirred and heated (65° C.) suspension of (rac)-1-aminoindan (8.0 g, 60 mmole), $K_2CO_3$ (8.3 g, 60 mmole) in acetonitrile (100 ml), under $N_2$ atmosphere. The mixture was further stirred at 65° C. for 24 hrs; the solvent was removed under reduced pressure and the residue was partitioned between 10% NaOH (100 ml) and $CH_2Cl_2$ (100 ml). The aqueous layer was separated, extracted with $CH_2C_{l2}$ (50 ml), and the combined organic layer was dried ($Na_2SO_4$) and evaporated to dryness. The crude product was purified by flash column chromatography (silica, hexane:ETOAc 80:20), to give 5.4 g (36%) of the free base, which was converted to its HCl salt by dissolving it in $Et_2O$ (60 ml) and adding to it an $Et_2O$ solution saturated with HCl gas (75 ml). The resulting suspension was filtered, and the collected solid was crystallized from EtOH/iPrOH, to give 4.90 g (79%) of the title compound as a mixture of two diastereomers, white crystalline solid, m.p.: 226°–80° C.

Anal. calcd. for $C_{18}H_{20}NCl$: C, 75.64; H, 7.05; N, 4.90; Cl, 12.41.

Found: C, 75.90; H, 6.85; N, 4.96; Cl, 12.34. $^1$H NMR δ (DMSO): 9.80, 9.60 (brs, 2H, $NH_2^+$), 7.80, 7.78 (d,d, 2H, Ph), 7.36, 7.28 (m, m, 6H, Ph), 4.93, 4.87 (m, m, 2H, C1-H), 3.24, 2.91 (m, 2H, C3-H), 2.91 (m, 2H, C3-H'), 2.52 (m, 2H, C2-H), 2.38 (m, 2H, C2-H') ppm.

MS: 250 ($MH^+$, 100)

IR: 3455, 2938, 2786, 2692, 2625, 1578, 1482, 1460, 1435, 1425, 1358, 1028 $cm^{-1}$.

EXAMPLE 44

(rac)-N-(2-N-Boc-aminoacetyl)-1-aminoindan

A mixture of (rac)-1-aminoindan (2.5 g, 18.8 mmole), N-Boc-glycin-N-hydroxysuccinimide ester (5.0 g, 17.7 mmole), DMAP (2.5 g, 20.5 mmole) in 1,2-dimethoxyethane (30 ml) was stirred at ambient temperature for 20 hrs and evaporated to dryness under reduced pressure. The residue was taken up in $Et_2O$ (30 ml) and water (15 ml); the organic phase was separated, washed with 0.1N HCl (15 ml), 10% $NaHCO_3$ (15 ml) and water (20 ml), dried ($MgSO_4$) and evaporated to dryness under reduced pressure. The residue was treated (30 min. stirring, RT) with hexane (30 ml) to give 4.55 g (15.7 mmole, 88%) of a white solid, m.p.: 82°–4° C.

$^1$H NMR δ ($CDCl_3$): 7.22 (m, 4H, Ph), 6.45 (br d, 1H, CONH) 5.47 (m, 1H, C1-H), 5.25 (br s, 1H, Boc NH), 3.82 (d, 2H, $CH_2$), 2.95 (m, 1H, C3-H), 2.86 (m, 1H, C3-H'), 2.58 (m, 1H, C2-H), 1.79 (m, 1H, C2-H') ppm.

MS: 291 ($MH^+$, 32), 235 ($MH^+$-$Me_2CCH_2$, 100), 119 (48), 117 (59).

EXAMPLE 45

(rac)-N-(2-Aminoacetyl)-1-aminoindan.HCl

To a solution of (rac)-N-(2-N-Boc-aminoacetyl)-1-aminoindan (5.9 g, 20.34 mmole) in iPrOH (60 ml) was added 24% isorpopanolic HCl (12.5 ml). The mixture was stirred at ambient temperature for 20 hrs and evaporated to dryness under reduced pressure. The residue was taken up in a 1:1 water/$CH_2Cl_2$ (400 ml) mixture. The aqueous layer was separated, filtered through millipore and evaporated to dryness under reduced conditions. The crude product was crystallized from EtOH to give 2.7 g (59%), white crystalline solid, m.p.: 201°–5° C.

Anal. calcd. for $C_{10}H_{13}ClN_2O$: C, 58.54; H, 6.25; N, 12.41; Cl, 15.71.

Found: C, 58.24; H, 6.50; N, 12.44; Cl, 15.47.

$^1$H NMR δ (DMSO): 8.93 (d, 1H, CONH), 8.35 (brs, 3H, $NH_3^+$), 5.31 (m, 1H, C1-H), 3.58 (m, 2H, $CH_2$), 2.95 (m, 1H, C3-H), 2.83 (m, 1H, C3-H'), 2.40 (m, 1H, C2-H), 1.84 (m, 1H, C2-H') ppm.

MS: 191 ($MH^+$, 100).

IR: 3241, 3000, 2978, 1659, 1613, 1562, 1478 $cm^{-1}$.

EXAMPLE 46

(rac)-N-Benzoyl-1-aminoindan

The title compound was prepared in 77% from (rac)-1-aminoindan (1.0 g, 7.5 mmole) and benzoyl chloride (2.1 g, 15 mmole), under the Schotten-Bauman conditions, according to J.Chem.Soc. 71, 251 (1897) and J.Org.Chem. 27, 4465 (1962), m.p.: 140°–2° C.

Anal. calcd. for $C_{16}H_{15}NO$: C, 80.98; H, 6.37; N, 5.90.

Found: C, 80.11; H, 6.42; N, 5.89.

$^1$H NMR δ ($CDCl_3$): 7.90–7.20 (m, 9H, Ph), 6.40 (br d, 1H, NH), 5.70 (m, 1H, C1-H), 3.05 (m, 1H, C3-H), 2.92 (m, 1H, C3-H'), 2.72 (m, 1H, C2-H), 1.97 (m, 1H, C2-H') ppm.

MS: 238 ($MH^+$, 100) 122 (48).

EXAMPLE 47

N-(2-n-Propylrentanoyl)-1-aminoindan

A solution of valproyl chloride (1.55 g, 9.6 mmole) in toluene (25 ml) was added dropwise to a stirred and ice-cooled solution of 1-aminoindan (1.47 g, 10.0 mmole) and $Et_3N$ (1.11 g, 11 mmole). The mixture was stirred at ambient temperature for 17 hours, EtOAc (60 ml) and water (50 ml) were added and the phases were separated. The organic phase was washed successively with 0.1N HCl (40 ml), 0.1N $NaHCO_3$ (40 ml) and saturated NaCl (40 ml), dried over magnesium sulphate and evaporated to dryness under reduced pressure. The residue was treated with hexane (15 ml, 30 min stirring, RT) and filtered. The crude product was crystallized from hexane:EtOAc (70:30 mixture), to give 1.72 g (6.65 mmole, 69w) of a white crystalline solid, mpt: 133°–4° C.

Anal. Calcd. for $C_{17}H_{25}NO$: C, 78.71; H, 9.72; N, 5.40.

Found: C, 78.83; H, 9.69; N, 5.55.

$^1$H-NMR δ ($CDCl_3$): 7.23 (m, 4H, Ph), 5.65 (br d, 1H, C2-H), 5.53 (m, 1H, C1-H), 2.97,2.86 (m, 2H, C3-H,H'), 2.61 (m, 1H, C2-H), 2.03 (m,1H, $Pr_2CH$), 1.77 (m, 1H, C2-H'), 1.66,1.63 (m, 8H, $CH_3CH_2$ $CH_2$), 0.93 (t, 3H, $CH_3$), 0.90 (t, 3H, $CH_3$) ppm.

MS: 260 ($MH^+$, 100), 172 (9), 144 (48), 117 (14).

IR: 3270, 2955, 2932, 1640, 1545, 1481, 1458, 1257 $cm^{-1}$

EXAMPLE 48

(rac)-N-Methyl-N-acetyl-1-aminoindan (rac)-N-Methyl-1-aminoindan.HCl ((1.0 g, 5.4 mmole), prepared from (rac)-1-aminoindan, as described in Ex. 12)

was acetylated by $Ac_2O$ in a manner analogous to that described in Ex. 17, to give 0.7 g (3.7 mmole, 69%) of a white solid, melting at ambient temperature. $^1H$ NMR δ ($CDCl_3$), a mixture of 2 rotamers: 7.30–7.07 (m, 4H, Ph), 6.30, 5.42 (t, 1H, C1-H), 3.02 (m, 1H, C3-H), 2.88 (m, 1H, C3-H'), 2.69, 2.64 (s, 3H, Me), 2.42 (m, 1H, C2-H), 2.29, 2.18 (s, 3H, Ac), 2.05, 1.86 (m, 1H, C2-H') ppm.

MS: 190 ($MH^+$,34), 174 ($M^+$-$CH_3$, 15), 132 (16), 116 (27).

EXAMPLE 49

(R)-N-Methyl-N-acetyl-1-aminoindan

The title compound was prepared in 73% from (R)-N-methyl-1-aminoindan.HCl (2.8 g, 15.2 mmole) as described in Ex. 48, to give 2.1 g (11.1 mmole) of an off-white crystalline solid, mp: 34°–6° C.

NMR and MS identical to those given in Ex. 48.

IR: 3472, 2944, 1650, 1480, 1402, 1330, 1291, 1155, 1122, 1020, 766 $cm^{-1}$.

EXAMPLE 50

(rac)-N-(2-Propionamido)-1-aminoindan.HCl.$H_2O$

A mixture of 2-bromopropionamide (3.19 g, 21.3 mmole), (rac)-1-aminoindan (3.0 g, 22.2 mmole), sodium S bicarbonate (2.0 g, 23.8 mmole) and absolute ethanol (45 ml) was stirred under reflux for 24 hrs. The reaction mixture was then filtered hot, and the filtrate concentrated in vacuo to about ⅓ of its initial volume, and filtered. The collected solid was dissolved in $CH_2C_2$ and washed successively with 0.1N HCl and water. The aqueous phase was basified to pH 12–13, and filtered. The solid was dried, dissolved in $CH_2C_2$ (30 ml) and converted to the HCl salt by isopropanolic HCl. The latter was collected by filtration, washed with $CH_2C_2$ (3 ml) and dried, to give 2.4 g (9.3 mmole, 44%) of a white solid, mp: 245° C.

Anal. calc. for $C_{12}H_{19}ClN_2O_2$: C, 55.7; H, 7.4; N, 10.8.

Found: C, 55.3; H, 6.5; N, 10.8.

$^1H$ NMR δ (DMSO), two diastereomers: 9.86, 9.54, 9.30, 9.18 (br m, 2H, $NH_2^+$) 18.34, 8.28, 7.72, 7.68 (br s, 2H, $CONH_2$), 7.70, 7.40–7.22 (m, 4H, Ph), 4.65 (br s, 1H, C1-H), 3.98 (br m, 1H, Ca-H), 3.20 (m, 1H, $C_3$-H), 2.84 (m, 1H, $C_3$-H') 2.40 (m, 1H, C2-H), 2.26 (m, 1H, C2-H'), 1.52, 1.48 (d, 3H, Me) ppm.

MS: 205 ($MH^+$, 72), 160 ($MH^+$-$HCONH_2$, 8), 132 (6), 117 (24).

IR (KBr): 3409, 3253, 3133, 2757, 1687, 1553, 1533, 1458, 1400, 1378, 1332, 1256, 1143, 1091, 1035, 762, 641 $cm^{-1}$.

EXAMPLE 51

(rac)-N-(2-Phenylacetyl)-1-aminoindan.HCl

Phenylacetyl chloride (4.76 g, 30.8 mmole) was added dropwise to an ice-cooled solution of (rac)-1-aminoindan (4.0 g, 30 mmole) and $Et_3N$ (6.0 g) in 1,2-dimethoxyethane (40 ml). After completion of addition, the reaction mixture was stirred for 5 hrs at 70° C. and filtered. The solid was dissolved in $CH_2Cl_2$ (100 ml), washed successively with 0.3N HCl, 10%. $NaHCO_3$, water (50 ml each) and dried. The crude product was crystallized from 1:1 hexane:EtOAc (90 ml) to give 2.9 g (11.6 mmole, 39%) white solid, mp: 145°–70° C.

Anal. calc. for $C_{17}H_{17}NO$: C, 81.24; H, 6.82; N, 5.57.

Found: C, 81.31; H, 6.97; N, 5.69.

$^1H$ NMR δ ($CDCl_3$): 7.40–7.10 (m, 9H, Ph), 5.62 (br d, 1H, CONH), 5.48 (q, 1H, C1-H), 3.62 (AB q, 2H, $CH_2$), 2.86 (m, 2H, C3-H, H'), 2.58 (m, 1H, C2-H), 1.65 (m, 1H, C2-H') ppm.

IR (KBr): 3275, 1638, 1545, 1456, 1364, 748, 710 $cm^{-1}$.

EXAMPLE 52

(rac)-N-(m-Anisoyl)-1-aminoindan

The title compound was prepared from (rac)-1-aminoindan (1.6 g, 12.3 mmole) and m-anisoyl chloride (1.9 g, 13.54 mmole) as in Ex. 46; crystallization from EtOAc:hexane gave 2:0 g (7.2 mmole, 59w) white solid, mp: 140° C.

Anal. calc. for $C_{17}H_{17}NO_2$: C, 76.38; H, 6.4; N, 5.2.

Found: C, 76.55; H, 5.75; N, 5.63.

$^1H$ NMR δ ($CDCl_3$): 7.45–7.18 (m, 7H, Ph), 7.04 (m, 1H, Ph) 6.35 (br d, 1H, CONH), 5.68 (q, 1H, C1-H), 3.84 (s, 3H, OMe), 2.98 (m, 2H, C3-H, H'), 2.70 (m, 1H, C2-H), 1.92 (m, 1H, C2-H') ppm.

MS: 268 ($MH^+$,100), 152 (7).

IR (KBr), 3268, 1632, 1586, 1543, 1481, 1350, 1246, 1038, 758, 743, 725 $cm^{-1}$.

EXAMPLE 53

(rac)-N-(4'-Fluorobenzoyl)-1-aminoindan

The title compound was prepared from (rac)-1-aminoindan (1.7 g, 12.85 mmole) and 4-fluorobenzoyl chloride (2.24 g, 14.1 mmole) as in Ex. 52; 1.71 g(6.7 mmole, 52%), mp: 109°–10° C.

$^1H$ NMR δ ($CDCl_3$): 8.15 (td, 1H, Ph), 7.55–7.05 (m, 7H, Ph), 6.95 (m, 1H, CONH), 5.74 (m, 1H, C1-H), 2.98 (m, 2H, C3-H, H'), 2.75 (m, 1H, C2-H), 1.94 (m, 1H, C2-H') ppm.

MS: 256 ($MH^+$, 100), 140 (9).

IR (KBr): 3233, 1638, 1541, 1229, 756, 745 $cm^{-1}$.

EXAMPLE 54

(rac)-N-(p-Toluoyl)-1-aminoindan

The title compound was prepared from (rac)-1-aminoindan (5.0 g, 37.6 mmole) and p-toluoyl chloride (5.2 g, 33.8 mmole) as in Ex. 52; 4.8 g (19.1 mmole, 57%), mp: 140° C.

Anal. calc. for $C_{17}H_{17}NO$: C, 81.24; H, 6.82; N, 5.57.

Found: C, 80.98; H, 6.80; N, 5.48.

$^1H$ NMR δ ($CDCl_3$): 7.68, 7.34, 7.30–7.16 (m, 8H, Ph), 6.34 (br d, 1H, CONH), 5.69 (q, 1H, C1-H), 2.96 (m, 2H, C3-H,H'), 2.70 (m, 1H, C2-H), 2.40 (s, 3H, Me), 1.92 (m, 1H, C2-H') ppm.

MS: 504 ($MMH^+$, 38), 252 ($MH^+$, 100).

IR (KBr): 3273, 3025, 2964, 1630, 1532, 1294, 830, 742 $cm^{-1}$.

EXAMPLE 55

(S)-(1-Indanyl)-glycine.HCl

A mixture of N-(2-acetamindo)-1-aminoindan (4.95 g, 26 mmole, prepared as described in Ex. 2) in conc. HCl (25 ml) was stirred under reflux for 3 hrs, and evaporated to dryness under reduced pressure. The residue was dissolved in water (30 ml) and the solution was basified to pH 9 by 10% NaOH.

Volatiles were stripped under reduced pressure and the residue was dissolved in water, brought to pH 2 by 2.5N HCl and the solution evaporated to dryness. The crude product was slurried in ethanol (60 ml), collected by filtration and dried, to give 2.75 g (12.1 mmole, 46%) white solid.

$^1$H NMR 6 (DMSO): 7.70 (d, 1H, Ph), 7.60–7.20 (m, 6H, Ph, $NH_2^+$), 4.77 (m, 1H, C1-H), 3.66 (AB q, 2H, $CH_2$), 3.14 (m, 1H, C3-H), 2.85 (m, 1H, C3-H'), 2.40 (m, 1H, C2-H), 2.22 (m, 1H, C2-H') ppm.

EXAMPLE 56

(rac)-N,N-di-(2-Acetamido)-1-aminoindan.HC1.$H_2O$

A mixture of (rac)-1-aminoindan (10.0 g, 75.1 mmole), 2-chloroacetamide (14.8 g, 159.1 mmole), $NaHCO_3$ (15.8 g) in water (200 ml) was stirred under reflux for 3 hrs, cooled to RT and filtered. The solid was dried, slurried in methanol, filtered and dried. The free base was converted to the HCl salt by isopropanolic HCl (5 ml) in ethanol (120 ml); further treatment with water afforded the title product as a hydrate, 5.2 g (18.3 mmole, 24%), mp: 148°–150° C.

Anal. calc. for $C_{13}H_{13}ClN_3O_2.H_2O$: C, 51.74; H, 6.68; N, 13.92.

Found: C, 50.96; H, 6.45; N, 14.16.

$^1$H NMR 6 (DMSO): 7.92 (br s, 2, $CONH_2$), 7.62 (br s, 2H, $CONH_2$), 3.58 (d, 1H, Ph), 7.48–7.25 (m, 3H, Ph), 5.04 (m, 1H, C1-H), 3.95 (d, 2H, $CH_2$), 3.75 (d, 2H, $CH_2$), 3.10 (m, 1H, C3-H), 2.95 (m, 1H, C3-H'), 2.46 (m, 1H, C2-H), 2.36 (m, 1H, C2-H') ppm.

MS: 248 ($MH^+$, 67), 231 ($MH^+-NH_3$, 15), 203 ($MH^+-HCONH_2$, 8) 132 (100), 117 (47).

IR (KBr): 3390, 3220, 3088, 1713, 1688, 1400, 1377, 1215, 723, 691 cm$^{-1}$.

EXAMPLE 57

(rac)-N-(l-Indanyl)-aminoacetonitrile.HCl

A mixture of (rac)-1-aminoindan (5.0 g, 37.6 mmole), 2-chloroacetonitrile (2.84 g, 37.6 mmole), $NaHCO_3$ (3.5 g) in ethanol (20 ml) was stirred under reflux for 3 hrs, filtered hot, and the filtrate was evaporated to dryness. The residue was treated with $Et_2O$ (20 ml, ½ hr, RT) and filtered; the filtrate was evaporated to dryness and the oily residue was taken up in 60 ml 1:1 toluene: $H_2O$ mixture, and the pH of the aqueous phase was adjusted to 7.5. The organic layer was separated and evaporated to dryness. The free base thus obtained was dissolved in $CH_2C_2$ (15 ml) and converted to the hydrochloride with isopropanolic HCl. The solid product was collected by filtration and dried, to give 4.5 g (17.9 mmole, 48%), mp: >250° C.

Anal. calc. for $C_{11}H_{13}ClN_2$: C, 63.31: H, 6.28; N, 13.42.

Found: C, 63.01; H, 6.22; N, 13.34.

$^1$H NMR δ (DMSO): 7.77 (d, 1H, Ph), 7.42–7.25 (m, 3H, Ph), 4.80 (m, 1H, C1-H), 4.35 (s, 2H, $CH_2$), 3.16 (m, 1H, C3-H), 2.88 (m, 1H, C3-H'), 2.40 (m, 1H, C2-H), 2.28 (m, 1H, C2-H') ppm.

MS: 173 ($MH^+$,8), 146 ($MH^+$-CN, 100), 117 (35).

IR (KBr): 2972, 2936, 2910, 2721, 2631, 2569, 2432, 1582, 1445, 1372, 1022, 758 cm$^{-1}$.

EXAMPLE 58

N-Acetyl-6-nitro-1-aminoindan

To an ice-cooled suspension of (rac)-N-acetyl-1-aminoindan (Ex. 17, 17.5 g, 0.1 mole) in nitromethane (165 ml), was added dropwise a nitrating mixture ($H_2SO_4$, $HNO_3$, $H_2O$) while the temperature was kept between 80° C. and 20° C. Stirring was continued for 1.5 hours in the ice-bath and the mixture was then poured on to a mechanically stirred mixture of ice (500 g) and water (1300 ml), stirring being continued for 1 hour. The suspension was filtered, the white solid washed with water and dried (14.05 g, 63.9%). It is sufficiently pure for hydrogenation (Ex. 59).

Crystallization from EtOAc/EtOH/Toluene afforded analytically pure compound, mp: 179° C.

Anal. calc. for $C_{11}H_{12}N_2O_3$: C, 59.99; H, 5.59; N, 12.72.

Found: C, 60.10; H, 5.38; N, 12.70.

$^1$H NMR 6 ($CDCl_3$): 8.09 (br, 2H, C5-H, C7-H), 7.35 (d, 1H, C4-H), 5.88 (br d, 1H, CONH), 5.55 (q, 1H, C1-H), 3.07, 2.94 (m, 2H, C3-H, H', 2.71 (m, 1H, C2-H), 2.09 (s, 3H, Me), 1.90 (m, 1H, C2-H') ppm.

MS: 221 ($MH^+$,100).

IR (KBr): 3267, 1643, 1556, 1516 cm$^{-1}$.

EXAMPLE 59

(rac)-6-Amino-N-acetyl-1-aminoindan.HCl.½ $H_2O$.

(rac)-6-Nitro-N-acetyl-1-aminoindan (Ex. 58, 14.0 g, 64 mmole) was hydrogenated in EtOH (1.3 g, 5% Pd/C) for 3.5 hrs. The mixture was filtered through filter aid and the ethanol thoroughly evaporated in vacuo. The solid residue was crystallized from boiling water (100 ml) and the crystallizing mixture refrigerated (for 2 days). The solid was filtered off, washed with cold water and dried (10.65 g, 84.1%), mp: 161° C.

The free base was dissolved in $CH_2Cl_2$ (250 ml) and converted to the hydrochloride by isopropanolic HCl (9.4 g, 61.8 mmole). The crude HCl salt was crystallized from EtOH/EtOAc: 9.9 g (42.1 mmole, 66%), mp: 224°–5° C.

Anal. calc. for $C_{11}H_{15}ClN_2O.½ H_2O$: C, 56.05; H, 6.84; N, 11.88; Cl, 15.04.

Found: C, 56.48; H, 6.55; N, 11.82; Cl, 15.38.

$^1$H NMR 6 ($D_2O$): 7.45 (d, 1H, C4-H), 7.31, 7.29 (s, dd, 2H, C5-H, C7-H), 5.36 (t, 1H, C1-H), 3.07 (m, 1H, C3-H), 2.93 (m, 1H, C3-H'), 2.53 (m, 1H, C2-H), 2.09 (s, 3H, Me), 1.97 (m, 1H, C2-H') ppm. MS: 191 ($MH^+$).

IR (KBr): 1621, 1548 cm$^{-1}$.

EXAMPLE 60

(rac)-1.6-Bis (acetylamino) indan

1-Acetylamino-6-aminoindan (Ex. 59, 1.90 g, 0.01 mole) was stirred with a solution of sodium hydroxide (0.8 g, 0.02 mole) in water (5 ml); ethyl acetate (5 ml) was then added and the mixture ice-cooled, and acetic anhydride (1.3 ml, 0.014 mole) was added slowly, and the mixture stirred for 0.5 hr. The flask was washed down with water, ethyl acetate removed in vacuo and the solid filtered off, washed with water and oven-dried (2.0 g) in vacuo.

The crude solid was crystallized from ethanol (28 ml) Filtration, washing with ice-cold ethanol and vacuum oven-drying gave the title compound (1.54 g, 65.8%), mp: 225°–60° C.

Anal. calc. for $C_{13}H_{16}N_2O_2$: C, 67.22; H, 6.94; N, 12.06.

Found: C, 67.20; H, 6.99; N, 11.76. $^1$H NMR δ ($CDCl_3$): 7.41 (br s, 1H, C7-H), 7.35 (dd, 1H, C5-H), 7.18 (d, 1H, C4-H), 5.74 (br d, 1H, NHCO) 5.44 (q, 1H, C1-H), 3.49 (br d, 1H, ArNHCO), 2.93 (m, 2H, C3-H, H') 2.80 (m, 1H, C2-H), 2.61 (m, 1H, C2-H'), 2.15 (s, 3H, ArNHCOMe), 2.03 (s, 3H, Me) ppm.

MS: 233 (MH+, 45).

IR (KBr): 1676, 1949, 1602, 1551 cm$^{-1}$.

EXAMPLE 61

(rac)-6-Cyano-N-acetyl-1-aminoindan

1-Acetylamino-6-aminoindan (Ex. 59, 11.42 g, 0.060 mole) was mechanically stirred with water (15.5 ml) in an ice-salt bath and treated with conc. hydrochloric acid (15.5 ml, 0.16 mole) to give a uniform thick suspension which was allowed to cool to ca 0° C. It was then treated dropwise with a solution of sodium nitrite (4.46 g, 0.063 mole) in water (9 ml) so that the temperature stayed below 5° C. After complete addition, the mixture was neutralized by the portionwise addition of sodium carbonate (3.1 g). The resulting solution was added in portions to a previously warmed (65° C.) solution prepared from KCN (9.45 g, 0.145 mole) and CuCN (6.94 g, 0.078 mole) in water (23 ml). The suspension was heated for 15 min, then cooled to 40° C, and the solid was collected by filtration, washed with water, dried and extracted with acetone (100 ml). The latter was evaporated to dryness and the residue purified by flash column chromatography (silica, EtOAc:CH$_2$Cl$_2$ 2:1). The crude product was crystallized from iPrOH to give 7.50 g (37.5 mmole, 62.5%) of a yellow crystalline solid, mp: 175°–6° C.

Anal. calc. for C$_{12}$H$_{12}$N$_2$O: C, 71.98; H, 6.04; N, 13.99. Found: C, 71.97; H, 6.03; N, 13.85.

$^1$H NMR δ (CDCl$_3$): 7.55 (br s, 1H, C7-H), 7.49 (dd, 1H, C5-H), 7.32 (d, 1H, C4-H), 5.97 (br d, 1H, CONH), 5.49 (q, 1H, C1-H), 3.04 (m, 1H, C3-H), 2.92 (m, 1H, C3-H'), 2.64 (m, 1H, C2-H), 2.06 (s, 3H, Me), 1.85 (m, 1H, C2-H') ppm.

IR (KBr): 2227, 1645, 1557 cm$^{-1}$.

EXAMPLE 62

(rac)-6-Carboxamido-N-acetyl-1-aminoindan (rac)-6-Cyano-N-acetyl-1-aminoindan (Ex. 61, 2.50 g, 0.0125 mole) was suspended in ethanol (15 ml) and treated with 25% sodium hydroxide (0.63 ml, 0.005 mole). The mixture was warmed to 40° C. and 30% hydrogen peroxide solution (6.5 ml) added in small portions while the temperature was kept at 40°–50° C. The mixture was stirred for 3 hrs, neutralized with 5% sulfuric acid (4.5 ml, pH 6), cooled to 20° C., filtered, and the white solid washed with water. It was dissolved in acetic acid (10 ml) at 40° C., filtered through "hiflo", and washed with acetic acid (2×2 ml). The filtrate was warmed to 70° C., treated with water (35 ml) and cooled; the solid was filtered off, washed with acetic acid/water 5:30 v/v and finally water, and dried to give 2.0 g (9.2 mmole, 73%), mp: 250°–2° C.

Anal. calc. for C$_{12}$H$_{14}$N$_2$O$_2$: C, 66.04; H, 6.47; N, 12.83. Found: C, 66.14; H, 6.51; N, 12.78.

$^1$H NMR δ (DMSO): 8.24 (d, 1H, MeCONH), 7.92 (br s, 1H, ArCONH), 7.74 (d, 1H, C5-H), 7.72 (s, 1H, C7-H), 7.29 (d, 1H, C4-H), 7.25 (br s, 1H, ArCONH), 5.29 (br q, 1H, C1-H), 2.94 (m, 1H, C3-H), 2.81 (m, 1H, C3-H'), 2.41 (m, 1H, C2-H), 1.89 (s, 3H, Me), 1.77 (m, 1H, C2-H') ppm.

MS: 437 (MMH+, 10), 236 (MNH+$_4$, 100), 219 (MH+, 10).

IR (KBr): 1654, 1554, 1409 cm$^{-1}$.

EXAMPLE 63

(rac)-6-Ethoxycarbonyl-N-acetyl-1-aminoindan (rac)-6-Cyano-N-acetyl-1-aminoindan (Ex. 61, 2.575 g, 0.013 mole) was suspended in ethanol (10 ml) and a mixture of 98% sulfuric acid (4 ml) and ethanol (4 ml) was added. The mixture was stirred (internal temp. 80° C.) overnight and poured into ice water (120 ml) with stirring. The thick grey slurry was filtered and the grey solid filtered off, washed thoroughly with water and dried in vacuo at 50° C. The crude product was crystallized from EtOAc, then from HOAc/water and dried, to give 1.5 g (6.1 mmole, 47%), mp: 146–7° C.

Anal. calc. for C$_{14}$H$_{17}$NO$_3$: C, 67.99; H, 6.93; N, 5.67. Found: C, 67.78; H, 6.97; N, 5.78.

$^1$H NMR δ (CDCl$_3$): 7.94 (m, 2, C5-H, C7-H), 7.29 (d, 1H, C4-H), 5.69 (br d, 1H, NHCO), 5.51 (q, 1H, C1-H), 4.37 (dq, 2H, Et), 3.01 (m, 1H, C3-H), 2.89 (m, 1H, C3-H'), 2.66 (m, 1H, C2-H), 2.05 (s, 3H, Me), 1.83 (m, 1H, C2-H'), 1.40 (t, 3H, Et) ppm.

MS: 248 (MH+, 100), 247 (M$^{30}$, 25), 189 (MH+-MeCONH$_2$, 50), 188 (M+-MeCONH$_2$, 70), 202 (MH+-EtOH, 25), 201 (M+-EtOH, 10).

IR (KBr): 1711 (ester), 1634, 1558 (amide) cm$^{-1}$.

EXAMPLE 64

(cis)-3-(Methoxycarbonyl)-1-aminoindan.HCl

The title compound was prepared in 70% from phenylsuccinic anhydride, according to the procedure described in J.Med.Chem., 31, 433 (1988), mp: 216°–7° C. Anal. calc. for C$_{11}$H$_{14}$ClNO$_2$: C, 58.02; H, 6.15; N, 6.15; Cl, 15.60 Found: C, 57.82; H, 6.20; N, 6.27; Cl, 15.68

$^1$H NMR δ (DMSO): 8.80 (br s, 3H, NH$_3^+$), 7.75, 7.40 (m, 4H, Ph), 4.70 (t, 1H, C1-H), 4.18 (t, 1H, C3-H), 3.74 (s, 3H, Me), 2.78 (m, 1H, C2-H), 2.26 (m, 1H, C2-H') ppm.

MS: 192 (MH+, 63), 175 (100), 160 (82), 143 (27), 131 (74), 115 (59).

IR (KBr): 3000–2700, 2024, 1744, 1616, 1381, 1289, 1179, 772 cm$^{-1}$.

EXAMPLE 65

(cis)-1-Aminoindan-3-carboxylic acid.HCl

The title compound was prepared in 86% from (cis)-3-(methoxycarbonyl)-1-aminoindan.HCl, according to the procedure described in J.Med.Chem., 31, 433 (1988), mp: 217°–8° C.

Anal. calc. for C$_{10}$H$_{12}$ClNO$_2$: C, 56.21; H, 5.62; N, 6.56;, Cl, 16.53 Found: C, 56.05; H, 5.79; N, 6.80; Cl, 16.71.

$^1$H NMR δ (DMSO): 8.76 (br s, 3H, NH$_3^+$), 7.73, 7.54–7.30 (m, 4H, Ph), 4.67 (br t, 1H, C1-H), 4.06 (t, 1H, C3-H), 2.73 (m, 1H, C2-H), 2.25 (m, 1H, C2-H') ppm.

MS: 178 (MH+, 100), 160 (MH+-H$_2$O, 80), 130 (61), 115 (42).

IR (KBr): 3150-2700, 1963, 1732, 1711, 1481, 1397, 1366, 1188, 875, 773, 752 cm$^{-1}$.

EXAMPLE 66

(rac),(trans)-2-Methyl-N-acetyl-1-aminoindan

The title compound was prepared in 59% yield from (rac),(trans)-2-methyl-1-aminoindan (Ex. 40, 3.0 g) according to the procedure described in Ex. 17, mp: 137° C.

Anal. calc. for C$_{12}$H$_{15}$NO: C, 76.16; H, 7.99; N, 7.40. Found: C, 76.14; H, 8.14; N, 7.49.

$^1$H NMR δ (CDCl$_3$): 7.24 (m, 4H, Ph), 5.64 (br d, 1H, CONH), 5.45 (m, 1H, C1-H), 3.04 (dd, 1H, C3-H), 2.79 (m, 1H, C2-H), 2.59 (dd, 1H, C3-H'), 0.97 (d, 3H, Me) ppm.

MS: 190 (MH+, 45), 146 (MH+-CH₃COH, 11), 130 (M+-CH₃CONH₂, 100).

IR (KBr): 3300, 2939, 1646; 1547, 1370, 745 cm⁻¹.

EXAMPLE 67

(rac), (cis)-2-Methyl-N-acetyl-1-aminoindan

To a solution of $Ac_2O$ (1.45 g, 14.2 mmole) in toluene (12 ml), was added dropwise a solution of (rac), (cis)-2-methyl-1-aminoindan (Ex. 39, 1.85 g, 12.6 mmole). The mixture was heated at 90° C. for 15 min, cooled to 70° C., and a solution of 1.1 g KOH in 8.3 ml water was added. The reaction mixture was stirred at ambient temperature for 2 hrs; the solid was collected by filtration, washed with toluene (10 ml), dried and crystallized from hexane:EtOAc, to give 1.85 g (9.8 mmole, 78%), mp: 146°–7° C.

Anal. calc. for $C_{12}H_{15}NO$: C, 76.16; H, 7.99; N, 7.40

Found: C, 76.16; H, 7.80; N, 7.45.

¹H NMR δ (CDCl₃): 7.24 (m, 4H, Ph), 5.70 (br d, 1H, CONH), 5.15 (t, 1H, C1-H), 3.10 (dd, 1H, C3-H), 2.57 (dd, 1H, C3-H'), 2.22 (m, 1H, C2-H), 2.10 (s, 3H, Ac), 1.30 (d, 3H, Me) ppm.

MS: 190 (MH+, 7), 131 (48, 130 (100).

EXAMPLE 68

(R)-N-Trifluoroacetyl-1-aminoindan

The title compound was prepared in 67% yield from (R)-1-aminoindan (3.35 g, 25.2 mmole) and trifluoroacetic anhydride (5.75 g, 27.4 mmole), as described in Ex. 67; mp: 152°–3° C.

Anal. calc. for $C_{11}H_{10}NO$: C,

Found:

¹H NMR δ (CDCl₃): 7.28 (m, 4H, Ph), 6.50 (br s, 1H, CONH), 5.49 (q, 1H, C1-H), 3.05, 2.94 (m, 2H, C3-H, H'), 2.65 (m, 1H, C2-H), 1.92 (m, 1H, C2-H') ppm.

MS: 230 (MH+, 0.3), 229 (M+, 0.4), 228 (6), 117 (72), 116 (100).

EXAMPLE 69

(rac)-N-(4-(di-n-Propylsulfamoyl)benzoyl)-1-aminoindan

The title compound was prepared in 63% yield from (rac)-1-aminoindan (10.0 g, 75.2 mmole) and 4-(di-n-propylsulfamoyl) benzoyl chloride (16.3 g, 53.6 mmole, prepared from probenecid and SOCl2) via a procedure analogous to that described in Ex. 46, followed by crystallization from hexane:EtOAc, mp: 124°–5° C.

Anal. calc. for $C_{22}H_{28}N_2O_3S$: C, 65.97; H, 7.05; N, 7.0; S, 8.0

Found: C, 65.70; H, 6.91; N, 7.03; S, 7.70.

H NMR δ (CDCl₃): 7.94–7.80 (m, 4H, Ph), 7.35 (m, 1H, Ph), 7.32–7.20 (m, 3H, Ph), 6.44 (br d, 1H, CONH), 5.69 (q, 1H, C1-H), 3.08 (m, 4H, CH₃CH₂CH₂N), 3.06 (m, 1H, C3-H), 2.95 (m, 1H, C3-H'), 2.71 (m, 1H, C2-H), 1.96 (m, 1H, C2-H'), 1.54 (m, 4H, CH₃CH₂CH₂N), 0.86 (t, 6H, Me)ppm.

MS: 401 (MH+, 100), 371 (39), 285 (56), 236 (9).

EXAMPLE 70

2-(1-Indanamino)-N-isopropylethanesulphonamide.HCl

2-Chloroethanesulphonyl chloride (8.15 g, 50 mmoles) in ether (60 ml) was cooled to –2° C., stirred mechanically and treated dropwise with isopropylamine (12.75 ml, 150 mmoles) in ether (40 ml). After complete addition (15 min) the mixture was allowed to stir at –2° C. for 30 min. and allowed to warm to 20° C. 1-Indanamine (6.71 g 50 mmoles) in ether (20 ml) was added dropwise followed by stirring for one hour. The mixture was filtered and the solid isopropylamine hydrochloride washed thoroughly with ether. The combined filtrates were evaporated to dryness and the residue (11.3 g) was chromatographed on silica gel (257 g) using ethyl acetate/hexane 4:1 v/v. The fractions immediately following the yellow band were evaporated to give the base (2.85 g). The base was dissolved in isopropanol (20 ml) and converted to the HCl salt with 24% isopropanolic HCl (16 ml). The combined solution was then treated slowly with ether (ca 40 ml) and the solid was filtered, washed with cold ethanol/ether and finally ether. It was dried in vacuo at 5020 C. and left in vacuo for several days (3.0 g, 9.4 mmole, 19%). Melting point 177.2°–177.8° C.

Anal. calc. for $C_{14}H_{23}ClN_2O_2S$: C, 52.73; H, 7.27; N, 8.78, Cl, 11.12; S, 10.06.

Found: C, 52.52; H, 7.35; N, 8.84; S, 10.88: Cl, 10.88. ¹H NMR δ (DMSO): 9.70 (br, 2H), 7.75 (d, 1H), 7.45 (d, 1H), 7.28–7.41 (m, 3H), 4.83 (brt 1H), 3.31–3.62 (m, 3H), 3.10–3.30 (m, 3H), 2.89 (m, 1H), 2.43 (m, 1H), 2.22 (m, 1H), 1.13 (d,6H)ppm

MS: 566 (2MH, 40), 283 (MH, 100), 132 (20), 117 (15).

IR (KBr): 3128, 2976, 2824, 1322, 1121 cm⁻¹.

EXAMPLE 71

2-(1-Indanamino)-N-(1-indanyl)ethanesulphonamide.HCl

2-Chloroethanesulphonyl chloride (2.1 g, 20 mmoles) in ether (10 ml) was cooled to 10° C. and while stirred mechanically, treated dropwise with 1-indanamine (10.2 ml, 80 mmoles) in ether (40 ml). After the addition, the mixture was stirred at RT for 2.5 hours. It was then filtered, the white solid (indanamine hydrochloride) washed thoroughly with ether and the combined filtrates evaporated to a thick yellow oil. Purification by chromatography (EtOAc:hexane 2:1) afforded the free base which was taken up in ether (20 ml) and treated carefully with a 24% solution of HCl in isopropanol (ca 3 ml). The sticky mass gradually broke up on trituration in ether, filtered to give a white solid (3.06 g) crystallized from EtOH/Et2O and dried, (1.31 g, 3.3 mmole, 17%).

Melting point 186°–187° C.

Anal. calc. for $C_{20}H_{25}ClN_2O_2S$: C, 61.13; H, 6.41; N, 7.13; S, 8.16: Cl, 9.02:

Found: C, 60.83; H, 6.51; N, 7.28.

¹H NMR δ (DMSO): 9.82 (br s, 2H), 8.01 (d, 1H), 7.78 (d, 1H), 7.2–7.4 (m, 8H), 4.79 (q, 1H), 4.84 (br s, 1H), 3.68 (m, 2H), 3.32 (m, 2H), 3.17 (m, 1H), 2.77,2.92 (m, 3H), 2.56,2.46 (m), 2.25 (m, 1H), 1.88 (m, 1H)ppm.

MS: 357 (MH, 100), 132 (98), 117 (18).

IR (KBr): 3074, 2940, 1446, 1327, 1148 cm⁻¹.

EXAMPLE 72

(R,R)-2-(1-Indanamino)-N-(1-indanyl)ethanesulphonamide.HCl

The free base (2.8 g) was obtained by the same procedure as in Example 71 using (R)-1-aminoindan (10.66 g, 80 mmole). It was triturated with hexane and the resultant solid recrystallized from ethanol (15 ml), to give a white crystalline solid (1.185 g). The free base was then dissolve in warm abs. ethanol (32 ml) and 0.1N HCl(33.5 ml, 3.31 mmole) was added. The solution was evaporated in vacuo at 55° C. (bath). It was evaporated again with ethanol, the residual white foam dissolved in warm ethanol (10 ml) and diluted with ether (20 ml). The solid was collected by filtration, washed with alcohol/ether and ether, and dried to give 1.15 g (2.9 mmole, 8%) of title compound.

Melting point 172°–173° C.

Anal. calc. for $C_{20}H_{25}ClN_2O_2S$: C, 61.13; H, 6.41; N, 7.13: S, 8.16: Cl, 9.02:

Found: C, 60.14; H, 6.40; N, 7.13, S, 8.16; Cl, 8.39.

$^1$H NMR δ (DMSO): 9.76 (br s, 2H), 8.01 (1H), 7.7 (1H), 7.19–7.41 (m, 6H), 4.80 (q, 1H), 4.86 (br m, 1H), 3.68 (m, 2H), 3.3,3.17 (m, 1H), 2.76 (quint) and 2.92 (m, 3H), 2.55 (m, 1H), 2.44 (m 1H), 2.22 (m, 1H), 1.88 (m, 1H)ppm.

MS: 357 (100), 241 (40), 159 (10), 132 (20).

IR (KBr): 3167, 2940, 2719, 1458, 1336, 1144 cm$^{-1}$.

EXAMPLE 73

N,N'-Bis-(1-indanyl)adipamide

Racemic 1-aminoindan (5.7 g, 43 mmole.) in ether (20 ml) stirred in ice, was treated dropwise with adipoyl chloride (1.83 g, 10 mmole) in ether (10 ml). After 30 min. the solid was filtered and slurried with water for 45 min. The insoluble solid was collected, air dried (2.82 g) and crystallized from HOAc/$H_2O$, washed with acetic acid/water (1:1), ethanol and ether and then dried to give 2.26 g (60% title compound. Melting point: 227° C.

Anal. calc. for $C_{24}H_{28}N_2O_2$: C, 76.56; H, 7.50; N, 7.44.

Found: C, 76.35; H, 7.69; N, 7.61.

$^1$H NMR δ (DMSO): 8.17 (d, 1H, NH), 7.14–7.26 (m, 4H, Ar), 5.28 (q, 1H, C1-H), 2.91,2.78 (m, 2H, C3-$H_2$), 2.37 (m, 1H, C2-H), 2.14 (br, 2H, α-$CH_2$), 1.76 (m, 1H, C2-H), 1.56 (br, 2H, β-$CH_2$)ppm.

IR (KBr): 3288, 2936, 1638, 1539, 1256, 749 cm$^{-1}$.

EXAMPLE 74

N,N'-Bis-((R)-1-indanyl)adipamide

This was prepared by the same procedure as in Example 73 starting from (R)-1-aminoindan (5.32 g, 40 mmole), with an additional recrystallization from ethanol (20 ml) and acetic acid (15 ml) to give the white product (2.37 g, 62.9%). Melting point: 244°–7° C.

Anal. calc. for $C_{24}H_{28}N_2O_2$: C, 76.56; H, 7.50; N, 7.44.

Found: C, 76.28; H, 7.59; N, 7.74.

$^1$H NMR δ (DMSO): 8.16 (d, 1H, NH), 7.10–7.30 (m, 4H, Ar), 5.28 (q, 1H, C1-H), 2.92,2.78 (m,m, 2H, C3-$H_2$), 2.36 (m, 1H, C2-H), 2.14 (br, 2H, α-$CH_2$), 1.76 (m, 1H, C2-H), 1.56 (br, 2H, β-$CH_2$)ppm.

MS: 377(MH$^+$, 25), 253 (45), 132 (100).

IR (KBr): 3289, 2959, 1642, 1541, 1254, 745 cm$^{-1}$.

EXAMPLE 75

N,N'-Bis-((R)-1-indanyl)succinamide

This was prepared by the same procedure as in Example 73 starting from (R)-1-aminoindan (8.02 g, 60 mmole) and succinoyl chloride (2.32 g, 14 mmole), to give the white product, (1.30 g, 26.7%). Melting point: 266°–9° C.

Anal. calc. for $C_{22}H_{24}N_2O_2$: C, 75.83; H, 6.94; N, 8.09.

Found: C, 74.50; H, 7.03; N, 8.16.

$^1$H NMR δ (DMSO): 8.22 (d, 1H, NH), 7.10–7.26 (m, 4H, Ar), 5.29 (q, 1H, C1-H), 2.92 (ddd, 2H, C3-H), 2.78 (m, 1H, C3-H), 2.30–2.46 (m, 1H, C2-H and α-$CH_2$), 1.77 (m, 1H, C2-H)ppm.

MS: 349 (MH$^+$, 78), 233 (25), 216 (5), 132 (100).

Examples 76 to 82 exemplify the preparation of compounds of Formulas 2 and 3.

EXAMPLE 76

Racemic N-benzyl-1-aminoindan base

Approximately 22.1 g of HCl gas was introduced into indene (technical grade 90%, 80 g, 0.62 mole) at 25°–30° C. over a period of 4 hours and excess HCl gas was removed under vacuo.

A mixture of 272 ml of toluene and 199.5 g benzylamine was prepared and heated to 90° C. The chlorindan was added dropwise to the mixture over a 30 minute period. The reaction mixture was heated to 115° C for ten hours. The reaction mixture was cooled to ambient temperature and 300 ml of water was added. The resulting heterogeneous mixture was then brought to pH2.2 by the addition of 33% $H_2SO_4$. The phases were separated and the organic layer discarded. The pH of the aqueous layer was adjusted to pH6.0 prior to extraction with 300 ml of toluene. A further 100 ml of toluene was then added and the aqueous phase discarded. The toluene was removed under vacuo from the combined organic layer leaving 104.3 g racemic N-benzyl-1-aminoindan base as an oil (72.5% yield).

$^1$H-NMR (δ,CDCl$_3$): 1.82–1.94 (m,1H), 2.36–2.48 (m,1H), 2.73–2.86 (m,1H), 2.96–3.70 (m,1H), 3.75–4.30 (m,2H), 4.30 (t,J=3 HZ,1H), 7.16–7.44 (aromatic,9H)ppm

M.S. (CI,CH$_4$)MH$^+$224.0

EXAMPLE 77

R-(+)-N-benzyl-1-aminoindan-L-mandelate mono ethanoate

To a solution of racemic N-benzyl-1-aminoindan base (61.6 g, 0.276 mole) in absolute ethanol (208 ml) at 50° C., a solution of L-(+)-mandelic acid (22.2 g, 0.146 mole) in absolute ethanol (100 ml) was added dropwise. The reaction mixture was heated to 75° C. whereupon complete dissolution had occurred, and then cooled slowly to 10° C. over a 3 hour period. The crystals formed were collected by filtration and recrystallized in 260 ml absolute ethanol by repeating the heating and cooling steps. The crystals were collected by suction filtration and dried in a vacuum oven at 40°–50° C. producing an 46.5 g of the title compound (40% yield).

m.p. 94°–97° C.

[α]D22=+38.90° (1.86% acetone)

$^1$H-NMR (δ, aceton d$_6$): 1.11 (t,J=6 Hz,3Hethanol) 2.10–2.30 (m,2H), 2.66–2.80 (m,1H), 2.97–3.08 (m,1H), 3.55 (q,J=6 Hz,2Hethanol), 3.89 (s,2H), 4.42–4.46 (m,1H), 4.75 (s,1H), 7.04–7.50 (aromatic,14H)ppm

M.S. (CI, NH$_3$) MH$^+$224.1

EXAMPLE 78

S-(−)-N-benzyl-1-aminoindan-L-mandelate mono ethanolate

The title compound is prepared by the same process of Example 77, with the exception that D-(−)-mandelic acid was used as the resolving agent. Similar yields were obtained.

melting point 92°–94° C.

[α]D22=−40.10° (1.71 aceton)

$^1$H-NMR (δ, aceton d$_6$) 1.11 (t,J=6 Hz,3Hethanol) 2.10–2.20 (m,1H), 2.20–2.34 (m,1H), 2.68–2.82 (m,1H), 2.96–3.09 (m,1H), 3.56 (q,J=6 Hz,2Hethanol), 3.94 (s,2H), 4.43–4.48 (m,1H), 4.79 (s,1H)ppm.

EXAMPLE 79

R-(+)-N-benzyl-1-aminoindan (base)

R-(+)-N-benzyl-1-aminoindan-L-mandelate mono ethanolate (57.7 g), prepared as in Example 77, was suspended in a mixture of 70 ml water and 75 ml toluene. The mixture was stirred vigorously and adjusted to pH13–14 by the addition of 40% NaOH solution. The extraction was repeated with further 50 ml of toluene. The toluene was removed in vacuo from the combined organic layers to provide the title compound as a colorless oil (99.5% yield). [α]D22=+3.7° (10.9%, methanol)

EXAMPLE 80

S-(−)-N-benzyl-1-aminoindan (base)

The title compound was prepared by the process of Example 79, except that S-(−)-N-benzyl-1-aminoindan-D-mandelate mono ethanolate was used as the starting material. [α]D22=−4.0° (10.9%, methanol)

EXAMPLE 81

R-(−)-1-aminoindan (R)-N-benzyl-1-aminoindan (5.73 g, 26.8 mmole), as prepared in Example 79, was dissolved in 60 ml absolute ethanol and ethanolic HCl solution 19% w/w (6.2 g, 32.1 mmole, 1.2 equivalents) was added to this solution. The mixture was reduced using hydrogen gas in the presence of a 5% Pd/C catalyst (0.45 g, 3% on a dry basis) at 75° C. and 3 atm. hydrogen pressure for a period of 7 hours. The volatiles were removed by evaporation in vacuo. The solid material was partitioned between 50 ml water and 30 ml toluene. The pH of the aqueous phase was adjusted to pH2.3 by adding 10% NaOH solution and the phases were then separated. Toluene (50 ml) was added to the aqueous phase and the pH increased to 12.5 with 45% NaOH. The organic phase was separated and the aqueous phase re-extracted with 30 ml toluene. The combined toluene phases were evaporated in vacuo and the crude compound purified by distillation, (20 mmHg/117.5°–119° C.) to give 2.57 g R-(−)-1-aminoindan (72% yield). Optical purity 99.4% by chiral chromatography.

EXAMPLE 82

S-(+)-1-aminoindan

The title compound was prepared by the process of Example 81, except that (S)-N-benzyl-1-aminoindan was used as the starting material.

B. Experimental Examples

EXAMPLE 1

Effect of 1-Aminoindans in an Experimental Model of Dopaminergic Hypofunction

Experiments 1A and 1B. Alpha-MpT- induced hypokinesia in hypoxic rat

Procedure

Experiment 1A

Wistar male rats, 15–19 month-old, were exposed to a single hypoxic episode which is assumed to decrease the level of dopamine in the brain. Four to five rats were kept for six hours in a glass chamber equipped with an inlet and outlet tubes for the admission of an atmosphere of premixed nitrogen (92%) and oxygen (8w) at a flow rate of 3L/min. Control rats received room air from a compressed tank under similar conditions.

1-R-aminoindan HCl (hereinafter R-AI) or deprenyl (an MAO B inhibitor) were administered to the rats immediately following the conclusion of the hypoxic episode at the standard dose of 0.5 mg/kg/Day for 70–80 days. Given the different ratios of amine to salt in these compounds, the dose of free amine (the active species) corresponding to 0.5 mg/kg salt is actually 0.39 mg/kg for R-AI and 0.42 mg/kg for deprenyl. The drugs were administered by gavage, using a special syringe equipped with rounded tip that could be directed into the stomach. The dose was contained in 0.3–0.5 mL of distilled water.

The rats were pretreated for 70–80 days with daily doses of the test drugs and received intra-peritoneal (i.p.) α-MpT (α-methyl-p-tyrosine) at a dose of 100 mg/kg in 0.3–0.5 mL saline. Controls received saline. α-MpT is assumed to inhibit the formation of L-Dopa from tyrosine and, consequently the formation of dopamine itself. Lack of central dopamine is expressed as hypokinesia.

Following the injection of α-MpT, motor activity was recorded for the duration of 10 hours.

Locomotion scores were taken in seven fully-computerized cages (26×25 cm) having a grid of infra-red beams at 4 cm-intervals.

Crossing of a beam initiated an electric signal which was fed into a computer. The number of crossings over a given period provided a measure of locomotion. The records gave two data categories: (a) "small movements" originating in stationary activities such as grooming and scratching and (b) "big movements" originating in ambulation and recorded as the simultaneous crossing of more than two beams. "Total movements" include both categories.

Counts of motor activity in the presence of α-MpT were related as percent with respect to counts in its absence in the corresponding control group (unlesioned or hypoxia-lesioned). Motor activity counts of drug-treated rats were related to the hypoxia saline-treated as 100%. All behavioral tests were performed 90–120 min. after administration of the last dose of the test compound.

Results

Experiment 1A.

Figure 2:
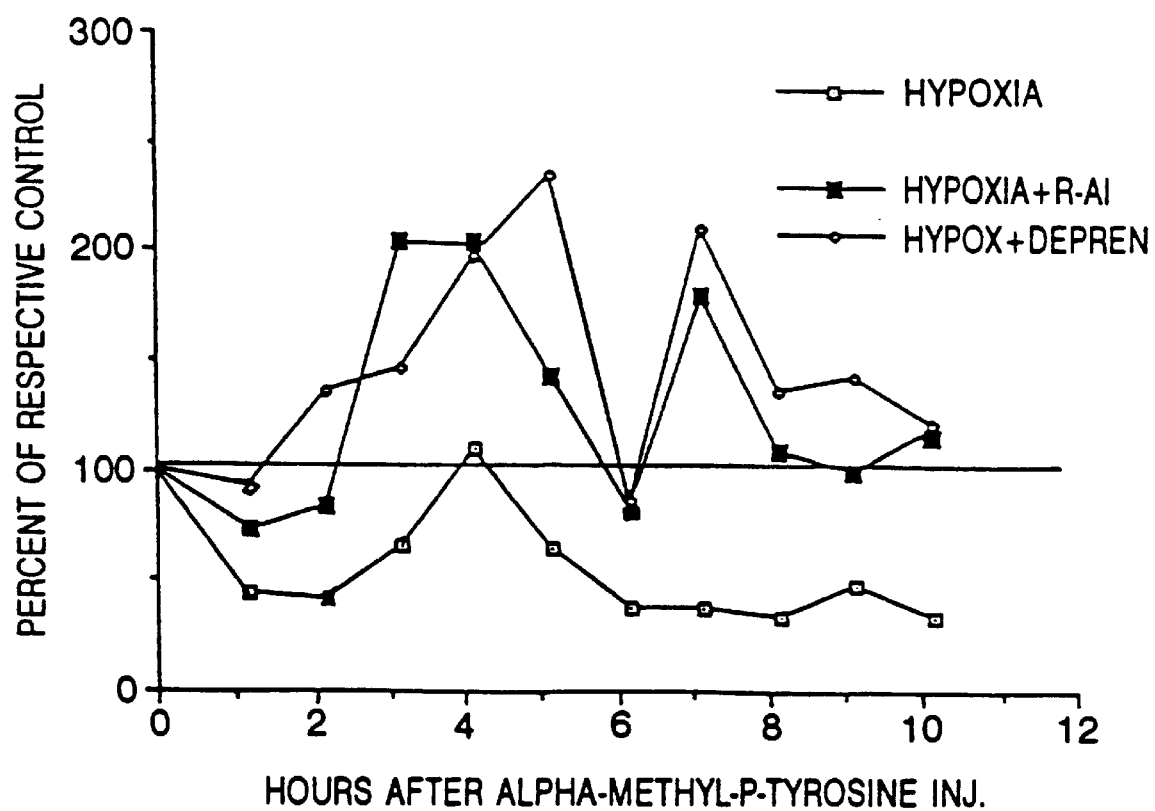
FIG. 2: Experiment 1A: α-MpT-induced hypokinesia in hypoxic rat. Effect of the drug treated group as compared to the untreated hypoxic group. X-axis: hours after α-MpT injection. Y-axis: percent of respective control recorded as total movements.

"Total movements" after α-MpT are given in Table 1 and FIGS. 1 and 2. In FIGS. 1 and 2, hours after alpha-methyl-p-tyrosine injection are given on the x-axis and percent response as compared to the relevant control is given on the y-axis. FIG. 1 shows the effect the hypoxic episode had as compared to the control animals, whereas FIG. 2 shows the effect the drug treated group compared to the untreated hypoxic group.

TABLE 1

Locomotor activity after α-MpT treatment, recorded as total movements.

| Hour | Control | Hypoxia | Hypoxia + R-AI | Hypoxia + deprenyl |
|---|---|---|---|---|
| 1 | 77 ± 11 | 39 ± 12 | 67 ± 8 | 88 ± 23 |
| 2 | 92 ± 20 | 36 ± 8 | 79 ± 12 | 131 ± 30 |
| 3 | 115 ± 44 | 61 ± 15 | 198 ± 60 | 141 ± 26 |
| 4 | 186 ± 44 | 105 ± 42 | 196 ± 17 | 191 ± 45 |
| 5 | 168 ± 46 | 60 ± 28 | 138 ± 19 | 229 ± 40 |
| 6 | 61 ± 23 | 32 ± 15 | 77 ± 17 | 82 ± 14 |
| 7 | 84 ± 22 | 32 ± 19 | 173 ± 30 | 204 ± 7 |
| 8 | 114 ± 23 | 29 ± 15 | 104 ± 18 | 131 ± 23 |
| 9 | 114 ± 40 | 43 ± 17 | 95 ± 16 | 137 ± 21 |
| 10 | 103 ± 31 | 29 ± 15 | 114 ± 41 | 116 ± 22 |

Control rats underwent two phases of hypokinesia. The first at hour 1–2 after α-MpT followed by full recovery and rebound at hour 3. Then, another phase of hypokinesia at hours 6–7 followed by full recovery to control level at hours 7–8.

In the hypoxic group, the decrease in motor activity was more pronounced during the first phase at hours 1–2, with some recovery at hour 4, followed by a second phase of hypokinesia which lasted till hour 10 with no signs of recovery.

Hypoxic rats that had been pretreated with R-AI or deprenyl behaved similarly (FIG. 2). In either case the two-phase cyclic pattern of depression-rebound-depression found for α-MpT-treated hypoxic controls could be observed. However, the level of activity of the R-AI and deprenyl-treated groups was much higher than the corresponding control group controls. In fact, in either case the levels and fluctuations of motor activity were not different from hypoxia-unlesioned control rats that had received α-MpT alone.

Figure 3:
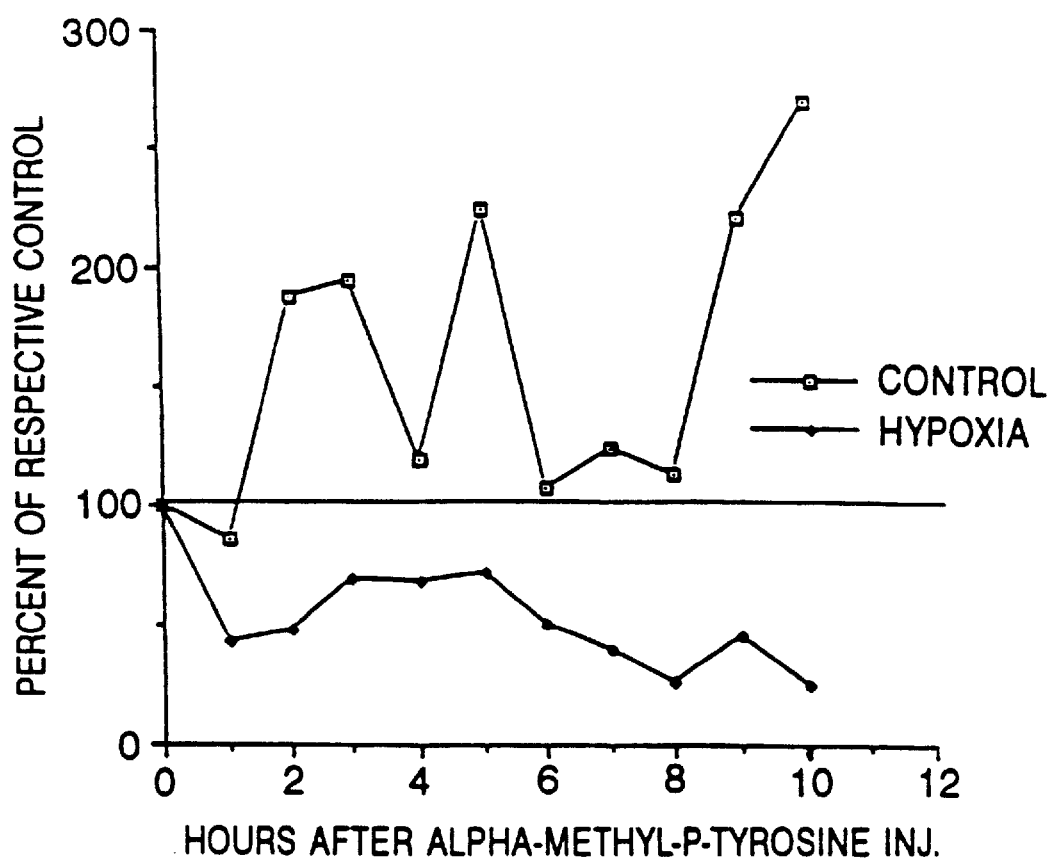
FIG. 3: Experiment 1A: α-MpT-induced hypokinesia in hypoxic rat. Effect of the hypoxic episode as compared to control animals. X-axis: hours after α-MpT injection. Y-axis: percent of respective control recorded as big movements.
Figure 4:
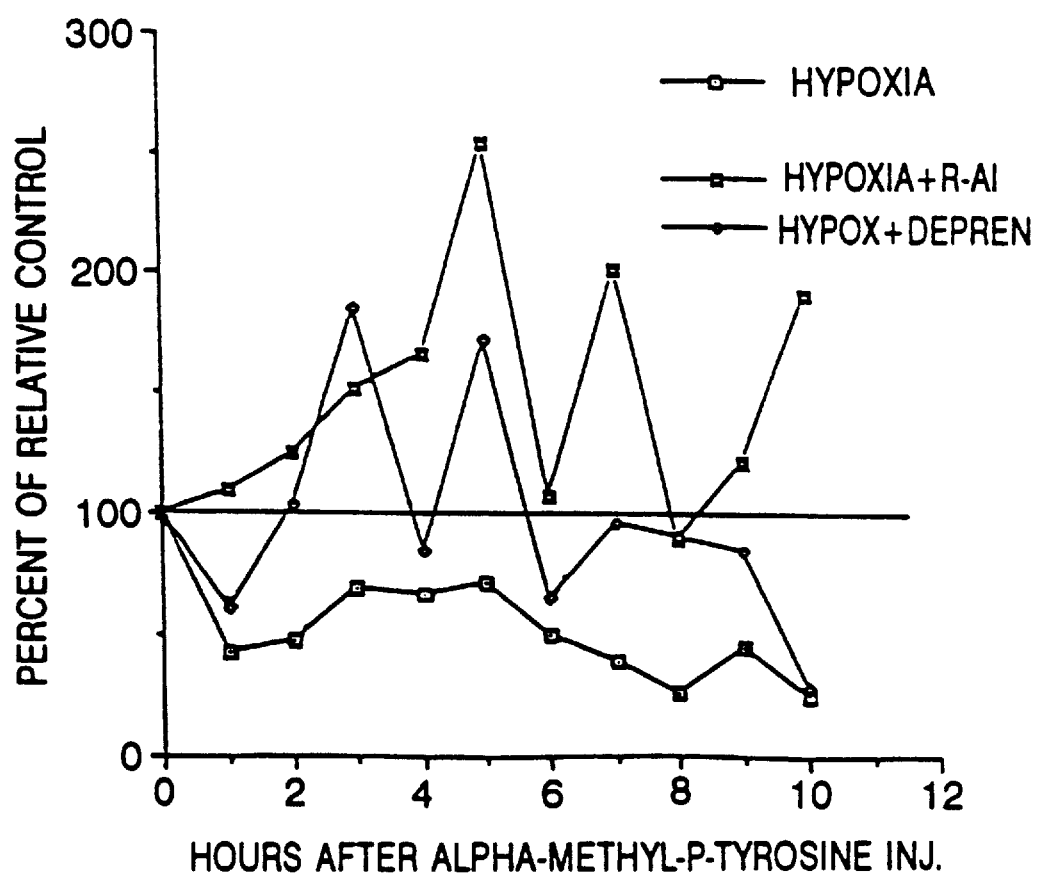
FIG. 4: Experiment 1A: α-MpT-induced hypokinesia in hypoxic rat. Effect of the drug treated group as compared to the untreated hypoxia group. X-axis: hours after α-MpT injection. Y-axis: percent of respective control recorded as big movements.

The score of "big movements" is given in Table 2 and FIGS. 3 and 4, the Figures having the same axes as FIGS. 1 and 2.

TABLE 2

Locomotor activity after α-MpT treatment, recorded as big movements.

| Hour | Control | Hypoxia | Hypoxia + R-AI | Hypoxia + deprenyl |
|---|---|---|---|---|
| 1 | 85 ± 25 | 43 ± 11 | 109 ± 27 | 61 ± 15 |
| 2 | 187 ± 56 | 48 ± 16 | 125 ± 29 | 103 ± 22 |
| 3 | 195 ± 94 | 69 ± 34 | 151 ± 36 | 184 ± 39 |
| 4 | 119 ± 71 | 67 ± 40 | 165 ± 40 | 85 ± 34 |
| 5 | 224 ± 93 | 71 ± 43 | 254 ± 55 | 171 ± 61 |
| 6 | 107 ± 64 | 50 ± 24 | 201 ± 50 | 65 ± 17 |
| 7 | 123 ± 37 | 39 ± 20 | 201 ± 50 | 96 ± 29 |
| 8 | 113 ± 46 | 26 ± 15 | 89 ± 23 | 91 ± 40 |
| 9 | 220 ± 72 | 45 ± 18 | 121 ± 52 | 84 ± 23 |
| 10 | 269 ± 106 | 25 ± 10 | 190 ± 34 | 29 ± 10 |

N = 7–10 in a group.
Results are given as Mean ± SEM.

α-MpT produced a paradoxical effect in control rats, with outbursts of hyperkinesia which lasted for as long as ten hours after an initial small decrease in activity which may not be significant.

In contradistinction, hypoxia-lesioned rats were hypokinetic for as long as ten hours with no signs of recovery. R-AI corrected the hypokinetic syndrome in the hypoxia group, bringing the level of activity almost to that seen in the control hypoxia-unlesioned group. There were at least three outbursts of hyperactivity during he ten hour-observation period. Deprenyl was less effective in this respect, with outbursts of hyperactivity alternating with periods of depression.

Experiment 1B.

The procedure of Experiment 1A was repeated with the following changes:

(1) Animal: 11–14 month-old rats.

(2) Drug treatment: R-AI and deprenyl at a daily dose of 0.3 mg/Kg in 0.2 mL. The drugs were given i.p.

(3) Duration of the treatment: 21 days.

(4) Dose of α-MpT: 70 mg/Kg.

Results

Experiment 1B

Figure 5:
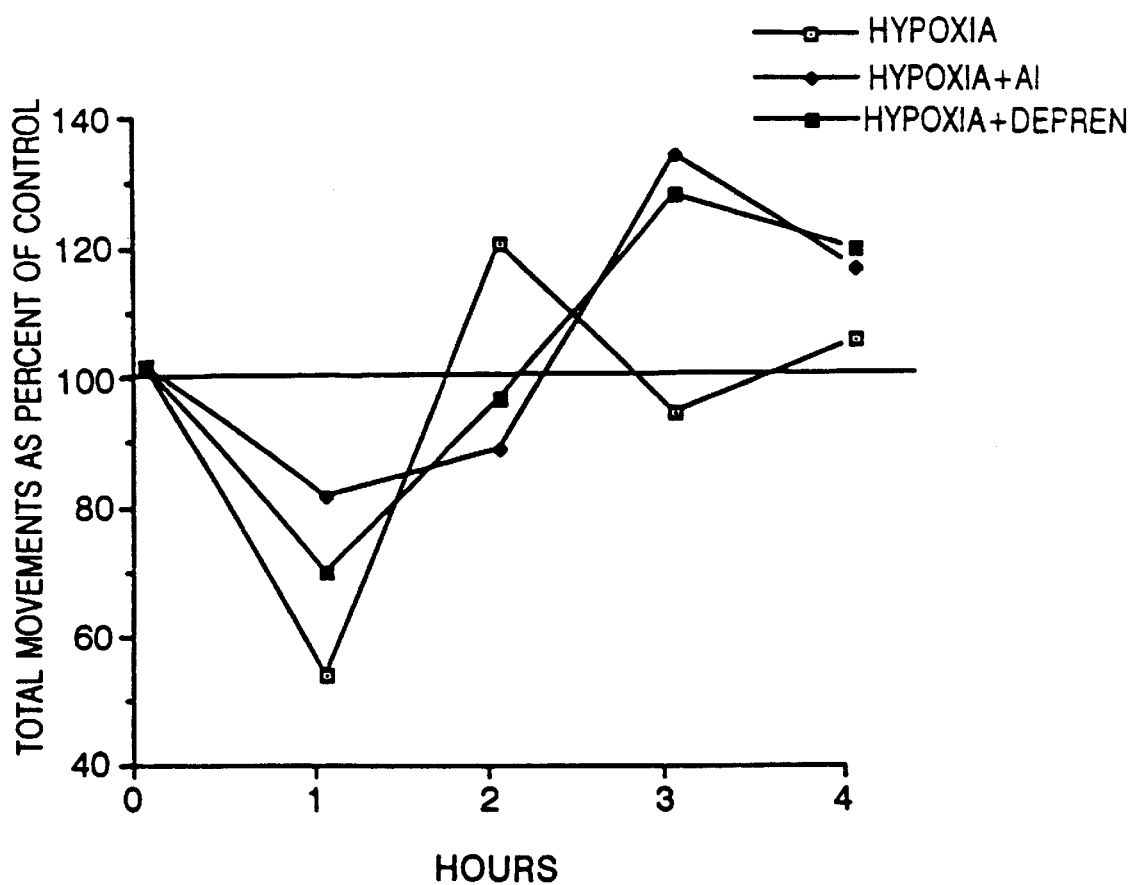
FIG. 5: Experiment 1B: α-MpT-induced hypokinesia in hypoxia rat. Effect of the drug treated group as compared to the untreated hypoxia group. X-axis: hours after α-MpT injection. Y-axis: percent of respective control recorded as total movements.
Figure 6:
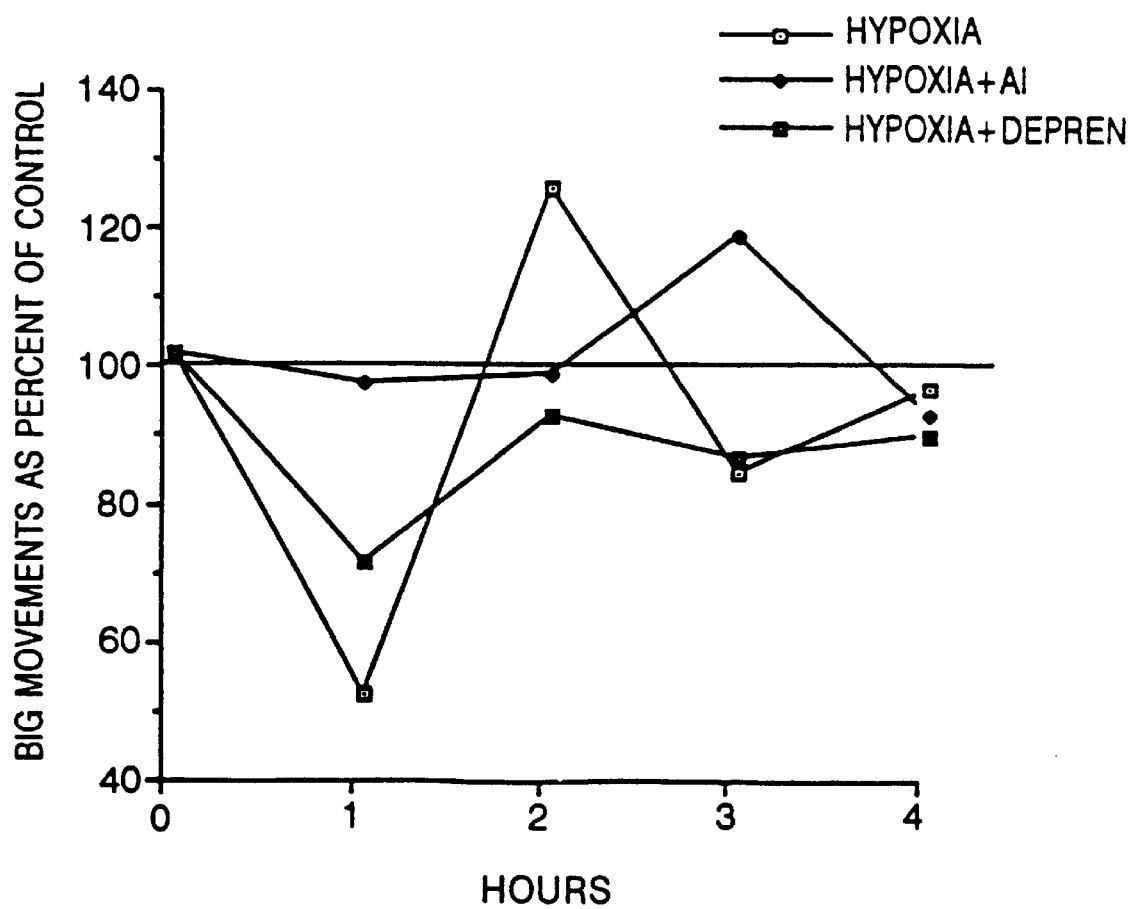
FIG. 6: Experiment 1B: α-MpT-induced hypokinesia in hypoxia rat. Effect of the drug treated group as compared to the untreated hypoxia group. X-axis: hours after α-MpT injection. Y-axis: percent of respective control recorded as big movements.

Total movements after α-MpT are given in Table 3 and FIG. 5. The score of big movements is given in Table 4 and FIG. 6. In FIGS. 5 and 6 hours after alpha-methyl-p-tyrosine injection are given on the x-axis and percent response as compared to the relevant control is given on the y-axis. FIG. 5 shows the fate of the groups treated with R-AI or deprenyl as compared to the hypoxic group over the first four hours, with respect to total movements. FIG. 6 shows the same data with respect to big movements. Antagonism to α-MpT by R-AI and deprenyl is best perceived within the 2–4 hours after the α-MpT injection as shown in FIGS. 5 and 6. Note that in the first hour the level of motor activity (total movements) of R-AI treated rats was almost normal (80%), but not in the hypoxic group (50%). None of the drugs was active at the second phase of hypokinesia, except deprenyl which showed some activity.

TABLE 3

Locomotor activity after α-MpT Treatment, recorded as total movements.

| Hour | Control | Hypoxia | Hypoxia + R-AI | Hypoxia + deprenyl |
|---|---|---|---|---|
| 1 | 69 ± 7 | 52 ± 10 | 80 ± 15 | 68 ± 9 |
| 2 | 90 ± 13 | 119 ± 12 | 87 ± 13 | 95 ± 11 |
| 3 | 117 ± 35 | 93 ± 24 | 132 ± 25 | 126 ± 22 |
| 4 | 93 ± 24 | 104 ± 8 | 115 ± 24 | 118 ± 20 |
| 5 | 92 ± 12 | 80 ± 14 | 65 ± 28 | 83 ± 24 |
| 6 | 65 ± 14 | 72 ± 6 | 76 ± 11 | 78 ± 9 |
| 7 | 71 ± 15 | 84 ± 7 | 65 ± 7 | 56 ± 7 |
| 8 | 75 ± 16 | 69 ± 8 | 40 ± 6 | 85 ± 13 |
| 9 | 79 ± 0 | 66 ± 11 | 72 ± 12 | 111 ± 12 |
| 10 | 86 ± 4 | 69 ± 6 | 69 ± 18 | 61 ± 12 |

TABLE 4

Locomotor activity after α-MpT treatment, recorded as big movements.

| Hour | Control | Hypoxia | Hypoxia + R-AI | Hypoxia + deprenyl |
|---|---|---|---|---|
| 1 | 75 ± 6 | 51 ± 10 | 96 ± 18 | 70 ± 10 |
| 2 | 55 ± 14 | 124 ± 20 | 97 ± 16 | 91 ± 19 |
| 3 | 114 ± 42 | 83 ± 28 | 117 ± 45 | 85 ± 19 |
| 4 | 51 ± 16 | 95 ± 16 | 91 ± 11 | 88 ± 23 |
| 5 | 60 ± 18 | 52 ± 7 | 67 ± 11 | 87 ± 11 |
| 6 | 49 ± 21 | 60 ± 8 | 58 ± 14 | 67 ± 8 |
| 7 | 66 ± 14 | 69 ± 10 | 68 ± 15 | 62 ± 9 |
| 8 | 63 ± 16 | 77 ± 10 | 34 ± 6 | 70 ± 9 |
| 9 | 55 ± 19 | 90 ± 11 | 84 ± 19 | 132 ± 24 |
| 10 | 56 ± 13 | 63 ± 6 | 44 ± 6 | 54 ± 13 |

N = 4–7 in a group.
Results are given as Mean ± SEM.

Discussion of Experiments 1A and 1B

Experiment 1A demonstrates the ability of R-AI to correct a syndrome of dopaminergic hypofunction associated with Parkinson's Disease to an extent at least comparable, or in some instances better than that of deprenyl. This effect was also evident in the first 2–4 hours of Experiment 1B. This experiment was carried out over a shorter period than Experiment 1A, using a lower dosage of R-AI on a separate population of animals Both these experiments indicate that 1-aminoindans of formula 1 have a role in the treatment of Parkinson's Disease.

Experiment 1C. The procedure of Experiment 1A was repeated with the following changes:

(1) Animal: 11–14 month-old rats.
(2) Drug treatment: Test compounds were administered at the dosages indicated, as a single i.p. dose 1 hour prior to α-MpT (150 mg/kg).
(3) Animals were placed in an activity cage immediately after drug administration and total movements were measured for the following 10 hours.

The drugs tested with reference to the relevant Chemical Example No were:

(R)-1-aminoindan, (RAI), 0.8 mg/kg, n=5
4,5-dimethoxy-1-aminoindan, (31), 0.8 mg/kg, n=6
6-fluoro-(R)-1-aminoindan, (FAI), 1.2 mg/kg, n=3
(R)-N-acetyl-1-aminoindan, (18), 0.8 mg/kg, n=2
(R)-6-hydroxy-1-aminoindan, (35), 1.2 mg/kg, n=3

Figure 8:
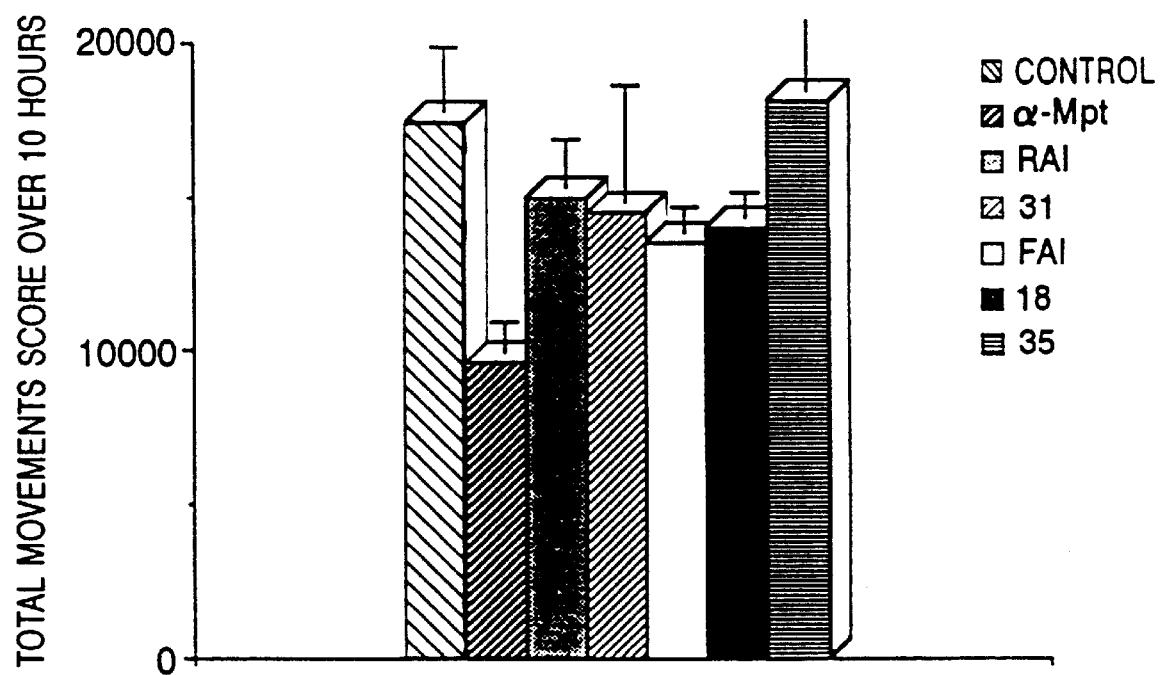
FIG. 8: Experiment 1C: α-MpT-induced hypokinesia in hypoxic rat. Effect of the drug treated group as compared to the untreated hypoxic group. Y-axis: total movements over 10 hours. The drugs tested are identified in the figure legend using codes, identified as follows: (R)-1-aminoindan, (RAI), 0.8 mg/kg, n=5; 4,5-dimethoxy-1-aminoindan, (31), 0.8 mg/kg, n=6; 6-fluoro-(R)-1-aminoindan, (FAI), 1.2 mg/kg, n=3; (R)-N-acetyl-1-aminoindan, (18), 0.8 mg/kg, n=2; (R)-6-hydroxy-1-aminoindan, (35), 1.2 mg/kg, n=3.

The results are shown in FIG. 8 from which it can be seen that all compounds tested antagonized the α-Mpt-induced hypokinesia.

EXAMPLE 2

Effect of 1-Aminoindans on Amphetamine-Induced Stereotype Behavior in Hypoxic Rat Procedure Experiment 2A.

Wistar male rats, 15–19 month-old, were exposed to a single hypoxic episode as described above. R-AI or deprenyl were administered to the rats at the same dose and method used in Example 1A. Rats pretreated for 29 days with daily doses of the test drugs (0.5 mg/kg), received a sub-cutaneous (s.c.) injection of D-amphetamine sulfate at a dose of 0.1 smg/kg. D-amphetamine is known to cause an enhancement of the effects of CNS dopamine by a mechanism involving dopamine release, and blockage of its uptake and its metabolism by MAO. The behavioral manifestation of amphetamine action is a stereotypic pattern of lateral head movements.

Counts of lateral head movements were taken over two successive intervals of 1 min each, 45–60 min after the injection of amphetamine and then averaged.

Experiment 2B.

The procedure of the second Experiment 2B was similar to the one used in Experiment 2A with the following changes:

1) Animals: 12 month-old rats.
2) Drug treatment: R-AI and deprenyl at a daily dose of 0.3 mg/kg in 0.2 mL. The drugs were given by i.p. injection.
3) Duration of the treatment: 14 days.

Experiment 2C.

The procedure of Experiment 2A was repeated with the following changes:

1) None of the rats had previously been exposed to a hypoxic episode.

2) Test compounds were administered as a single treatment, at a dose of 1.2 mg/kg (base equivalents) 60 minutes prior to D-amphetamine sulphate (0.6 mg/kg s.c.).

3) Scores of No of head movements were taken 45 minutes after amphetamine injection.

The compounds tested were, referring to the relevant Chemical Example No.:

(R)-N-acetyl-1-aminoindan (18),
(R)-4,5-dimethoxy-1-aminoindan (29),
(R)-1-aminoindan (R-AI),
(R)-6-hydroxy-1-aminoindan (35),
(R)-6-fluoro-1-aminoindan (R-FAI),
(S)-4,5-dimethoxy-1-aminoindan (30).

Results

The results of Experiment 2A are shown in Table 5. Table 5 shows the total number of lateral head movements per minute for each of the experimental groups.

TABLE 5

| Control untreated | Hypoxia untreated | Hypoxia + R-AI | Hypoxia + deprenyl |
|---|---|---|---|
| 63 ± 4 | 84 ± 2** | 108 ± 3** | 76 ± 3* |
| n = 8 | n = 8 | n = 7 | n = 6 |

Mean ± SEM
*p ≦ 0.05 **p ≦ 0.001 (with respect to corresponding control)

In the hypoxic group, pretreatment with R-AI produced a significant potentiation of the stereotypic behavior induced by amphetamine with respect to their respective control (hypoxia and amphetamine). Under the same conditions, deprenyl pretreatment did not potentiate amphetamine-induced stereotypicity. Drug-untreated hypoxic rats were more active than drug-untreated control rats, owing perhaps to the development of dopamine hypersensitivity in response to presynaptic dopamine deficiency.

The same test was repeated on day 60 of drug treatment in order to check for a possible tolerance to the test compounds that might have developed over time. The results were not different from those found on day 29. In Experiment 2B pretreatment with R-AI produced a significant potentiation of stereotypic behavior as measured by lateral head movements, but not deprenyl. This is shown in Table 6.

TABLE 6

| Control untreated | Hypoxia untreated | Hypoxia + R-AI | Hypoxia + deprenyl |
|---|---|---|---|
| 63 ± 5 | 79 ± 3* | 92 ± 3** | 77 ± 3 |
| n = 12 | n = 12 | n = 6 | n = 7 |

*p ≦ 0.05 **p ≦ 0.01

Figure 9:
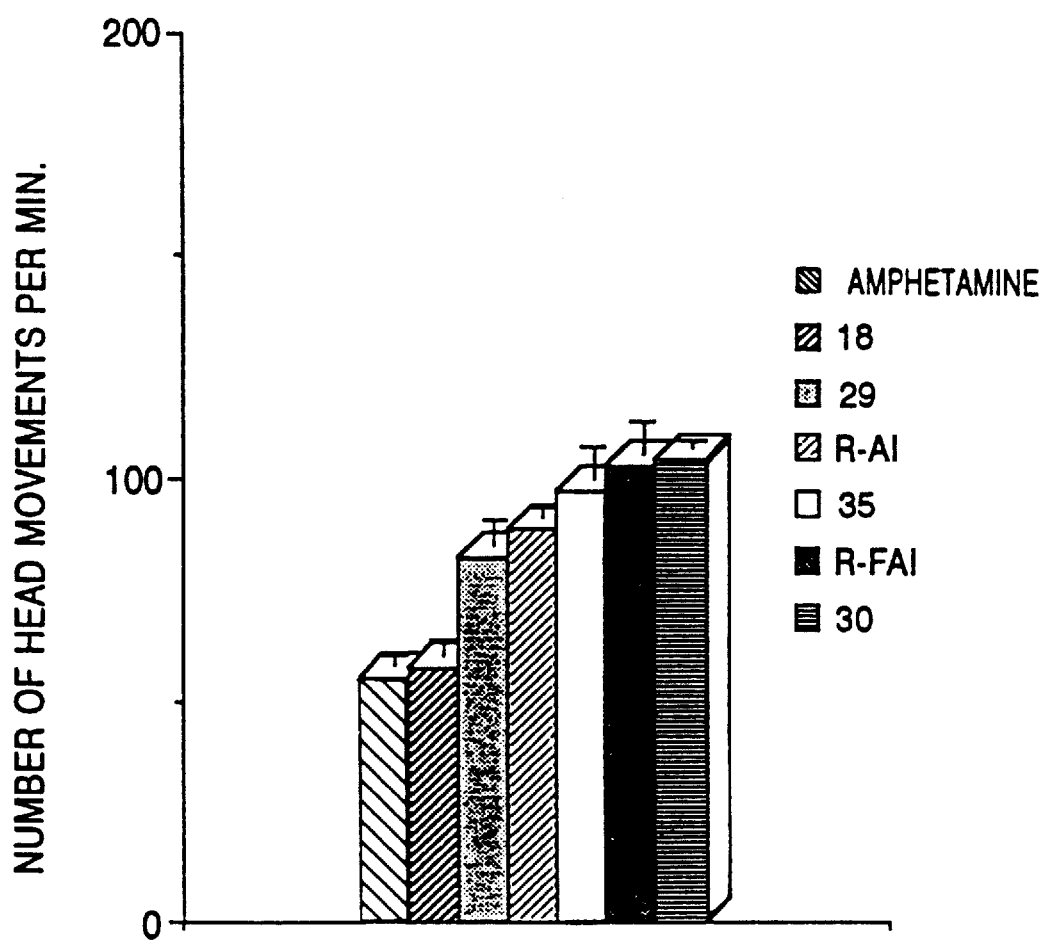
FIG. 9: Experiment 2C: Effect of 1-Aminoindans on Amphetamine-Induced Stereotype Behavior in Rats. Y-axis: number of head movements per minute, measured 45 minutes after amphetamine injection. The drugs tested are identified in the figure legend using codes, identified as follows: (R)-N-acetyl-1-aminoindan (18), (R)-4,5-dimethoxy-1-aminoindan (29), (R)-1-aminoindan (R-AI), (R)-6-hydroxy-1-aminoindan (35), (R)-6-fluoro-1-aminoindan (R-FAI), (S)-4,5-dimethoxy-1-aminoindan (30).

The results of Experiment 2C are shown in FIG. 9 from which it can be seen that all compounds tested produced a potentiation of the stereotypic behavior induced by amphetamine.

Discussion of Experiments 2A and 2B

Stereotypic behavior is not caused by amphetamine itself, but by the enhancement of the effect of released dopamine through a combination of effects: release, uptake inhibition and MAO inhibition.

Both Experiments 2A and 2B have demonstrated that R-AI, unlike deprenyl, can greatly enhance the effect of amphetamine.

Since the effect of potentiation of stereotype behavior is assumed to be mediated by CNS dopamine, then pretreatment with R-AI must have been instrumental in the restoration of presynaptic dopamine levels after the hypoxic insult, thus further demonstrating that 1-aminoindans have a role in correcting the symptoms associated with Parkinson's Disease.

EXAMPLE 3

Experimental Model for Cognitive Function:
Passive Avoidance Test in Hypoxic Rat Procedure Experiment 3A:

Wistar male rats, 15–19 month-old, were exposed to a single hypoxic episode as described above. R-AI or deprenyl were administered to the rats at the same dose and method used in the α-MpT model. The passive avoidance test was performed on day 13 after initiation the drug treatment. The apparatus consisted of a lit chamber that can be separated from a dark chamber by a sliding door. At training, a rat is placed in the lit chamber for 30 seconds, then the door is opened. The rat moves to the dark chamber after a short delay—the latency, that is recorded. Upon entry into the dark chamber, the door is shut closed and a 0.3-mA footshock is delivered for 3 seconds by a Grass S-88 stimulator. Retention of the experience is determined after 48 hours by repeating the test and recording the latency to an arbitrary maximum of 300 seconds. Longer latencies are ascribed to retention of memory and improved cognition.

Results

The latency, in seconds, is shown in Table 7. Pretreatment of the hypoxia rats with R-AI improved their performance to control level. In contrast, deprenyl-treated hypoxia rats showed no improvement.

TABLE 7

| Group | before electroshock | 48h after electroshock |
|---|---|---|
| Control | 75 ± 21 | 217 ± 34 |
| Hypoxia | 59 ± 6 | 143 ± 33* |
| Hypoxia + R-AI | 53 ± 6 | 245 ± 33* |
| Hypoxia + deprenyl | 53 ± 7 | 153 ± 37 |

(1) Results are latency of response expressed in seconds as Mean ± SEM.
(2) n = 11–13 rats in a group.
(3) *p ≦ 0.05 relative to corresponding control by the student's t-test.

Experiment 3B: Water Maze Working Memory Test

The apparatus used consists of a circular water tank 160 cm in diameter filled with water to a depth of 38 cm. The water was made cloudy by the addition of milk powder. A clear Plexiglass 15 cm platform, supported by a movable stand rest on the bottom of the tank was submerged to a depth of 2 cm from the water surface. Normally a swimming rat cannot perceive the location of the platform but it may recall it from a previous experience and training, unless it suffers from some memory impairment. The time taken to locate the platform is measured in seconds and referred to as the latency. During the experiment all orientational cues such as ceiling lights etc. remained unchanged. Longer latencies are observed with rats with some impairment to their memory.

As described above the rats were exposed to a hypoxia episode and R-AI was administered to rats daily as described in Experiment 1A.

Each rat was given two trails a day for four days, entering the pool from the same point of entry each day. The position of the platform was changed daily to one of four predetermined positions. Each rat was tested twice each day over the four days, referred to as runs 1 and 2 on sessions I–IV. Initially the rat was placed on the platform for 60 seconds. It was then removed and placed at the point of entry and allowed a maximum of 120 seconds to locate the platform (run 1). The second run for that day followed 60 seconds later (run 2). In the second run the rat is expected to find the platform much sooner, having benefitted from its earlier experience. Performance is assumed to represent the rate of acquisition from the more recent experience, hence this is termed working memory. The average latency of run 1 in four sessions on four different days was then related to the corresponding parameter of run 2. The smaller the ratio of run 1/run 2, the better the short range learning score.

Results

Figure 7:
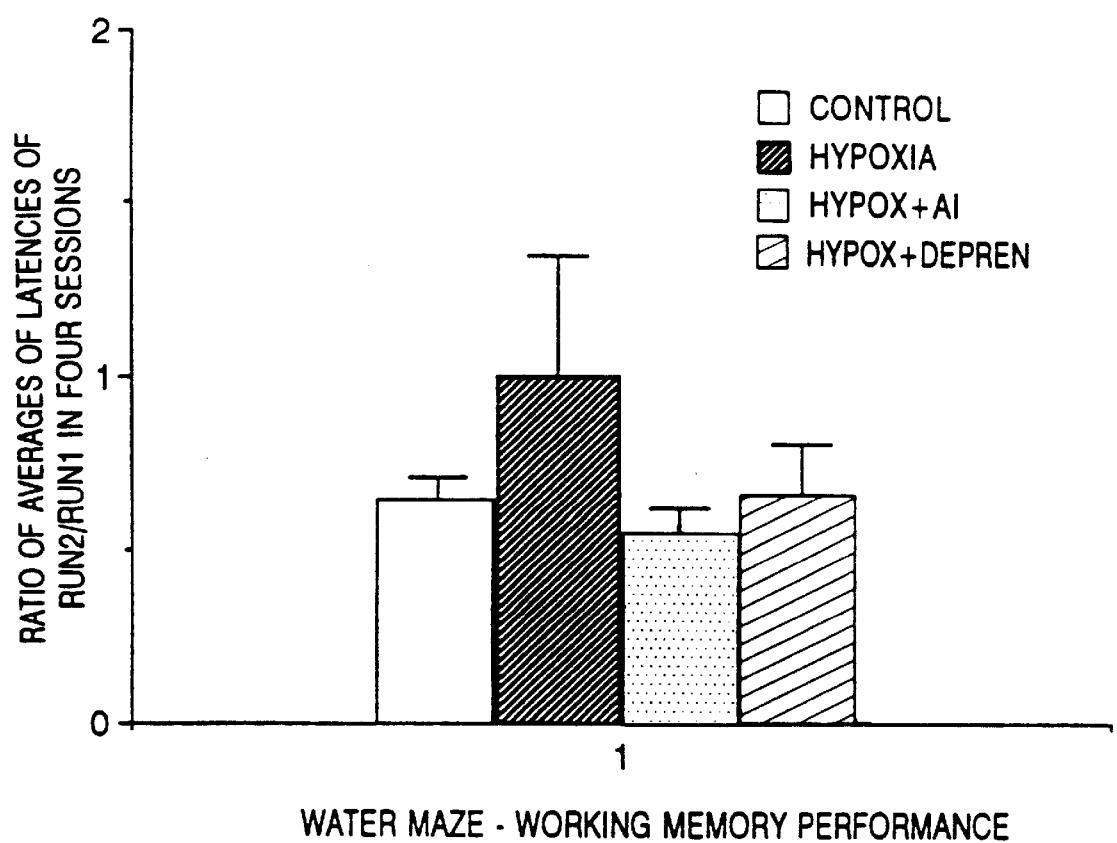
FIG. 7: Experiment 3B: Water Maze Working Memory Test. X-axis: water maze—working memory performance. Y-axis: ratio of averages of latencies of run2/run1 in four sessions. Bars are, from left to right: control; hypoxia; hypoxia+AI; hypoxia+deprenyl

The results are given in Table 8 and FIG. 7. Performance of the hypoxia group was inferior to that of the control group in sessions I–III, but did not improve in session IV.

Among the R-AI-treated hypoxia group tended towards superior performance to the hypoxia group.

Table 8. Performance of hypoxia-lesioned rats in the water maze-working memory test after pretreatment with 1-R-aminoindan (AI) or deprenyl at the dose of 0.5 mg/kg/day for the duration of 60 days. The data are the latencies in seconds±SEM that it took a given group to locate a submerged and invisible platform the location of which was shifted from one session to the other. The time interval between sessions was one day, and that between successive runs was 60 seconds. (n=7–8 rats per group)

TABLE 8

| Group | Session I | | Session II | | Session III | | Session IV | |
|---|---|---|---|---|---|---|---|---|
| | Run 1 | Run 2 | Run 1 | Run 2 | Run 1 | Run 2 | Run 1 | Run 2 |
| Control | 43 ± 13 | 20 ± 8 | 11 ± 2 | 9 ± 2 | 9 ± 2 | 6 ± 1 | 11 ± 3 | 7 ± 1 |
| Hypoxia | 47 ± 19 | 50 ± 17 | 31 ± 12 | 20 ± 10 | 29 ± 6 | 10 ± 2 | 8 ± 2 | 15 ± 8 |
| Hypoxia + AI | 50 ± 16 | 25 ± 12 | 25 ± 8 | 14 ± 3 | 19 ± 5 | 14 ± 3 | 15 ± 5 | 6 ± 2 |
| Hypoxia + deprenyl | 42 ± 16 | 40 ± 17 | 42 ± 18 | 35 ± 16 | 32 ± 15 | 8 ± 2 | 19 ± 6 | 12 ± 4 |

Discussion of Experiments 3A and 3B

In learning and memory tests, normal performance in the passive avoidance response is generally related to unimpaired cholinergic function. For example, treatment with the potent muscarinic antagonist scopolamine results in amnesia in humans and an inferior performance in passive avoidance in rats. Tacrine, a cholinesterase inhibitor, has been reported recently to be of value in the restoration of memory in senile dementia patients of the Alzheimer type and kainic acid-lesioned rats.

In addition, chronic administration of tacrine improved performance in the passive avoidance test of anoxia-lesioned rats (see FIG. 7 in Speiser et al. 1989 Neuropharm. 28(12) 1325–1332). These findings demonstrated that R-AI can correct a syndrome of cognitive dysfunction and loss of memory which are prevalent in dementia's such as senile dementia, Parkinson-type dementia and dementia of the Alzheimer's type.

EXAMPLE 4

Effect Of Aminoindans on Neutrotrauma

Experiment 4A.

The effect of 1-aminoindans following closed head injury in rats

Methods

1. Induction of trauma.

Head trauma was induced in male rats under ether anesthesia by a well calibrated drop weight device. The weight falls over the exposed skull, covering the left cerebral hemisphere, 1–2 mm lateral to the midline in the midcoronal plane. A detailed description of this method is given in Shohami et al. J. Neurotrauma 1993 10(2) 109.

2. Evaluation of motor function.

One hour after the induction of trauma the rats were tested by a set of criteria to evaluate their neurological status. These criteria are listed in Shohami supra. as is the scoring method thereof which is referred to as the Neurological Severity Status (NSS).

Points are given based on the absence of these criteria, thus a high NSS indicates a highly traumatized rat whereas a low NSS indicates a non-traumatized rat. Consequently a high ΔNSS indicates that a good recovery has occurred. The rats were re-evaluated 24 hours after the induction of trauma.

3. Evaluation of brain oedema.

After the second evaluation of motor function, the animals were sacrificed and the brains were removed. A piece of tissue was weighed to yield a wet weight (WW), then dried in an oven for 24 hours at 95C and re-weighed to yield a dry weight(DW). Percentage water content in the tissue was calculated as (WW-DW)×100/WW.

4. Drug treatment.

1-R-aminoindan (RAI) was dissolved in water and injected into the rats by an intra-peritoneal route at a dose of 0.1 mg/kg at 0,4,8, and 12 hours post-trauma. The control group received similar volumes of water at the same times.

Results.

Table 9 below shows the NSS scores taken 1 hour and 24 hours post-trauma. ΔNSS is the change in NSS over that time.

TABLE 9

|  | NSS | | | % water in |
|---|---|---|---|---|
|  | 1 hr | 24 hr | ΔNSS | the brain |
| Control (n = 6) | 16.6 | 12.3 | 4.3 ± 0.5 | 85.4 ± 0.4 |
| RAI (n = 6) | 16.8 | 8.3 | 8.5 ± 0.5* | 81.5 ± 0.5** |
| SAI (n = 6) | 16.4 | 10.8 | 5.6 ± 0.5 | 84.0 ± 0.8 |

*$p \leq 0.01$ (Mann-Whitney test)
**$p \leq 0.001$ (t-test)

From Table 9 it is clear that the 1-aminoindanes have a role in improving post-trauma motor function and in decreasing the trauma induced cerebral oedema. This latter point is more relevant when considering that the normal non-traumatized brain has a water content of 78.5% (see Shohami et al. page 116, FIG. 2). Thus the activity of RAI shown above represents a 50% reduction in trauma-induced oedema.

Experiment 4B.

The method of Experiment 1A was repeated with RAI and 1-S-aminoindan (SAI) being administered at a 0.1 mg/kg dosage once a day for a period of 14 days. NSS assessment was performed at 1 hour, 24 hours, 7 days and 14 days. The results are shown in Table 10 below from which it can be seen that aminoindans have an improved effect on post trauma motor function when administered over a prolonged period and that RAI can restore almost complete motor function to a traumatized rat.

TABLE 10

|  | NSS at 1 hr | ΔNSS at 24 hr | ΔNSS at 48 hr | ΔNSS at 7 d | ΔNSS at 14 d |
|---|---|---|---|---|---|
| Control (n = 5 | 15.2 ± 0.2 | 4.0 ± 0.3 | 4.8 ± 0.5 | 5.6 ± 0.2 | 6.4 ± 0.2 |
| RAI 35 (n = 6) | 17.7 ± 0.5 | 7.3 ± 0.8 | 9.3 ± 0.8 | 11.8 ± 0.5 | 14.0 ± 0.4 |
| SAI (n = 6) | 16.6 ± 0.3 | 5.5 ± 0.4 | 6.8 ± 2.7 | 8.3 ± 1.0 | 9.5 ± 1.0 |

Experiment 4C.

The method above was repeated using a range of doses of RAI from 0.03 mg/kg to 3 mg/kg. The results are shown in the same manner as above in Table 11 from which it is evident that a maximal response was observed at 0.3 mg/kg and this level of response was retained thereafter.

TABLE 11

| RAI | NSS | | | % water in |
|---|---|---|---|---|
| mg/kg | 1 hr | 24 hr | ΔNSS | the brain |
| Control | 16.9 | 12.7 | 4.2 ± 0.4 | 83.6 ± 0.4 |
| 0.03 | 16.3 | 10.4 | 5.9 ± 0.3 | 81.0 ± 0.7 |
| 0.1 | 16.2 | 10.4 | 5.8 ± 0.4 | 81.8 ± 0.6 |
| 0.3 | 16.6 | 8.5 | 8.1 ± 0.5 | 81.8 ± 0.7 |
| 1.0 | 16.8 | 8.8 | 8.0 ± 0.5 | 81.5 ± 0.5 |
| 3.0 | 16.4 | 7.8 | 8.6 ± 0.7 | 81.9 ± 0.7 |

Experiment 4D: The method of Experiment 4A was repeated using a 1 mg/kg dosage of RAI at the time of trauma induction (t=0) and at different times thereafter e.g. 4 hr, 8 hr and 12 hr after trauma induction, i.e. a total of only two treatments. An addition control comparison was performed administering RAI at 0, 4, 8 and 12 hours. The results are shown in Table 12 below from which it can be seen that both regardless of the number and timing of administration, all treated groups showed the same degree of improvement of both NSS and oedema.

TABLE 12

| Times of RAI administration | ΔNSS | % water in the brain | n |
|---|---|---|---|
| Control | 4.8 ± 0.3 | 83.3 ± 0.6 | 6 |
| 0 | 8.8 ± 10.8 | 81.2 ± 0.6 | 6 |
| 0 + 4 h | 8.0 ± 1.0 | 81.2 ± 0.4 | 6 |
| 0 + 8 h | 8.0 ± 0.1 | 81.8 ± 0.5 | 6 |
| 0 + 12 h | 8.7 ± 0.6 | 80.7 ± 0.5 | 6 |
| 0,4,8,12 h | 8.2 ± 0.7 | 81.5 ± 0.5 | 6 |

Experiment 4E:

In order to obtain an idea as to the effective "therapeutic window" during which RAI can be given and still be effective, Experiment 4A was repeated giving RAI at 1 mg/kg 1, 2 or 3 hours post induction of head trauma. As shown in Table 13 below RAI was still effective even if given 3 hours after the induction of head trauma.

TABLE 13

| Time of RAI administration (post head trauma) | ΔNSS | % water in the brain | n |
|---|---|---|---|
| Control | 4.8 ± 0.3 | 84.5 ± 0.4 | 7 |
| + 1 h | 8.4 ± 0.6 | 81.7 ± 0.4 | 8 |
| + 2 h | 7.0 ± 0.5 | 82.5 ± 0.4 | 8 |
| + 3 h | 7.4 ± 0.5 | 81.8 ± 0.5 | 8 |

Rate of MAO inhibition

The brains of some rats from each experimental group in Exp. 1 (chronic treatment of 80 days) and Exp. 2 (acute treatment of 14 days) were ex vivo analyzed for MAO-A and MAO-B activity. Results are shown in Table 14 below.

TABLE 14

| Treatment | % inhibition of MAO A | | % inhibition of MAO B | |
|---|---|---|---|---|
| | chronic treatment | acute treatment | chronic treatment | acute treatment |
| R-AI | 6 | 13 | 44 | 21 |
| deprenyl | 23 | 18 | 90 | 89 |

Chronic or acute treatment of R-AI does not have an effect on MAO-A activity. These findings also indicate that only chronic treatment of RAI can partially inhibit the MAO-B activity. As expected, acute or chronic treatment with deprenyl can strongly and selectively inhibit the activity of MAO-B.

EXAMPLE 5

Anticonvulsive Activity of Aminoindans

Compounds provided herein were screened for their ability to protect against electrical and chemically induced convulsions. The standard electrically induced test model is the Maximal electroshock (MES) model. This model is used to show efficacy for antiepileptic agents against generalized and partial seizures. The standard model for chemically induced seizures is the subcutaneous pentylenetetrazol (s.c.Met) seizure threshold test model. This model is used to show efficacy for agents against absence seizures. In these studies, convulsions were administration in rats after oral (p.o.) administration, and/or in mice after intraperitoneal (i.p.) administration of the compound. Both the MES and s.c.Met models are described in E. A. Swinyard et al., in "Antiepileptic Drugs" E. R. H. Levy et al., Raven Press, New York (1985). The methods described therein were followed in the present examples.

Results

The results of the MES model are shown in Table 15 and where relevant the results of scMet in Table 16. All results in the Tables are in mg/kg. Compounds are deemed to be within the scope of the invention if they displayed an ED50 of less than 200 mg/kg in at least one of the models.

In both tables as well as in the text following Table 16 the compounds are referred to with reference to an Example number, with reference to a letter code identified in the key beneath Table 15, or with reference to a number code identified in the text.

TABLE 15

| | RATS | | | MICE | | |
|---|---|---|---|---|---|---|
| | MES | | | MES | | |
| Compound | 50 | PI | TD50 | ED50 | PI | TD50 |
| A | 36 | >4.7 | >168 | <100 | >1 | >100 |
| B | 184 | 2.7 | 492 | 80 | 1.1 | 71 |
| C | 17 | >29.4 | >500 | 18 | 1.4 | 25 |
| 18 | 14 | >35.7 | >500 | 31 | 2.4 | 75 |
| 19 | 24 | >20.8 | >500 | 40 | 1.5 | 61 |
| 4 | | | | <100 | | |
| 1 | 50 | >1 | >50 | 77 | 2.6 | 198 |
| 2 | 21 | >23 | >500 | 39 | 3.5 | 137 |
| D | 105 | >1.7 | >180 | 83 | >1.5 | 127 |
| E | <50 | >1 | >50 | 79 | >1.9 | 153 |
| F | | | | <300 | >1 | >300 |
| G | 57 | >9 | >500 | 57 | >9 | >500 |
| H | 50 | | | 50 | 2.8 | 141 |
| 14 | 94 | >1.5 | >142 | <100 | >1 | 100 |
| 15 | 50 | | >50 | | | <100 |
| I | <50 | >1 | >50 | 66 | 1.1 | 58 |
| J | <50 | >1 | >50 | 65 | 1.2 | 78 |
| K | | | | 115 | | <250 |
| L | 50 | >1 | >50 | 74 | 2.5 | 188 |
| 5 | | | | <100 | >3 | >300 |
| 34 | | | | <300 | | >300 |
| 31 | | | >50 | <100 | | <100 |
| 25 | 50 | >1 | | <100 | <1 | >100 |
| M | <50 | >i | >50 | <100 | | <100 |
| 39 | <50 | >1 | >50 | <1000 | | <100 |
| 28 | <50 | >1 | >50 | <100 | | <100 |
| 38 | 50 | >1 | >50 | <100 | | <100 |
| 40 | <50 | >1 | >50 | <100 | | <100 |
| 21 | 21 | | >500 | 40 | | 137 |
| 8 | 24 | | >500 | | | |
| 17 | | | | 33 | 3 | 90 |
| 23 | 25 | 20 | >500 | 65 | 2.2 | 155 |
| 26 | 40 | 12.5 | >500 | | | |
| 46 | | | | 82 | 6 | 500 |
| 5* | | | | 58 | 2.6 | 138 |
| 3* | | | | 83 | 1.6 | 127 |
| 16 | 50 | >1 | >50 | <50 | | |
| 11 | <50 | >1 | >50 | <300 | 1 | <300 |
| 27 | <50 | >1 | >50 | <100 | >1 | >100 |
| 20 | <50 | >1 | >50 | <100 | >1 | 100 |
| 22 | <50 | >1 | >50 | <100 | >1 | >100 |
| 43 | <50 | >1 | >50 | <100 | 1 | <100 |
| 3 | <50 | >1 | >50 | <100 | >1 | >100 |
| 42 | <50 | >1 | >50 | | | |

A. 1-aminoindan
B. (R)-1-aminoindan
C. (S)-1-aminoindan
D. HCl salt of 1
E. (R)-N-propargyl-1-aminoindan HCl salt TABLE 15-continued

|  | RATS | | | MICE | | |
|---|---|---|---|---|---|---|
|  | MES | | | MES | | |
| Compound | 50 | PI | TD50 | ED50 | PI | TD50 |

F. (R)-N-propargyl-1-aminoindan mesylate salt
G. (S)-N-propargyl-1-aminoindan HCl salt
H. (S)-N-propargyl-1-aminoindan mesylate salt
I. 6-fluoro-1-aminoindan
J. (R)-6-fluoro-1-aminoindan
K. (S)-6-fluoro-1-aminoindan
L. 6-fluoro-N-propargyl-1-aminoindan
M. aminotetralin
5*. base of compound 5
3*. base of compound 3

TABLE 16

| | RATS | | | MICE | | |
|---|---|---|---|---|---|---|
| | scMet | | | scMet | | |
| Compound | ED50 | PI | TD50 | ED50 | PI | TD50 |
| A | >250 | | >168 | | | >100 |
| B | >250 | | 492 | >100 | | 71 |
| C | >250 | | >500 | >60 | | 25 |
| 18 | >250 | | >500 | 66 | | 75 |
| 19 | >250 | | >500 | 86 | | 61 |
| 4 | | | | | | |
| 1 | | | >50 | >200 | | 198 |
| 2 | >250 | | >500 | >150 | | 137 |
| D | | | >180 | >130 | | 127 |
| E | >154 | | >50 | | | 153 |
| F | | | | | | >300 |
| G | >250 | | >500 | >250 | | >500 |
| H | | | | >200 | | 141 |
| 14 | >71 | | >142 | | | 100 |
| 15 | | | >50 | | | <100 |
| I | >100 | | >50 | | | 58 |
| J | >100 | | >50 | | | 78 |
| K | | | | | | <250 |
| L | >300 | | >50 | | | 188 |
| 21 | >250 | | >500 | 150 | | 137 |
| 8 | >250 | | >500 | | | |
| 17 | | | | 71.5 | | 90 |
| 23 | >250 | | >500 | 155 | | 155 |
| 26 | >250 | | >500 | | | |
| 46 | | | | >500 | | >500 |
| 5* | | | | >200 | | 138 |
| 3* | | | | >130 | | 127 |
| 3 | | | | 36 | | 126 |

The racemic and individual enantiomers of 1-aminoindan showed activity in the MES model, indicating an activity in generalized and partial seizures. Surprisingly, there were significant differences between the activities of the (R) and (S) enantiomers. In the MES test in rats, whereas the racemic compound A had an median effective dose of 36 mg/kg, the (R) enantiomer B had an ED5O of 184. The ED50 of the (S) enantiomer C was 17. This difference was also observed in mice. The (R) isomer had an ED50 of 80, whereas the (S) isomer had an ED50 of 18.

An activity against generalized and partial seizures was also observed in with N-acetyl analogs of 1-aminoindan. Compound 18 ((R)-N-acetyl aminoindan) had an ED50 of 14 in the MES test in rats, and 31 in mice. This value in rats is approximately 35 times lower than that observed for valproic acid, 2 times lower than that found for phenytoin and 1.6 times that found for Carbamazepine. As these three agents are considered to be the drugs of choice for generalized an partial epilepsy, efficacy against these seizures are also indicated for this compound and the other compounds specified as active in the application. Compound 19 ((S)-N-acetylaminoindan) had an ED50 of 24 in MES test in rats, and 40 in mice. These compounds also showed activity in the s.c. Met model in mice, which is representative of absence seizures. Compound 18 had an ED50 of 66, whereas Compound 19 had an ED50 of 86.

The high activity observed with the above compounds was also observed when the 1-amino moiety was substituted with a glycinamide moiety. As with the 1-aminoindan compounds, the glycinamide analogs also showed differences between the (R) and (S) enantiomers, and whether the compound was the HCl salt of free base. Compound 2 ((R)-Indanylglycinamide-free base) had an ED50 of 21 in rats and 39 in mice. D ((R)-Indanylglycinamide-HCl salt) had an ED50 in rats of 105 and 83 in mice.

Compounds were also found to be active when the 1-amino moiety was substituted with propargyl moiety. The compounds were also found to be active whether they were HCl or mesylate salts. E ((R)-Propargylaminoindan-HCl) had an ED50 less than 50 in rats and 79 in mice. G (S)-Propargyl aminoindan had an ED50 of 57 in rats and mice. The mesylate salt of this compound H also had an ED50 of 50 or less in mice and rats in the MES test.

Activity was also found with compounds in which the 1-amino moiety was substituted with aliphatic side chains. Compound 14 ((S)-N-methyl aminoindan) showed activity in the MES test in both rats (ED50=94) and mice (ED50<100). Fluorinated analogs of 1-aminoindan also had activity in the MES test. "I" has approximately the same efficacy. J had a better efficacy profile. The ED50 was less than 50 in rats, 3 times more efficacious than that observed for B. K also showed activity in the MES model in mice. Compound 5 also showed activity in mice in the MES model. L also showed activity in mice in this model.

Hydroxylated analogs of 1-aminoindan, also show activity in the MES model. Compound 34 (6-hydroxy analog of 1-aminoindan) showed activity in the MES test in mice.

Activity in the MES model was also observed in methoxy analogs of 1-aminoindan. Compound 31 (4,5 dimethoxy 1-aminoindan) showed activity in the mice.

In addition, amino tetralins also showed activity in the MES mode. M (1-amino tetralin) had an ED50 of less than 50 in rats and less than 100 in mice. Substitution on the 1-amino group with glycinamide also showed activity in mice.

EXAMPLE 6

Neurotoxicity and Protective Index

Neurotoxicity of the claimed agents was also assessed in mice (i.p. administration) by the rotorod ataxia test and/or in rats (p.o. administration) by positional sense test and gait stance test. See E. A. Swinyard, et al., in "Antiepileptic Drugs," ed. by R. H. Levy, et al., Raven Press, New York, at 85–200 (1989). The term quantitating the neurotoxicity is the medial neurological toxic dose (TD50), was determined in the above tests. The results obtained in mg/kg are shown in the relevant positions of Tables 15 and 16. In some of the species, the TD50 was only determined to be above a certain level, indicating a lower neurotoxicity than specified.

The Protective Index (PI) is defined as the ratio of TD50 and ED5O (PI=TD50/ED50). The PI is used to show a useful separation between neurotoxicity and antiepileptic activity. The larger the PI, the better the separation between the neurotoxic and efficacious doses. The preferred embodiment of this application is therefore those compounds in which we have already demonstrated a PI>1 in the MES model of one of the species tested. Where the TD50 is only listed as greater than a particular value, the PI will represent a minimum value, and therefore a better index.

The racemic 1-aminoindan analog A and the individual enantiomers B and C had PI values in rats of >4.7, 2.7 and >29.4, respectively. The PI values of the N-acetyl analogs Compound 17 and Compound 16 was >20.8, and >35.7 respectively. The PI values of the N-glycinamide analogs Compound 1 and Compound 2 is >1, and >23.

EXAMPLE 7

Effect of Aminoindans of Mice Having Experienced a Hypobaric Hypoxic Episode The hypobaric hypoxic model is a well accepted model for assessing the activity of compounds believed to possess neuroprotective activity. The model is based on that described in Nakanishi M et al. Life Sci. (1973) 13, 467, Oshiro et al., J. Med. Chem. (1991) 34, 2004–2013 and U.S. Pat. No. 4,788,130.

A 121 desiccator (desiccator A) and a 2.51 desiccator (desiccator B) were separately connected to a vacuum pump. Desiccator B was disconnected and allowed to equilibrate with room air whilst desiccator A was evacuated to a pressure of 100 mmHg. Four male ICR albino mice (22–28 g) were placed in desiccator B. Desiccator B was then closed to room air and connected to desiccator A. The pressure inside desiccator B was monitored using a mercury manometer and at the point were the pressure in desiccator B reached 200 mmHg (usually within 14 seconds), the two desiccators were disconnected from the vacuum pump and the pump switched off. The survival time from the moment of induction of hypoxia to the time of cessation of respiration was recorded for each mouse for a maximum of 15 minutes after which time room air was reintroduced to desiccator B. Survivors were monitored for signs of lethargy or vitality.

Effect of drug treatment was assessed as the percent of the survival time of the drug treated group with respect to the saline injected or vehicle injected control group. Control groups were run twice, before and after each experimental group and consisted of 12–16 mice in groups of 4 mice. Each experimental group always consisted of 4 mice to ensure a constant residual volume of oxygen in all tests. The effect of each dose of test drug was determined in duplicate i.e. two groups of 4 mice. The range of survival times of control mice was from 108–180 seconds.

All drugs were administered intra-peritoneally at the dose indicated one hour prior to exposure to hypoxia. Reference drugs were administered as follows; sodium pentobarbital, 20 or 40 mg/kg given 0.5 hour prior to hypoxia, diazepam, 5 or 10 mg/kg given 0.5 hour prior to hypoxia. The results are shown in Tables 17 and 18 below.

TABLE 17

| TREATMENT | | PROTECTION % OF | |
|---|---|---|---|
| COMPOUND | DOSE (mg/kg ip) | RESPECTIVE CONTROL | SIGNIFICANCE "t" TEST |
| Diazepam | 10 | 430 ± 59 | p < 0.001 |
|  | 5 | 249 ± 166 | p < 0.05 |
| Pentobarbitone | 40 | 446 ± 10.5 | p < 0.001 |
|  | 20 | 325 ± 166 | p < 0.002 |
| B | 100 | 395 ± 199 | P < 0.001 |

TABLE 17-continued

| TREATMENT | | PROTECTION % OF | |
|---|---|---|---|
| COMPOUND | DOSE (mg/kg ip) | RESPECTIVE CONTROL | SIGNIFICANCE "t" TEST |
|  | 50 | 358 ± 224 | p < 0.01 |
|  |  | 411 ± 174 | p < 0.001 |
| C | 100 | 404 ± 244 | p < 0.002 |
|  | 50 | 174 ± 39 | p < 0.01 |
|  |  | 264 ± 66 | p < 0.001 |
| 18 | 100 | 397 ± 244 | p < 0.01 |
|  | 50 | 271 ± 193 | p < 0.05 |
|  |  | 383 ± 233 | p < 0.01 |

TABLE 18

| TREATMENT | | PROTECTION % OF | |
|---|---|---|---|
| COMPOUND | DOSE (mg/kg ip) | RESPECTIVE CONTROL | SIGNIFICANCE "t" TEST |
| (R)-6-fluoro-1-aminoindan | 100 | 241 ± 56 | p < 0.001 |
|  | 50 | 305 ± 185 | p < 0.01 |
| 30 | 100 | 379 ± 202 | p < 0.001 |
|  | 50 | 265 ± 284 | ns |
| 42 | 100 | 228 ± 119 | p < 0.02 |
|  | 50 | 179 ± 170 | ns |
| 39 | 100 | 798 ± 249 | p < 0.001 |
|  | 50 | 600 ± 213 | p < 0.001 |
| 41 | 100 | 644 ± 316 | p < 0.001 |
|  | 50 | 187 ± 41 | p < 0.001 |
| 28 | 100 | 941 ± 34 | p < 0.001 |
|  | 50 | 361 ± 106 | p < 0.001 |
| 1-Aminotetralin | 100 | 345 ± 134 | p < 0.001 |
|  | 50 | 158 ± 54 | p < 0.02 |
| 40 | 100 | 569 ± 173 | p < 0.001 |
|  | 50 | 374 ± 190 | p < 0.001 |

EXPERIMENT 8

Cultures of Mechanically Dissociated Neonatal Rat Cerebellum

A. Reversal of NMDA induced cell death.

The cerebellum was aseptically dissociated from 6 or 7-day old rat pups and placed in a 15 ml sterile plastic conical tube containing 3 ml of Dulbecco's modified Eagle's medium (DMEM) with a high glucose concentration (1 g/ml) and 2 mM (v/v) L-glutamine and an antibiotic antimitotic mixture. The cerebella were then dissociated after 20–25 passages through a sterile 13 gauge, 10 cm long stainless steel needle attached to a 5 ml syringe with an inserted 45 micrometer pore nylon sieve. The dissociated cells were centrifuged at 200 g for 5 minutes. The supernatant was discarded and the cells resuspended in medium enriched with 15% (v/v) heat inactivated fetal calf serum. Cell viability was determined by the tryptan blue exclusion test.

Cells were plated at a density of $200/mm^2$ on poly-L-lysine coated surfaces. Poly-L-lysine coated glass coverslips were prepared at least one hour in advance of plating by immersing sterile coverslips in sterile distilled water solution containing 15 Microgram/ml poly-L-lysine, and washing in sterile water just prior to use. The plated cells were covered with enriched medium and incubated at 37° C. in an atmosphere of 5% $CO_2$ in air and 97% humidity. After three days in culture, the media was replaced with media containing the desired test compound. Each test compound was tested in duplicate. Toxic-dose response was determined for each compound.

Four groups were run in each set of experiments;
I. Control, consisting of enriched media alone,
II. N-methyl-D-aspartate (NMDA, 1 mM for 3 hours) as the cytotoxic challenge,
III. Test compound plus NMDA, and
IV. Positive control, spermine(0.01 micromoles) plus NMDA.

Nerve cell survival was evaluated by phase contrast microscopy and tryptan blue staining after 24 hours.

Results

The results are shown in Table 19 below. Surviving cells in culture are measured relative to control (100%) as described above. Percent protection is the Cell Survival for the test compound minus the NMDA effect. Thus, maximal protection is 100% minus 30%. NMDA effect i.e. 70%. The Effective Protection was calculated as the percent of the Percent Protection (X) divided by the maximal protection value (e.g. X×100/70).

TABLE 19

| COMPOUND | EXPERMNT'L GROUP Dose (μM) | SURVIVING CELL IN CULTURE | PERCENT PROTECTION | EFFECTIVE PROTECTION |
|---|---|---|---|---|
| | Control | 100 | | |
| | NMDA | 30 | | |
| | Max protection | | 70 | 100 |
| | Spermine + NMDA | 82 | 52 | 74 |
| 18 | 0.005 + NMDA | 80 | 50 | 71 |
| | 0.010 | 80 | 50 | 71 |
| | 0.100 | 55 | 25 | 36 |
| | 1.000 | 47 | 17 | 24 |
| | 5.000 | 32 | 2 | 3 |
| (R)-6-fluoro- | 0.005 | 108 | 78 | 111 |
| 1-aminoindan | 0.010 | 79 | 49 | 70 |
| | 0.100 | 62 | 32 | 46 |
| | 1.000 | 53 | 23 | 33 |
| | 5.000 | 60 | 30 | 43 |
| 19 | 0.001 | 80 | 50 | 71 |
| | 0.005 | 30 | 0 | 0 |
| | 0.010 | 42 | 12 | 17 |
| | 1.000 | 15 | −15 | — |
| 2 | 0.005 | 56 | 26 | 37 |
| | 0.010 | 51 | 21 | 30 |
| | 0.100 | 33 | 3 | 4 |
| 35 | 0.005 | 60 | 30 | 43 |
| | 0.010 | 34 | 4 | 6 |
| | 0.100 | 30 | 0 | 0 |
| (R)-1-amino- | 0.005 | 80 | 50 | 71 |
| indan | 0.010 | 30 | 0 | 0 |
| | 0.100 | 28 | −2 | — |

In a separate experiment wherein the Maximum Protection possible was 90%, compound C (1-S-aminoindan) displayed an Effective Protection value of 43% at 0.01 μM and 57% at 0.05 μM.

B. Enhancement of Cell Survival.

Cell cultures were grown as described above but in the absence of NMDA and after 3 days a dose of test compound was added. Cell survival was monitored as described above. Naturally (control) the cells die over a period of seven days from plating. Measurements of cell survival taken 24 hours after the addition of test compound (four days after cell plating) showed that the test compounds enhanced the survival of the cells, delaying their natural death. Table 20 below shows the per cent increase in No of cells present on the fourth day expressed as percentage of the number of control cells on that day.

TABLE 20

| COMPOUND | DOSE μM | % ENHANCED SURVIVAL |
|---|---|---|
| 18 | 0.01 | 145 |
| | 0.10 | 130 |
| | 1.00 | 126 |
| 19 | 0.005 | 120 |
| 2 | 0.005 | 140 |
| | 0.010 | 125 |
| (R)-1-aminoindan | 0.005 | 121 |

EXAMPLE 9

Global Brain Ischemia in Gerbils

Male mongolian gerbils, aged 2.5–5 months, housed 4–8 in a cage, were supplied freely with food and water and maintained at 24° C. with a 12 hour day/night cycle. For surgery the animals were anesthetized with halothane (1.5% in 100% $O_2$) and the common carotid arteries exposed bilaterally through a midline ventral neck incision. Each artery was clamped for 5 minutes with aneurysm clips to produce global brain ischemia. The anesthesia was discontinued upon clamping. After 5 minutes the clamps were removed and the wound closed with skin clips.

For treatment, the test compound or vehicle were injected intra-peritoneally (ip) in a volume of 50 microliters of solvent per 10 g body weight. The first injection was given two minutes after clamp removal, and thereafter daily for the next 2 post-operative days (total of 3 injections).

Seven groups each of 4–8 animals were compared:
I. Control; (sham- or unoperated and saline treated),
II. Vehicle treated, unoperated (when solvent is other than saline), III. Ischemia—untreated or saline treated), IV. Ischemia—vehicle treated (when solvent is other than saline)

V. Ischemia—Test compound treated, one sub-group per concentration tested,

VI. Ischemia and pentobarbital (40 mg/kg) as positive control).

Analysis of neuronal damage was performed 14 days post-ischemia by counting pyramidal neurons throughout the CA1 layer of the anterior hippocampus in 4 micromolar thick (paraffin) coronal brain sections stained with hematoxylin and erosin.

The Results are shown in the Table 21 below. Percent Protection values represent the fraction of hippocampi protected from ischemia in a group of animals treated with the stated dose of compound.

TABLE 21

| TEST COMPOUND | (n) | DOSE (mg/kg) | % INTACT NEURONS | PERCENT PROTECTION |
|---|---|---|---|---|
| Control | | | 100 | |
| Ischemia | | | 0 | |
| Pentobarbital | (8) | | | 87.5 |
| 18 | (8) | 0.1 | | 25.0 |
| | (8) | 1.0 | | 25.0 |
| | (4) | 10.0 | | 66.7 |
| (R)-6-fluoro-1-aminoindan | (8) | 0.1 | | 27.5 |
| | (8) | 1.0 | | 25.0 |
| | (8) | 10.0 | | 25.0 |
| 19 | (4) | 0.1 | | 25.0 |
| | (2) | 1.0 | | 0 |
| | (4) | 10.0 | | 37.5 |
| (R)-1-aminoindan | (4) | 0.1 | | 25.0 |
| | (4) | 1.0 | | 25.0 |
| | (4) | 10.0 | | 25.0 |
| (S)-1-aminoindan | (4) | 0.1 | | 0 |
| | (4) | 1.0 | | 50.0 |
| | (4) | 10.0 | | 75.0 |
| 2 | (4) | 0.1 | | 0 |
| | (2) | 1.0 | | 50.0 |
| | (4) | 10.0 | | 37.5 |
| 35 | (8) | 0.1 | | 25.0 |
| | (8) | 1.0 | | 37.5 |
| | (7) | 10.0 | | 37.5 |

EXAMPLE 10

Electrically Kindled Rat Model of Epilepsy

The rat electrical kindling model of epilepsy has been known to show efficacy of antiepileptic agents against complex partial seizures that evolve into generalized motor seizures. In these tests, rats were electrically stimulated via corneal electrodes twice daily for approximately 5 days and then once daily for an additional 10 days. Once the seizure criteria, as described by R. J. Racine, et al., *Electroenceph. Clin. Neurophysiol.* 32: 281–294 (1972), were met, the test substance was administered p.o. to rats, and the rat electrically stimulated, and observed for the presence or absence of a seizure. The detailed procedure of this test model can be found in, E. A. Swinyard, et al., in "Antiepileptic Drugs," ed. by R. H. Levy, et al., Raven Press, New York, at 85–100 (1989) and Racine, Id.

Further, in the electrically kindled rat model, compound 18 (administered p.o.) prevented seizures with an $ED_{50}$ of 24.6 Mg/kg; compound 17 with an $ED_{50}$ of <75 mg/kg; and compound 19 with an $ED_{50}$ of >50 mg/kg. The results are therefore indicative of these compounds having an efficacy against generalized seizures and complex partial seizures which evolve into generalized motor seizures.

What is claimed is:

1. A method for treating dementia in a subject comprising administering to the subject a therapeutically effective amount of a compound of the formula:

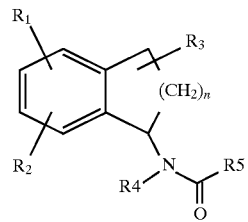

or a pharmaceutically acceptable salt thereof;
wherein
n is 0 or 1;
$R_1$ and $R_2$ are each independently hydrogen, substituted or unsubstituted $C_1$–$C_4$ alkyl, halogen, nitro, —NH—$R_{11}$, —C(O)—$R_{11}$ or —C(O)—$NR_9R_{10}$, wherein
$R_{11}$ is hydrogen, substituted or unsubstituted $C_1C_4$ alkyl, hydroxy, substituted or unsubstituted $C_1$–$C_4$ alkoxy, and
$R_9$ and $R_{10}$ are each independently hydrogen, $C_1$–$C_{12}$ alkyl, substituted or unsubstituted $C_6$–$C_{12}$ aryl, substituted or unsubstituted $C_7$–$C_{12}$ aralkyl, or indanyl;
$R_3$ is hydrogen, substituted or unsubstituted $C_1$–$C_4$alkyl, hydroxy, substituted or unsubstituted $C_1$–$C_4$ alkoxy;
$R_4$ is hydrogen, substituted or unsubstituted $C_1$–$C_{12}$ alkyl, substituted or unsubstituted $C_6$–$C_{12}$ aryl, substituted or unsubstituted $C_7$–$C_{12}$ aralkyl, or —C(O)—$R_6$,
wherein $R_6$ is hydrogen, $C_1$–$C_{12}$ alkly, substituted or unsubstituted $C_6$–$C_{12}$ aryl, substituted or unsubstituted $C_7$–$C_{12}$ aralkyl;
$R_5$ is hydrogen, $C_1$–$C_{12}$ alkyl, substituted or unsubstituted $C_6$–$C_{12}$ aryl, substituted or unsubstituted $C_7$–$C_{12}$ aralkyl, or A—$NR_9R_{10}$, —Y—C(O)—$R_7$ or —Y—$(SO2)NR_9R_{10}$,
wherein A is substituted or unsubstituted $C_6$–$C_{12}$ aryl, substituted or unsubstituted $C_7$–$C_{12}$ aralkyl, and
$R_9$ and $R_{10}$ are each independently hydrogen, substituted $C_1$–$C_{12}$ alkyl, substituted or unsubstituted $C_6$–$C_{12}$ aryl, substituted or unsubstituted $C_7$–$C_{12}$ aralkyl, or indanyl;
Y is substituted or unsubstituted $C_6$–$C_{12}$ aryl, substituted or unsubstituted $C_7$–$C_{12}$ aralkyl, and
$R_7$ is hydrogen, hydroxy, substituted or unsubstituted $C_6$–$C_{12}$ aryl, substituted or unsubstituted $C_7$–$C_{12}$ aralkyl.

2. The method according to claim 1, wherein a compound selected from the group consisting of: N-(4-aminobutanoyl)-1-aminoindan,(R)-N-formyl-1-aminoindan, (S)-N-formyl-1-aminoindan, (R)-N-acetyl-1-aminoindan, (S)-N-acetyl-1-aminoindan, N-acetyl-7-methyl-1-aminoindan, N-acetyl-6-fluoro-1-aminoindan, (R)-N-acetyl-6-fluoro-1-aminoindan, N-acetyl-6-methoxy-1-aminoindan, (R)-N-acetyl-4,5-dimethoxy-1-aminoindan, N-(2-acetamido)-1-aminoindan, (R)-N-(2-acetamido)-1-aminoindan, (S)-N-(2-acetamido)-1-aminoindan, N-(2-acetamido)-6-fluoro-1-aminoindan, N-(3-cyanopropyl)-1-aminoindan, N-(2-N-Boc-aminoacetyl)-1-aminoindan, N-(2-aminoacetyl)-1-aminoindan, N-benzoyl-1-aminoindan, N-(2-n-propylpentanoyl)-1-aminoindan, N-(2-propionamido)-1-aminoindan, N-butyryl-1-aminoindan, N-(2-phenylacetyl)-1-aminoindan, N-(m-anisoyl)-1-aminoindan, N-(4'-fluorobenzoyl)-1-aminoindan, N-(p-4- toluoyl)-1-aminoindan, (S)-(1-indanyl)-glycine, N,N-di-(2-acetamido)-1-aminoindan, N-(1-indanyl)aminoacetonitrile, 6-cyano-N-acetyl-1-aminoindan, 6-carboxamido-N-acetyl-1-aminoindan, 6-ethoxycarbonyl-N-acetyl-1aminoindan, 2-(1-indanamino)-N-isopropylethanesulfonamide, 2-(1-indanamino)-N-(1-indanyl) ethanesulfonamide, (R,R)-2-(1-indanamino)-N-(1-indanyl) ethanesulfonamide, N-(4-di-n-propylsulfamoyl) benzoyl-1-aminoindan, N-N'-bis-(1-indanyl) adipamide, N-N'-bis-(R)-(1-indanyl) adipamide, N-N'-bis-(R)-(1-indanyl) succinamide, (trans)-2-methyl-N-acetyl-1-aminoindan, (cis)-2-methyl-N-acetyl-1-aminoindan, N-methyl-N-acetyl-1-aminoindan, (R)-N-methyl-N-acetyl-1-aminoindan, and salts thereof.

3. The method according to claim wherein the dementia is senile dementia.

4. The method according to claim 1, wherein the dementia is dementia of the Alzheimer's type.

5. The method according to claim 1, wherein the dementia is dementia of the Parkinson's type.

6. The method according to claim 1, wherein the subject is a human subject.

7. The method according to claim 1, wherein the administering comprises administering orally, rectally, transdermally, or parenterally.

8. The method according to claim 1, wherein the therapeutically effective amount is from about 1 milligram to about 1000 milligrams.

9. The method according to claim 1, wherein the therapeutically effective amount is from about 10 milligrams to about 100 milligrams.

10. The method according to claim 1, wherein the pharmaceutically acceptable salt is a hydrochloride salt, a mesylate salt, an ethylsulfonate salt, or a sulfate salt.

11. The method according to claim 1, wherein n is 1.

12. The method according to claim 1, wherein n is 2.

13. The method according to claim 1, wherein $R_1$ and $R_2$ are each independently hydrogen, fluoro, or methyl.

14. The method according to claim 1, wherein $R_4$ and $R_5$ are each independently hydrogen, or substituted or unsubstituted $C_1$–$C_{12}$ alkyl.

15. The method according to claim 1, wherein $R_4$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group.

16. The method according to claim 15, wherein the lipophilic group is selected from the group consisting of piperazinyl, piperidinyl, morpholinyl, pyrrolidinyl, adamantyl, quinuclindyl, and substituted derivatives thereof.

17. The method according to claim 1, wherein $R_5$ is $C_1$–$C_{12}$ alkyl substituted with a lipophilic group, $C_6$–$C_{12}$ aryl substituted with a lipophilic group, or $C_7$–$C_{12}$ aralkyl substituted with a lipophilic group.

18. The method according to claim 17, wherein the lipophilic group is selected from the group consisting of piperazinyl, piperidinyl, morpholinyl, pyrrolidinyl, adamantyl, quinuclindyl, and substituted derivatives thereof.

19. The method of claim 1, wherein A is substituted or unsubstituted $C_1$–$C_{12}$ alkyl.

20. The method of claim 1, wherein Y is substituted or unsubstituted $C_1$–$C_{12}$ alkyl.

21. The method of claim 1, wherein $R_7$ is substituted or unsubstituted $C_1$–$C_{12}$ alkyl.

22. The method according to claim 1, wherein $R_4$ is —C(O)—$R_6$, wherein $R_6$ is alkyl or $ANR_9R_{10}$,
wherein A is alkyl, and $R_9$ and $R_{10}$ are each independently hydrogen, or substituted or unsubstituted $C_1$–$C_{12}$ alkyl.

23. The method according to claim 1, wherein $R_5$ is —C(O)—$R_6$, wherein $R_6$ is alkyl or $ANR_9R_{10}$,
wherein A is alkyl, and $R_9$ and $R_{10}$ are each independently hydrogen, or substituted or unsubstituted $C_1$–$C_{12}$ alkyl.

24. The method according to claim 1 wherein $R_4$ is —Y—C(O)—$R_7$, wherein Y is substituted or unsubstituted $C_1$–$C_{12}$ alkyl and $R_7$ is $NR_9R_{10}$.

25. The method according to claim 1 wherein $R_5$ is —Y—C(O)—$R_7$, wherein Y is substituted or unsubstituted $C_1$–$C_{12}$ alkyl and $R_7$ is $NR_9R_{10}$.

26. The method according to claim 1 wherein $R_3$ and $NR_4R_5$ are in a cis spatial configuration.

27. The method according to claim 1 wherein $R_3$ and $NR_4R_5$ are in a trans spatial configuration.

28. The method according to claim 1 wherein the compound is an R enantiomer.

29. The method according to claim 1 wherein the compound is an S enantiomer.

* * * * *